(12) United States Patent
Lee et al.

(10) Patent No.: US 12,356,795 B2
(45) Date of Patent: Jul. 8, 2025

(54) LIGHT EMITTING DIODE AND DISPLAY DEVICE INCLUDING THE SAME

(71) Applicant: Samsung Display Co., Ltd., Yongin-si (KR)

(72) Inventors: Bora Lee, Hwaseong-si (KR); Hyomin Ko, Suwon-si (KR); Illhun Cho, Seoul (KR); Eunjae Jeong, Hwaseong-si (KR); Minji Kim, Hwaseong-si (KR); Sohee Jo, Cheonan-si (KR); Dongjun Kim, Suwon-si (KR); Hankyu Pak, Suwon-si (KR); Sanghyun Han, Hwaseong-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 63 days.

(21) Appl. No.: 18/347,995

(22) Filed: Jul. 6, 2023

(65) Prior Publication Data
US 2023/0363261 A1 Nov. 9, 2023

Related U.S. Application Data

(63) Continuation of application No. 17/153,310, filed on Jan. 20, 2021, now Pat. No. 11,744,147.

(30) Foreign Application Priority Data

Jan. 21, 2020 (KR) .................. 10-2020-0007949
Dec. 16, 2020 (KR) .................. 10-2020-0176483

(51) Int. Cl.
*H10K 50/852* (2023.01)
*C07C 211/54* (2006.01)
(Continued)

(52) U.S. Cl.
CPC .......... *H10K 50/852* (2023.02); *C07C 211/54* (2013.01); *C07C 211/61* (2013.01);
(Continued)

(58) Field of Classification Search
None
See application file for complete search history.

(56) References Cited

U.S. PATENT DOCUMENTS

| 4,720,432 A | 1/1988 | Vanslyke et al. |
| 5,061,569 A | 10/1991 | Vanslyke et al. |

(Continued)

FOREIGN PATENT DOCUMENTS

| CN | 105658620 A | 6/2016 |
| CN | 108717941 A | 10/2018 |

(Continued)

OTHER PUBLICATIONS

U.S. Appl. No. 17/874,578, filed Jul. 27, 2022.
(Continued)

*Primary Examiner* — Anthony Ho
(74) *Attorney, Agent, or Firm* — KILE PARK REED & HOUTTEMAN PLLC

(57) ABSTRACT

A light emitting diode of an embodiment includes a first electrode, a hole transport region disposed on the first electrode, an emission layer disposed on the hole transport region, an electron transport region disposed on the emission layer, and a second electrode disposed on the electron transport region. The hole transport region includes a first hole transport layer disposed adjacent to the first electrode and having a first refractive index, a second hole transport layer disposed adjacent to the emission layer and having a second refractive index, and a third hole transport layer disposed between the first hole transport layer and the second hole transport layer and having a third refractive (Continued)

index which is greater than each of the first refractive index and the second refractive index, thereby showing high light extraction efficiency and high emission efficiency properties.

6 Claims, 5 Drawing Sheets

(51) Int. Cl.
| | |
|---|---|
| C07C 211/61 | (2006.01) |
| C07D 209/88 | (2006.01) |
| C07D 307/91 | (2006.01) |
| C07D 333/76 | (2006.01) |
| H10K 50/15 | (2023.01) |
| H10K 50/818 | (2023.01) |
| H10K 50/828 | (2023.01) |
| H10K 50/858 | (2023.01) |
| H10K 85/60 | (2023.01) |
| H10K 102/00 | (2023.01) |

(52) U.S. Cl.
CPC ......... *C07D 209/88* (2013.01); *C07D 307/91* (2013.01); *C07D 333/76* (2013.01); *H10K 50/15* (2023.02); *H10K 50/156* (2023.02); *H10K 50/818* (2023.02); *H10K 50/828* (2023.02); *H10K 50/858* (2023.02); *H10K 85/633* (2023.02); *H10K 85/636* (2023.02); *C07C 2601/14* (2017.05); *C07C 2603/18* (2017.05); *C07C 2603/74* (2017.05); *H10K 85/615* (2023.02); *H10K 85/626* (2023.02); *H10K 85/6572* (2023.02); *H10K 85/6574* (2023.02); *H10K 85/6576* (2023.02); *H10K 2102/3026* (2023.02); *H10K 2102/351* (2023.02)

(56) References Cited

U.S. PATENT DOCUMENTS

| | | | |
|---|---|---|---|
| 6,242,115 | B1 | 6/2001 | Thomson et al. |
| 7,470,933 | B2 | 12/2008 | Lee et al. |
| 7,777,413 | B2 | 8/2010 | Kuma et al. |
| 8,021,764 | B2 | 9/2011 | Hwang et al. |
| 8,471,463 | B2 | 6/2013 | Sumida et al. |
| 8,530,888 | B2 | 9/2013 | Jeong et al. |
| 8,963,143 | B2 | 2/2015 | Loebl et al. |
| 9,209,425 | B2 | 12/2015 | Mizuno |
| 9,293,732 | B2 | 3/2016 | Pyo et al. |
| 9,412,964 | B2 | 8/2016 | Sotoyama et al. |
| 10,483,479 | B2 | 11/2019 | Tanaka |
| 10,847,740 | B2 | 11/2020 | Wang et al. |
| 11,407,854 | B2 | 8/2022 | Burkhart et al. |
| 11,805,697 | B2 | 10/2023 | Miyake et al. |

| | | |
|---|---|---|
| 2011/0215308 A1 | 9/2011 | Im et al. |
| 2016/0043317 A1 | 2/2016 | Takada et al. |
| 2016/0079542 A1 | 3/2016 | Itoi |
| 2016/0133850 A1 | 5/2016 | Matsuura et al. |
| 2016/0197277 A1 | 7/2016 | Kato et al. |
| 2019/0016666 A1 | 1/2019 | Jeong et al. |
| 2019/0288220 A1 | 9/2019 | Kim et al. |

FOREIGN PATENT DOCUMENTS

| | | |
|---|---|---|
| CN | 110078705 A | 8/2019 |
| EP | 2 347 896 | 7/2011 |
| JP | 6-314594 | 11/1994 |
| JP | 8-291115 | 11/1996 |
| JP | 11-144873 | 5/1999 |
| JP | 2000-302756 | 10/2000 |
| JP | 2000-309566 | 11/2000 |
| JP | 2005-150042 | 6/2005 |
| JP | 2006-151979 | 6/2006 |
| JP | 2013-258269 | 12/2013 |
| JP | 2014-212102 | 11/2014 |
| JP | 2016-39187 | 3/2016 |
| JP | 2016-58549 | 4/2016 |
| JP | 2016-92297 | 5/2016 |
| JP | 2019-161221 | 9/2019 |
| JP | 6696091 | 5/2020 |
| KR | 10-2005-0120400 | 12/2005 |
| KR | 10-2011-0101418 | 9/2011 |
| KR | 10-1084197 | 11/2011 |
| KR | 10-1496789 | 2/2015 |
| KR | 10-2016-0017596 | 2/2016 |
| KR | 10-2016-0030429 | 3/2016 |
| KR | 10-2016-0055675 | 5/2016 |
| KR | 10-1708176 | 2/2017 |
| KR | 10-2017-0030450 | 3/2017 |
| KR | 10-1790321 | 10/2017 |
| KR | 10-2018-0047421 | 5/2018 |
| KR | 10-2018-0082710 | 7/2018 |
| KR | 10-1871289 | 8/2018 |
| KR | 10-2019-0063368 | 6/2019 |
| KR | 10-2020-0021075 | 2/2020 |
| KR | 10-2022-0012459 | 2/2022 |
| TW | 1660535 | 5/2019 |
| WO | 2006/098188 | 9/2006 |
| WO | 2017/149636 | 9/2017 |

OTHER PUBLICATIONS

G.A. Kumar et al., "Physical and optical properties of phthalocyanine doped inorganic glasses", Journal of Materials Science 35, 2000, pp. 2539-2542.

Extended European Search Report corresponding with European Patent Application No. 21152336.0 dated on Jun. 11, 2021.

Tobias Schwab et al., "Efficiency enhancement of top-emitting organic light-emitting diodes using conversion dyes", Journal of Applied Physics, Oct. 31, 2011, pp. 1-6, vol. 110, No. 083118.

Third Party Observation for European Patent Application or Patent No. 21152336.0 dated Nov. 30, 2021.

LIGHT EMITTING DIODE AND DISPLAY DEVICE INCLUDING THE SAME

CROSS-REFERENCE TO RELATED APPLICATION(S)

This is a continuation application based on currently pending U.S. patent application Ser. No. 17/153,310, filed on Jan. 20, 2021, the disclosure of which is incorporated herein by reference in its entirety. U.S. patent application Ser. No. 17/153,310 claims priority benefits of Korea Application Nos. 10-2020-0007949 and 10-2020-0176483 under 35 U.S.C. § 119, filed on Jan. 21, 2020 and Dec. 16, 2020, respectively, in the Korean Intellectual Property Office (KIPO), the entire contents of which are incorporated herein by reference.

BACKGROUND

1. Technical Field

The disclosure herein relates to a light emitting diode including multiple hole transport layers having different refractive indexes and a display device including the same.

2. Description of the Related Art

Various display devices used in multimedia apparatuses such as televisions, cellular phones, tablet computers, navigations, and game consoles are being developed. In such a display devices, a so-called self-luminescent display device in which a light emitting material including an organic compound or quantum dots in an emission layer disposed between oppositely disposed electrodes emits light to achieve display, is used.

In the application of a light emitting diode to a display device, the increase of emission efficiency and life of the light emitting diode is required, and development on materials and structures for a light emitting diode stably achieving the requirement is being continuously required.

SUMMARY

The disclosure provides a light emitting diode having excellent light emission efficiency.

The disclosure also provides a display device including a light emitting diode having high emission efficiency.

An embodiment of the inventive concept provides a light emitting diode that may include a first electrode, a hole transport region disposed on the first electrode, an emission layer disposed on the hole transport region, an electron transport region disposed on the emission layer, and a second electrode disposed on the electron transport region. The hole transport region may include a first hole transport layer disposed adjacent to the first electrode, the first hole transport layer having a first refractive index; a second hole transport layer disposed adjacent to the emission layer, the second hole transport layer having a second refractive index; and a third hole transport layer disposed between the first hole transport layer and the second hole transport layer, the third hole transport layer having a third refractive index which is greater than each of the first refractive index and the second refractive index.

In an embodiment, a difference between the third refractive index and the first refractive index may be greater than about 0.1, and a difference between the third refractive index and the second refractive index may be greater than about 0.1.

In an embodiment, the first refractive index and the second refractive index may each be in a range of about 1.30 to about 1.80 at a wavelength of about 460 nm, and the third refractive index may be in a range of about 1.85 to about 2.40 at a wavelength of about 460 nm.

In an embodiment, the first refractive index and the second refractive index may be the same.

In an embodiment, the second hole transport layer may be disposed directly below the emission layer.

In an embodiment, a refractive index of the emission layer may be greater than the second refractive index of the second hole transport layer, and a difference between the refractive index of the emission layer and the second refractive index may be greater than about 0.1 at a wavelength of about 460 nm.

In an embodiment, the refractive index of the emission layer may be in a range of about 1.80 to about 2.40 at a wavelength of about 460 nm.

In an embodiment, the first hole transport layer may be disposed directly above the first electrode.

In an embodiment, a refractive index of the first electrode may be greater than the first refractive index of the first hole transport layer, and a difference between the refractive index of the first electrode and the first refractive index may be greater than about 0.1 at a wavelength of about 460 nm.

In an embodiment, the refractive index of the first electrode may be in a range of about 1.80 to about 2.40 at a wavelength of about 460 nm.

In an embodiment, a thickness ratio of the first hole transport layer, the third hole transport layer, and the second hole transport layer may be in a range of about 0.1:0.8:0.1 to about 0.45:0.1:0.45.

In an embodiment, the first electrode may be a reflective electrode, and the second electrode may be a transmissive electrode or a transflective electrode.

In an embodiment, the emission layer may emit light having a central wavelength in a range of about 430 nm to about 470 nm.

In an embodiment, a thickness of the first hole transport layer may be in a range of about 100 Å to about 1,000 Å, a thickness of the second hole transport layer may be in a range of about 100 Å to about 1,000 Å, and the third hole transport layer may be in a range of about 100 Å to about 1,000 Å.

In an embodiment, the first hole transport layer and the second hole transport layer may each independently include an amine compound represented by Formula 1 below.

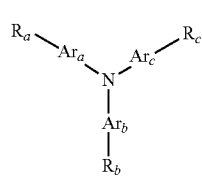

[Formula 1]

In Formula 1, $Ar_a$ to $Ar_c$ may each independently be a substituted or unsubstituted aryl group of 6 to 30 ring-forming carbon atoms, or a substituted or unsubstituted heteroaryl group of 3 to 30 ring-forming carbon atoms, at least two of $R_a$ to $R_c$ may each independently be an adamantyl group or a cyclohexyl group, and the remainder of $R_a$ to $R_c$ may be a hydrogen atom, a deuterium atom, a halogen atom, a cyano group, a substituted or unsubstituted oxy group, a substituted or unsubstituted thio group, a substituted or unsubstituted amine group, or a substituted or unsubstituted alkyl group of 1 to 20 carbon atoms.

In an embodiment, $Ar_a$ to $Ar_c$ may each independently be a substituted or unsubstituted phenyl group, a substituted or unsubstituted naphthyl group, a substituted or unsubstituted biphenyl group, a substituted or unsubstituted terphenyl group, a substituted or unsubstituted fluorenyl group, a substituted or unsubstituted carbazole group, a substituted or unsubstituted dibenzofuranyl group, or a substituted or unsubstituted dibenzothiophenyl group.

In an embodiment, the third hole transport layer may include a compound represented by Formula 2 below.

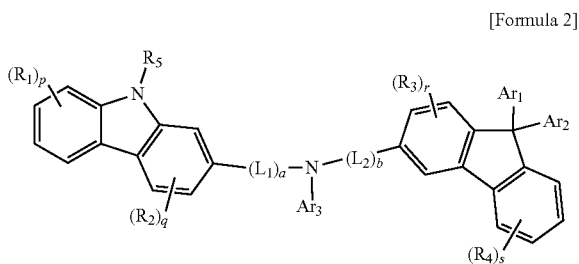

[Formula 2]

In Formula 2, $Ar_1$ and $Ar_2$ may each independently be a hydrogen atom, a deuterium atom, a halogen atom, a substituted or unsubstituted alkyl group of 1 to 30 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring, and $Ar_3$ may be a substituted or unsubstituted aryl group of 6 to 30 ring-forming carbon atoms, or a substituted or unsubstituted heteroaryl group of 2 to 30 ring-forming carbon atoms. In Formula 2, a and b may each independently be 0 or 1, and $L_1$ and $L_2$ may each independently be a substituted or unsubstituted cycloalkylene group of 3 to 10 ring-forming carbon atoms, a substituted or unsubstituted heterocycloalkylene group of 2 to 10 ring-forming carbon atoms, a substituted or unsubstituted cycloalkenylene group of 3 to 10 ring-forming carbon atoms, a substituted or unsubstituted arylene group of 6 to 30 ring-forming carbon atoms, or a substituted or unsubstituted heteroarylene group of 2 to 60 ring-forming carbon atoms. In Formula 2, p and s may each independently be an integer from 0 to 4, q and r may each independently be an integer from 0 to 3, and $R_1$ to $R_5$ may each independently be a hydrogen atom, a deuterium atom, a halogen atom, a hydroxyl group, a cyano group, a nitro group, an amino group, a substituted or unsubstituted silyl group, a substituted or unsubstituted oxy group, a substituted or unsubstituted alkyl group of 1 to 60 carbon atoms, a substituted or unsubstituted heterocycloalkyl group of 3 to 60 ring-forming carbon atoms, a substituted or unsubstituted aryl group of 6 to 60 ring-forming carbon atoms, or a substituted or unsubstituted heteroaryl group of 2 to 60 ring-forming carbon atoms.

In an embodiment, the hole transport region may further include a fourth hole transport layer disposed between the first hole transport layer and the third hole transport layer, the fourth hole transport layer having a refractive index greater than the first refractive index and less than the third refractive index; and a fifth hole transport layer disposed between the second hole transport layer and the third hole transport layer, the fifth hole transport layer having a refractive index greater than the second refractive index and less than the third refractive index.

In an embodiment, the first hole transport layer and the second hole transport layer may each independently include an amine compound represented by Formula 1 above, the third hole transport layer may include a compound represented by Formula 2 above, and the fourth hole transport layer and the fifth hole transport layer may each independently include an amine compound represented by Formula 1 above and a compound represented by Formula 2 above.

In an embodiment, the first to fifth hole transport layers may each have a thickness in a range of about 100 Å to about 1,000 Å.

According to an embodiment of the inventive concept, there is provided a display device including light emitting diodes, each of the light emitting diodes including a first electrode; a hole transport region disposed on the first electrode; an emission layer disposed on the hole transport region; an electron transport region disposed on the emission layer; and a second electrode disposed on the electron transport region. The hole transport region of at least one of the light emitting diodes may include a first hole transport layer disposed adjacent to the first electrode, the first hole transport layer having a first refractive index; a second hole transport layer disposed adjacent to the emission layer, the second hole transport layer having a second refractive index; and a third hole transport layer disposed between the first hole transport layer and the second hole transport layer, the third hole transport layer having a third refractive index which is greater than each of the first refractive index and the second refractive index.

In an embodiment, a difference between the third refractive index and the first refractive index may be greater than about 0.1, and a difference between the third refractive index and the second refractive index may be greater than about 0.1.

In an embodiment, the first electrode may be a reflective electrode, and the second electrode may be a transmissive electrode or a transflective electrode.

BRIEF DESCRIPTION OF THE DRAWINGS

The accompanying drawings are included to provide a further understanding of the inventive concept and are incorporated in and constitute a part of this specification. The drawings illustrate embodiments of the inventive concept and, together with the description, serve to explain principles of the inventive concept. In the drawings.

DETAILED DESCRIPTION OF THE EMBODIMENTS

Figure 1:
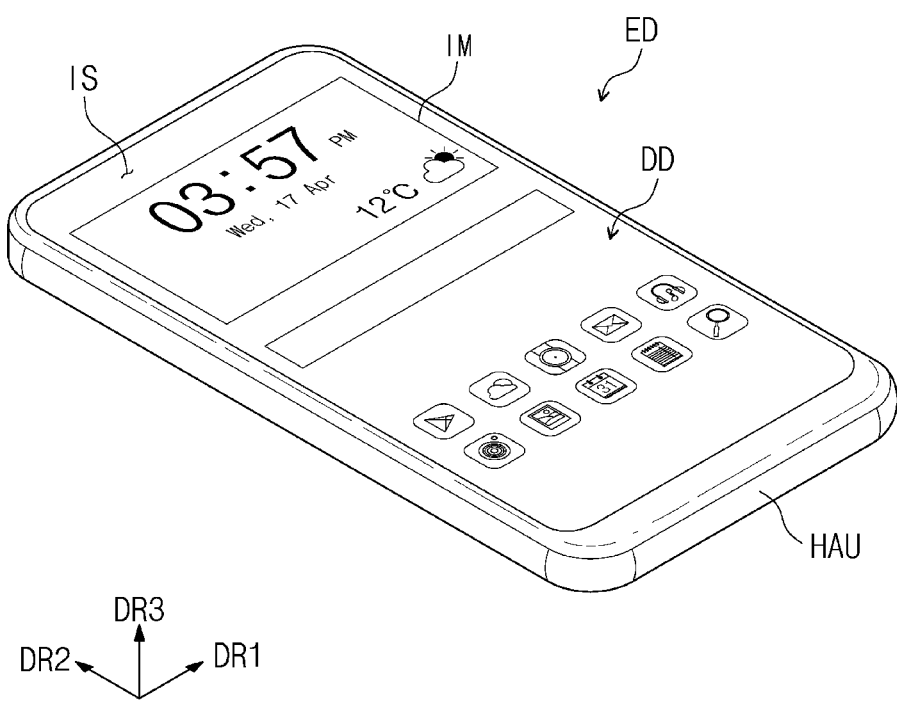
FIG. 1 is a perspective view showing an electronic device according to an embodiment.

The inventive concept may have various modifications and may be embodied in different forms, and embodiments will be explained in detail with reference to the accompany drawings. The inventive concept may, however, be embodied in different forms and should not be construed as limited to the embodiments set forth herein. Rather, all modifications, equivalents, and substituents which are included in the spirit and technical scope of the inventive concept should be included in the inventive concept.

In the description, it will be understood that when an element (or region, layer, part, etc.) is referred to as being "on", "above", "connected to", "coupled to", or "adjacent to" another element, it can be directly on, above, connected to, coupled to, or adjacent to the other element, or one or more intervening elements may be present therebetween.

Like reference numerals refer to like elements throughout the specification. In the drawings, the thickness, the ratio, and the dimensions of constituent elements may be exaggerated for an effective explanation of its technical contents. Therefore, as the sizes and thicknesses of components in the drawings may be arbitrarily illustrated for convenience of explanation, the following embodiments of the disclosure are not limited thereto.

As used herein, the expressions used in the singular such as "a," "an," and "the" are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. For example, a first element could be termed a second element without departing from the teachings of the invention.

Similarly, a second element could be termed a first element without departing from the teachings of the invention.

The terms "below", "beneath", "on" and "above" are used for explaining the relation of elements shown in the drawings. The terms are a relative concept and are explained based on the direction shown in the drawings.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, 10%, or 5% of the stated value.

It will be further understood that the terms "comprises," "comprising," "includes," "including," "have," "having," "contains," "containing," and the like when used in this specification, specify the presence of stated features, numerals, steps, operations, elements, parts, or combinations thereof, but do not preclude the presence or addition of one or more other features, numerals, steps, operations, elements, parts, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

Hereinafter, a light emitting diode and a display device including the same according to an embodiment of the inventive concept will be explained with reference to the accompanying drawings.

Figure 2:
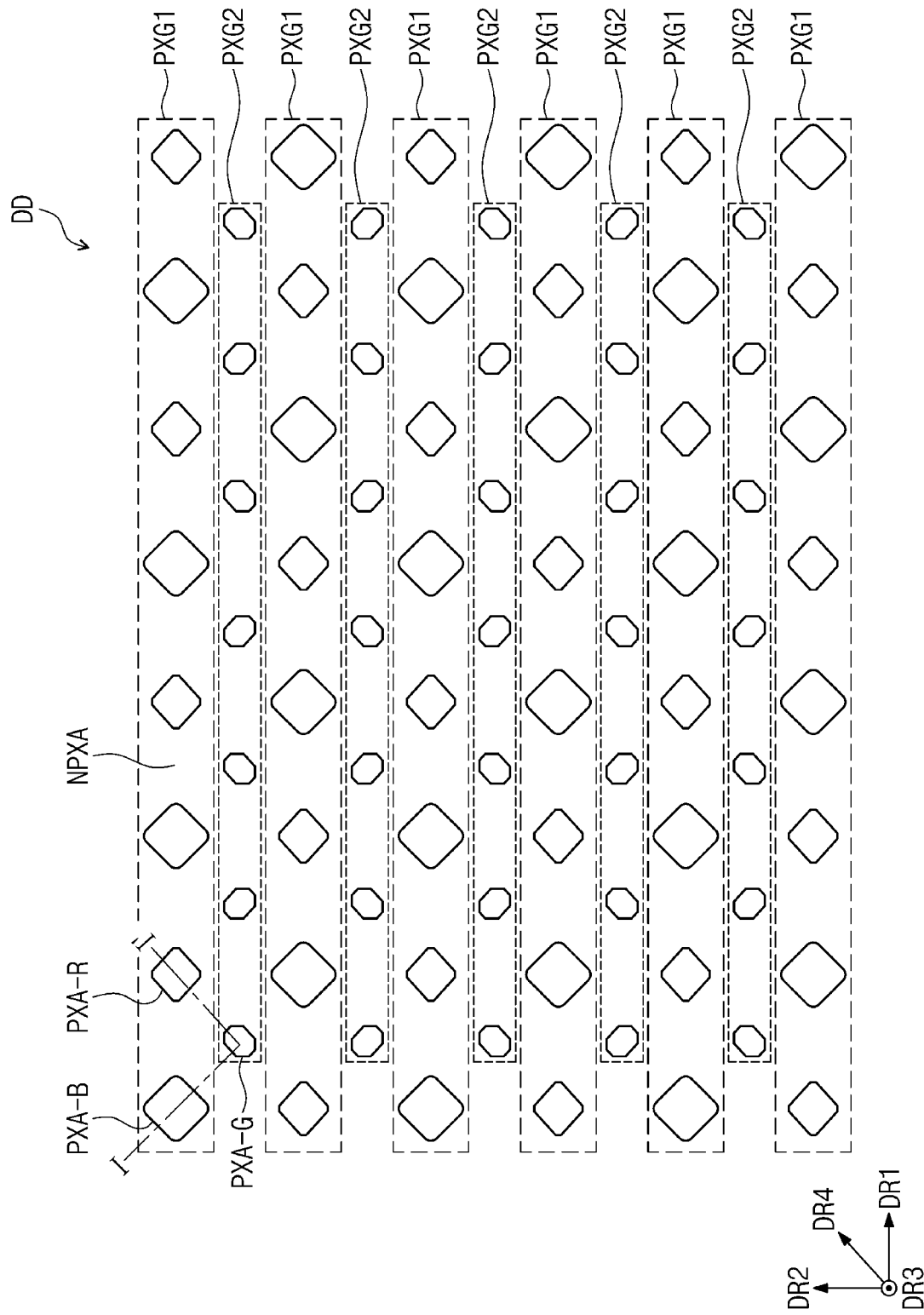
FIG. 2 is a plan view of a display device according to an embodiment.
Figure 3:
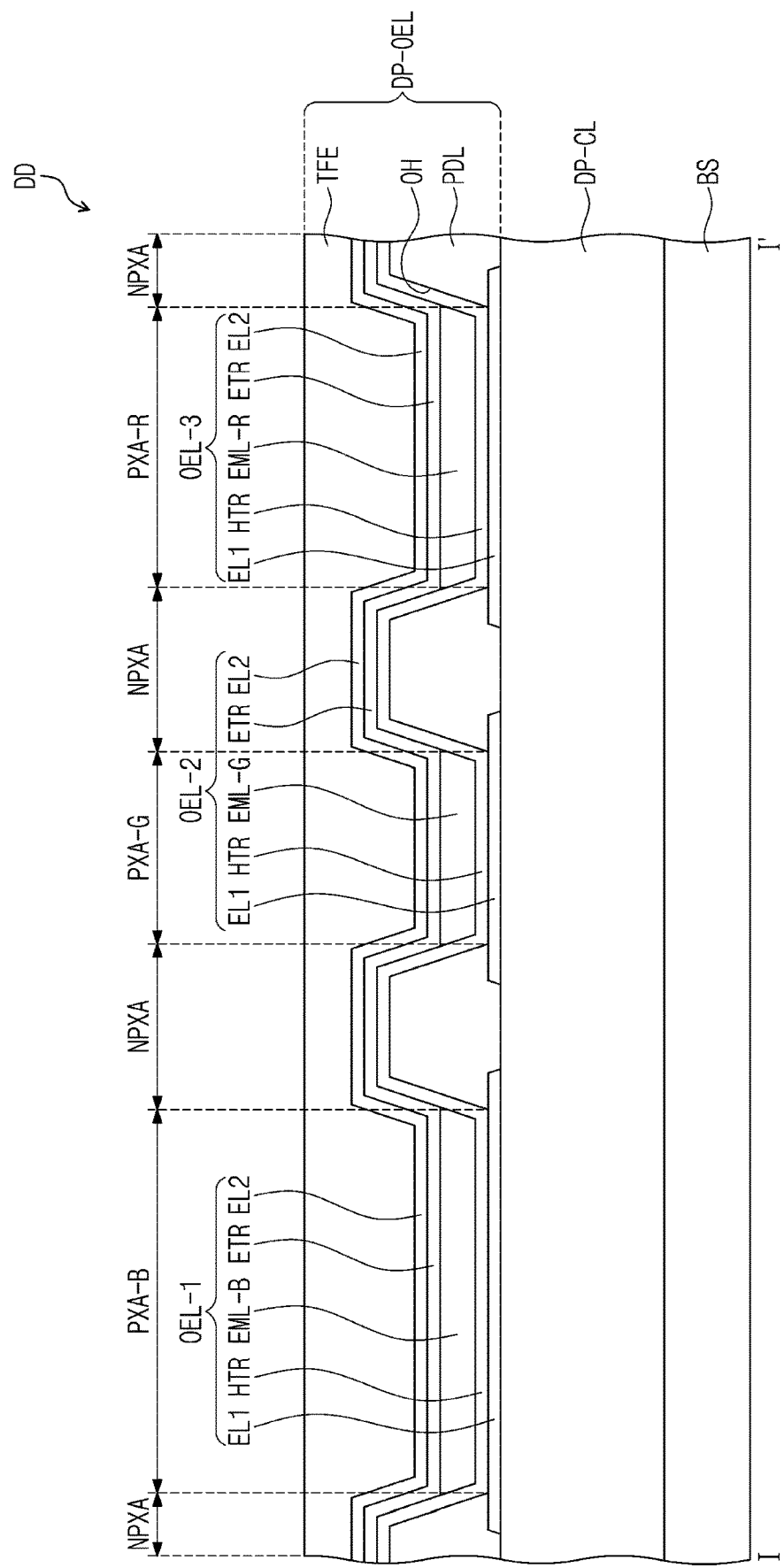
FIG. 3 is a schematic cross-sectional view of a display device of an embodiment, corresponding to line I-I' in FIG. 2.

FIG. 1 is a perspective view showing an embodiment of an electronic device ED. FIG. 2 is a plan view of a display device DD according to an embodiment. FIG. 3 is a schematic cross-sectional view of a display device DD according to an embodiment. FIG. 3 is a schematic cross-sectional view showing a portion corresponding to line I-I' in FIG. 2.

In an embodiment, the electronic device ED may be a small- or medium-sized electronic device such as smart phones, tablets, personal computers, laptop computers, personal digital terminals, car navigation units, game consoles, and cameras. The electronic device ED may be a large-sized electronic device such as televisions, monitors, and external billboards. However, these are only embodiments, and other electronic devices may be employed as long as they do not deviate from the inventive concept.

The electronic device ED may include a display device DD and a housing HAU. The display device DD may display images IM through a display surface IS. In FIG. 1, the display surface IS is shown parallel to a plane defined by a first directional axis DR1 and a second directional axis DR2 crossing the first directional axis DR1. However, this is an illustration, and in other embodiments, the display surface IS of the display device DD may have a bent shape.

Among the directions of the normal line of the display surface IS, i.e., the thickness directions of the display device DD, a direction displaying the images IM is indicated by a third directional axis DR3. The front (or top) and rear (or bottom) of each member may be divided by the third directional axis DR3. The directions indicated by the first to third directional axes DR1, DR2, and DR3 are a relative concept and may be changed into other directions.

The housing HAU may receive the display device DD. The housing HAU may be disposed so as to cover the display device DD and expose the top surface which is the display surface IS of the display device DD. The housing HAU may cover the side and bottom surface of the display device DD while exposing the entire top surface. However, an embodiment of the inventive concept is not limited thereto, and the housing HAU may cover a portion of the top as well as the side and bottom surface of the display device DD.

The display device DD may include a base substrate BS, a circuit layer DP-CL provided on the base substrate BS, and a display device layer DP-OEL. The display device layer DP-OEL may include a pixel defining layer PDL, light emitting diodes OEL-1, OEL-2, and OEL-3 disposed in the pixel defining layer PDL, and an encapsulating layer TFE disposed on the light emitting diodes OEL-1, OEL-2, and OEL-3.

The base substrate BS may be a member providing a base surface where the display device layer DP-OEL is disposed. The base substrate BS may be a glass substrate, a metal substrate, a plastic substrate, etc. However, an embodiment of the inventive concept is not limited thereto, and the base substrate BS may be an inorganic layer, an organic layer, or a composite material layer.

In an embodiment, the circuit layer DP-CL is disposed on the base substrate BS, and the circuit layer DP-CL may include multiple transistors (not shown). Each of the transistors (not shown) may include a control electrode, an input electrode, and an output electrode. For example, the circuit layer DP-CL may include switching transistors and driving transistors for driving the light emitting diodes OEL-1, OEL-2, and OEL-3 of the display device layer DP-OEL.

Each of the light emitting diodes OEL-1, OEL-2, and OEL-3 may include a first electrode EL1, a hole transport region HTR, emission layers EML-B, EML-G, and EML-R, an electron transport region ETR and a second electrode EL2. Each of the light emitting diodes OEL-1, OEL-2, and OEL-3 included in the display device DD of an embodiment may have the structure of a light emitting diode OEL of an embodiment (FIG. 4), which will be explained later. The hole transport region HTR included in each of the light emitting diodes OEL-1, OEL-2, and OEL-3 included in the display device DD of an embodiment may include hole transport layers having refractive index values different from each other.

In FIG. 3, an embodiment is shown where the emission layers EML-B, EML-G, and EML-R of light emitting diodes OEL-1, OEL-2, and OEL-3, which are in opening portions OH defined in a pixel defining layer PDL, are disposed, and a hole transport region HTR, an electron transport region ETR and a second electrode EL2 are provided as common layers in all light emitting diodes OEL-1, OEL-2, and OEL-3. However, an embodiment of the inventive concept is not limited thereto. In contrast to FIG. 3, in an embodiment, the hole transport region HTR or the electron transport region ETR may be divided by the pixel defining layer PDL and may be patterned and provided in the opening portions OH defined in the pixel defining layer PDL.

In an embodiment, the hole transport region HTR, the emission layers EML-B, EML-G, and EML-R, and the electron transport region ETR of the light emitting diodes OEL-1, OEL-2, and OEL-3 may be provided by using various methods such as a vacuum deposition method, a spin coating method, a cast method, a Langmir-Blodgett (LB) method, an ink jet printing method, a laser printing method, and a laser induced thermal imaging (LITI) method.

The encapsulating layer TFE may cover the light emitting diodes OEL-1, OEL-2, and OEL-3. The encapsulating layer TFE may encapsulate the display device layer DP-OEL. The encapsulating layer TFE may be disposed on the second electrode EL2 and may be disposed while filling up the opening portion OH.

The encapsulating layer TFE may be a thin film encapsulating layer. The encapsulating layer TFE may be one layer or a stack of multiple layers. The encapsulating layer TFE may include at least one insulating layer. The encapsulating layer TFE according to an embodiment may include at least one inorganic layer (hereinafter, encapsulating inorganic layer). The encapsulating layer TFE according to an embodiment of the inventive concept may include at least one organic layer (hereinafter, encapsulating organic layer) and at least one encapsulating inorganic layer.

The encapsulating inorganic layer protects the display device layer DP-OEL from moisture and/or oxygen, and the encapsulating organic layer protects the display device layer DP-OEL from foreign materials such as dust particles. The encapsulating inorganic layer may include a silicon nitride layer, a silicon oxy nitride layer, a silicon oxide layer, a titanium oxide layer, or an aluminum oxide layer, without specific limitation. The encapsulating organic layer may include an acrylic organic layer, without specific limitation.

Although not shown in the drawings, a capping layer (not shown) may be further disposed on the second electrode EL2. For example, the capping layer (not shown) may be disposed between the second electrode EL2 and the encapsulating layer TFE.

Referring to FIG. 2 and FIG. 3, the display device DD may include a non-light emitting region NPXA and light emitting regions PXA-B, PXA-G, and PXA-R. The light emitting regions PXA-B, PXA-G, and PXA-R may be areas emitting light produced from the light emitting diodes OEL-1, OEL-2, and OEL-3, respectively. The light emitting regions PXA-B, PXA-G, and PXA-R may be separated from each other on a plane.

The light emitting regions PXA-B, PXA-G, and PXA-R may be areas separated by the pixel defining layer PDL. The non-light emitting regions NPXA may be areas between neighboring light emitting regions PXA-B, PXA-G, and PXA-R and may be areas corresponding to the pixel defining layer PDL. In the disclosure, each of the light emitting regions PXA-B, PXA-G, and PXA-R may correspond to each pixel. The pixel defining layer PDL may divide the light emitting diodes OEL-1, OEL-2, and OEL-3. The emission layers EML-B, EML-G, and EML-R of the light emitting diodes OEL-1, OEL-2, and OEL-3 may be disposed and divided in the opening portions OH defined in the pixel defining layer PDL. The emission layers EML-B, EML-G, and EML-R defined by the pixel defining layer PDL may be formed by an ink jet printing method, etc.

The pixel defining layer PDL may be formed using a polymer resin. For example, the pixel defining layer PDL may be formed by including a polyacrylate-based resin or a polyimide-based resin. The pixel defining layer PDL may be formed by further including an inorganic material in addition to the polymer resin. The pixel defining layer PDL may be formed by including a light-absorbing material, or by including a black pigment or a black dye. The pixel defining layer PDL formed by including the black pigment or the black dye may form a black pixel defining layer. During forming the pixel defining layer PDL, carbon black may be used as the black pigment or the black dye, but an embodiment of the inventive concept is not limited thereto.

The pixel defining layer PDL may be formed using an inorganic material. For example, the pixel defining layer PDL may be formed by including silicon nitride ($SiN_x$), silicon oxide ($SiO_x$), silicon oxynitride ($SiO_xN_y$), etc. The pixel defining layer PDL may define the light emitting regions PXA-B, PXA-G, and PXA-R. The light emitting regions PXA-B, PXA-G, and PXA-R and the non-light emitting region NPXA may be defined by the pixel defining layer PDL.

The light emitting regions PXA-B, PXA-G, and PXA-R may be divided into multiple groups according to the color of light produced from the light emitting diodes OEL-1, OEL-2, and OEL-3. In the display device DD of an embodiment, shown in FIG. 2 and FIG. 3, three light emitting regions PXA-B, PXA-G, and PXA-R emitting blue light, green light, and red light are illustrated as an embodiment. For example, the display device DD of an embodiment may include a red light emitting region PXA-R, a green light emitting region PXA-G, and a blue light emitting region PXA-B, which are separated from each other.

The display device DD according to an embodiment includes multiple light emitting diodes OEL-1, OEL-2, and OEL-3, and the multiple light emitting diodes OEL-1, OEL-2, and OEL-3 may emit light having different wavelength regions. For example, in an embodiment, the display device DD may include a first light emitting diode OEL-1 emitting blue light, a second light emitting diode OEL-2 emitting green light, and a third light emitting diode OEL-3 emitting red light. However, an embodiment of the inventive concept is not limited thereto, and the first to third light emitting diodes OEL-1, OEL-2 and OEL-3 may emit light in the same wavelength region, or at least one thereof may emit light in a different wavelength region. For example, the blue light emitting region PXA-B, the green light emitting region PXA-G, and the red light emitting region PXA-R may correspond to the first light emitting diode OEL-1, the second light emitting diode OEL-2, and the third light emitting diode OEL-3, respectively.

In an embodiment, all the first to third light emitting diodes OEL-1, OEL-2, and OEL-3 may emit light in a blue wavelength region. The display device DD may further include a color controlling layer on the display device layer DP-OEL. The color controlling layer may be a part transmitting light or converting the wavelength of light provided from the first to third light emitting diodes OEL-1, OEL-2, and OEL-3.

Referring to FIG. 2, the blue light emitting region PXA-B and the red light emitting region PXA-R may be alternately arranged along the first directional axis DR1 to from a first group PXG1. The green light emitting regions PXA-G may be arranged along the first directional axis DR1 to form a second group PXG2. The first group PXG1 may be separately disposed from the second group PXG2 in the second directional axis DR2. Each of the first group PXG1 and the second group PXG2 may be provided in numbers. The first groups PXG1 and the second groups PXG2 may be alternately arranged along the second directional axis DR2.

One green light emitting region PXA-G may be separately disposed from one blue light emitting region PXA-B or one red light emitting region PXA-R in a fourth directional axis DR4. The fourth directional axis DR4 may be a direction between the direction of the first directional axis DR1 and the direction of the second directional axis DR2.

The arrangement structure of the light emitting regions PXA-B, PXA-G, and PXA-R shown in FIG. 2 may be referred to as a pentile structure. However, the arrangement structure of the light emitting regions PXA-B, PXA-G, and PXA-R in the display device DD according to an embodiment is not limited to the arrangement structure shown in FIG. 2. For example, the light emitting regions PXA-B, PXA-G, and PXA-R in an embodiment may have a stripe structure in which the blue light emitting region PXA-B, the green light emitting region PXA-G, and the red light emitting region PXA-R are arranged by turns along the first directional axis DR1.

Figure 4:
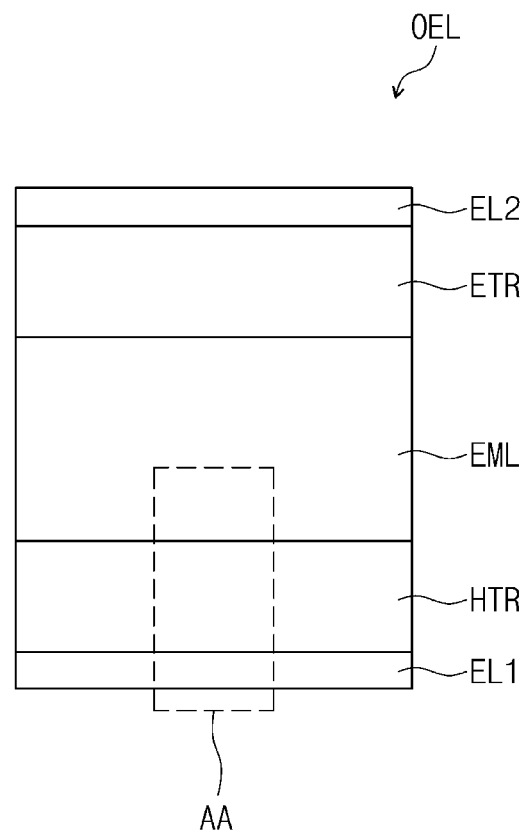
FIG. 4 is a schematic cross-sectional view of a light emitting diode of an embodiment.
Figure 5:
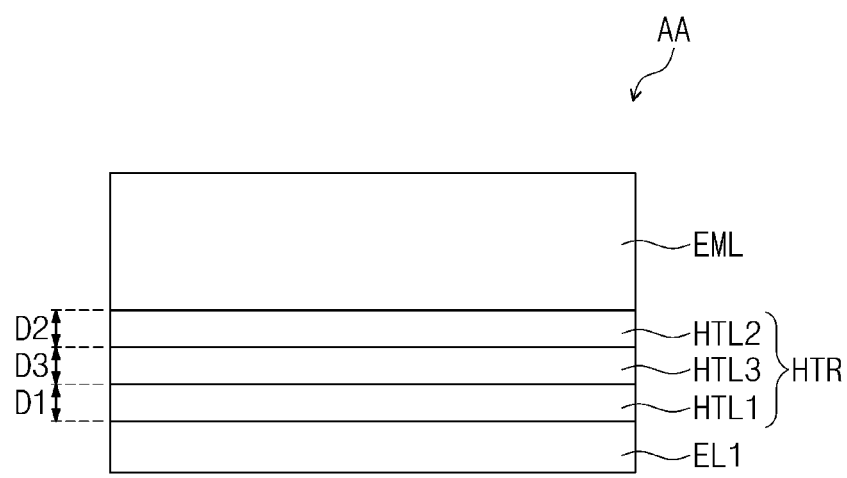
FIG. 5 is a schematic cross-sectional view of a portion of a light emitting diode according to an embodiment.

FIG. 4 is schematic cross-sectional view showing a light emitting diode of an embodiment. FIG. 5 is a schematic cross-sectional view showing a portion of the light emitting diode according to an embodiment. FIG. 5 is a schematic cross-sectional view showing a portion corresponding to region AA in FIG. 4. As described above, each of multiple light emitting diodes OEL-1, OEL-2, and OEL-3 included in the display device DD shown in FIG. 3, etc., may have the structure of the light emitting diode OEL shown in FIG. 4 and FIG. 5.

The light emitting diode OEL of an embodiment includes a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. In the light emitting diode OEL of an embodiment, the hole transport region may include a first hole transport layer HTL1 disposed adjacent to the first electrode EL1, a second hole transport layer HTL2 disposed adjacent to the emission layer EML, and a third hole transport layer HTL3 disposed between the first hole transport layer HTL1 and the second hole transport layer HTL2.

In an embodiment, the first hole transport layer HTL1 and the second hole transport layer HTL2 may be layers having lower refractive indexes than the third hole transport layer HTL3. The first refractive index of the first hole transport layer HTL1 may be less than the third refractive index of the third hole transport layer HTL3, and the second refractive index of the second hole transport layer HTL2 may be less than the third refractive index of the third hole transport layer HTL3.

In the light emitting diode OEL of an embodiment, the first electrode EL1 has conductivity. The first electrode EL1 may be formed using a metal alloy or a conductive compound. The first electrode EL1 may be an anode. The first electrode EL1 may be a pixel electrode. The first electrode EL1 may be a reflective electrode. If the first electrode EL1 is the reflective electrode, the first electrode EL1 may include Ag, Mg, Cu, Al, Pt, Pd, Au, Ni, Nd, Ir, Cr, $L_1$, Ca, LiF/Ca, LiF/Al, Mo, Ti, compounds thereof, or mixtures thereof (for example, a mixture of Ag and Mg). In an embodiment, the first electrode EL1 may have a stacked structure of multiple layers. If the first electrode EL1 has the stacked structure of multiple layers, at least one layer may be a reflective layer formed using the reflective electrode material. If the first electrode EL1 has the stacked structure of multiple layers, at least one layer may include a transparent conductive layer formed by using indium tin oxide (ITO), indium zinc oxide (IZO), zinc oxide (ZnO), indium tin zinc oxide (ITZO), etc. For example, the first electrode EL1 may have a three-layer structure of ITO/Ag/ITO. However, an embodiment of the inventive concept is not limited thereto. A thickness of the first electrode EL1 may be in a range of about 1,000 Å to about 10,000 Å. For example, the thickness of the first electrode EL1 may be in a range of about 1,000 Å to about 3,000 Å.

The hole transport region HTR is provided on the first electrode EL1. The hole transport region HTR may include the first to third hole transport layers HTL1, HTL2, and HTL3. Based on the third hole transport layer HTL3 which has a relatively higher refractive index than the other hole transport layers HTL1 and HTL2, the first hole transport layer HTL1 may be disposed below the third hole transport layer HTL3, and the second hole transport layer HTL2 may be disposed above the third hole transport layer HTL3. In the light emitting diode OEL of an embodiment, the hole transport region HTR may include multiple hole transport layers HTL1, HTL2, and HTL3 disposed in the order of hole transport layer of a low refractive index/hole transport layer of a high refractive index/hole transport layer of a low refractive index in a thickness direction.

At a wavelength of about 460 nm, a difference between the third refractive index of the third hole transport layer HTL3 and the first refractive index of the first hole transport layer HTL1 may be greater than about 0.1. For example, at about 460 nm, the difference between the third refractive index and the first refractive index may be equal to or greater than about 0.2. At a wavelength of about 460 nm, a difference between the third refractive index of the third hole transport layer HTL3 and the second refractive index of the second hole transport layer HTL2 may be greater than about 0.1. For example, at about 460 nm, the difference between the third refractive index and the second refractive index may be equal to or greater than about 0.2.

At a wavelength of about 460 nm, the first refractive index of the first hole transport layer HTL1 and the second refractive index of the second hole transport layer HTL2 may each be in a range of about 1.30 to about 1.80. At a wavelength of about 460 nm, the third refractive index of the third hole transport layer HTL3 may be in a range of about 1.85 to about 2.40. For example, the first refractive index and the second refractive index of the second hole transport layer HTL2 may each be in a range of about 1.40 to about 1.60, and the third refractive index of the third hole transport layer HTL3 may be in a range of about 1.90 to about 2.00.

A thickness of the hole transport region HTR may be in a range of about 300 Å to about 15,000 Å. For example, the thickness of the hole transport region HTR may be in a range of about 300 Å to about 5,000 Å. Thicknesses D1, D2, and D3 of the first to third hole transport layers HTL1, HTL2, and HTL3, respectively, that are included in the hole transport region HTR may each be in a range of about 100 Å to about 1,000 Å.

The thickness ratio (D1:D3:D2) of the first to third hole transport layers HTL1, HTL3, and HTL2 included in the hole transport region HTR may be in a range of about 0.1:0.8:0.1 to about 0.45:0.1:0.45. For example, in an embodiment, the thickness D1 of the first hole transport layer and the thickness D2 of the second hole transport layer may be substantially the same, and the thickness D3 of the third hole transport layer may be different from the thickness D1 of the first hole transport layer and the thickness D2 of the second hole transport layer. However, an embodiment of the inventive concept is not limited thereto, and the thickness D1 of the first hole transport layer and the thickness D2 of the second hole transport layer may be different from each other. The thickness ratio (D1:D3:D2) of the first to third hole transport layers HTL1, HTL3, and HTL2 may be controlled to an optimum range according to the wavelength region of light emitted from the emission layer EML, display quality required for the display device DD (FIG. 2), and the type of the hole transport materials used in each of the hole transport layers HTL1, HTL2, and HTL3 of the hole transport region HTR.

For example, in a case where blue light having a central wavelength in a wavelength region in a range of about 430 nm to about 470 nm is emitted from the emission layer EML in the light emitting diode OEL of an embodiment, the thickness ratio (D1:D3:D2) of the first to third hole transport layers HTL1, HTL3, and HTL2 may be about 1:1:1.

The light emitting diode OEL of an embodiment may include multiple hole transport layers HTL1, HTL2, and HTL3 disposed in the order of hole transport layer of a low refractive index/hole transport layer of a high refractive index/hole transport layer of a low refractive index, to show improved emission efficiency properties. The light emitting diode OEL of an embodiment includes the hole transport layers HTL1, HTL2, and HTL3 of the hole transport region HTR, having refractive index differences, and may minimize the extinction of light emitted from inner functional layers through destructive interference and induce constructive interference by the hole transport layers HTL1, HTL2, and HTL3 having refractive index differences, thereby showing high light emission efficiency.

In an embodiment, the first hole transport layer HTL1 may be disposed just above the first electrode EL1. For example, the first hole transport layer HTL1 may be disposed directly above the first electrode EL1. The second hole transport layer HTL2 may be disposed just below the emission layer EML. For example, the second hole transport layer HTL2 may be disposed directly below the emission layer EML.

In the description, "disposed just" may mean that no additional layer, film, region, plate, or the like is present between a layer, a film, a region, a plate, or the like and another. For example, one element may be disposed directly on another element. For example, "disposed just" means two layers are disposed without using an additional member such as an adhesive member between the two layers.

In the light emitting diode OEL of an embodiment, at a wavelength of about 460 nm, the refractive index of the first electrode EL1 may be in a range of about 1.80 to about 2.40. For example, the refractive index of the first electrode EL1 may be in a range of about 1.90 to about 2.00. For example, the refractive index of the first electrode EL1 may be greater than the first refractive index of the first hole transport layer HTL1, and a refractive index difference between the adjacent first hole transport layer HTL1 and first electrode EL1 at about 460 nm may be greater than about 0.1.

In the light emitting diode OEL of an embodiment, at a wavelength of about 460 nm, the refractive index of the emission layer EML may be in a range of about 1.80 to about 2.40. For example, the refractive index of the emission layer EML may be in a range of about 1.90 to about 2.00. For example, the refractive index of the emission layer EML may be greater than the second refractive index of the second hole transport layer, and a refractive index difference between the adjacent second hole transport layer HTL2 and emission layer EML at about 460 nm may be greater than about 0.1.

For example, the light emitting diode OEL of an embodiment includes the hole transport region HTR in which hole transport layers HTL1 and HTL2 having refractive index differences from adjacent first electrode EL1 and emission layer EML, and may show high light extraction efficiency properties and improved emission efficiency properties.

The first hole transport layer HTL1 and the second hole transport layer HTL2 may each independently include an amine compound represented by Formula 1 below. The amine compound represented by Formula 1 may have a refractive index value in a range of about 1.30 to about 1.80 at a wavelength of about 460 nm. The first hole transport layer HTL1 and the second hole transport layer HTL2 may be each independently formed using any one among the amine compounds represented by Formula 1 below or mixtures thereof.

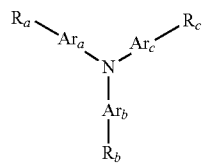

[Formula 1]

In Formula 1, $Ar_a$ to $Ar_c$ may be each independently a substituted or unsubstituted aryl group of 6 to 30 ring-forming carbon atoms, or a substituted or unsubstituted heteroaryl group of 3 to 30 ring-forming carbon atoms. At least two of $R_a$ to $R_c$ may each independently be an adamantyl group or a cyclohexyl group, and the remainder of $R_a$ to $R_c$ may be a hydrogen atom, a deuterium atom, a halogen atom, a cyano group, a substituted or unsubstituted oxy group, a substituted or unsubstituted thio group, a substituted or unsubstituted amine group, or a substituted or unsubstituted alkyl group of 1 to 20 carbon atoms.

In the amine compound represented by Formula 1, $Ar_a$ to $Ar_c$ may each independently be a substituted or unsubstituted phenyl group, a substituted or unsubstituted naphthyl group, a substituted or unsubstituted biphenyl group, a substituted or unsubstituted terphenyl group, a substituted or unsubstituted fluorenyl group, a substituted or unsubstituted carbazole group, a substituted or unsubstituted dibenzofuranyl group, or a substituted or unsubstituted dibenzothiophenyl group. However, an embodiment of the inventive concept is not limited thereto.

Two selected among $R_a$ to $R_c$, or $R_a$ to $R_c$ may be each independently an unsubstituted adamantyl group, or an unsubstituted cyclohexyl group. For example, two selected among $R_a$ to $R_c$ may be adamantyl groups, or two of $R_a$ to $R_c$ may be cyclohexyl groups. In another embodiment, one of the two selected among $R_a$ to $R_c$ may be an adamantyl group, and the remainder may be a cyclohexyl group.

In an embodiment, all of $R_a$ to $R_c$ may be adamantyl groups or cyclohexyl groups. Two selected among $R_a$ to $R_c$ may be adamantyl groups, and the remainder of $R_a$ to $R_c$ may be a cyclohexyl group, or two selected among $R_a$ to $R_c$ may be cyclohexyl groups, and the remainder may be an adamantyl group.

In an embodiment, the first hole transport layer and the second hole transport layer may each independently include at least one among the amine compounds represented in Compound Group 1 below.

[Compound Group 1]

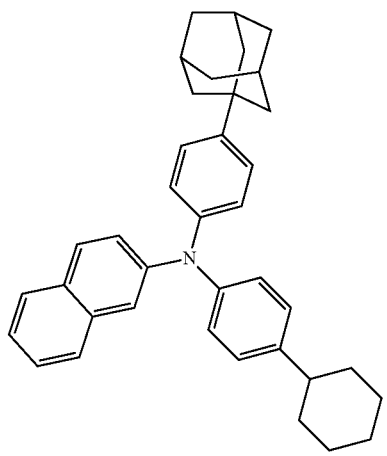

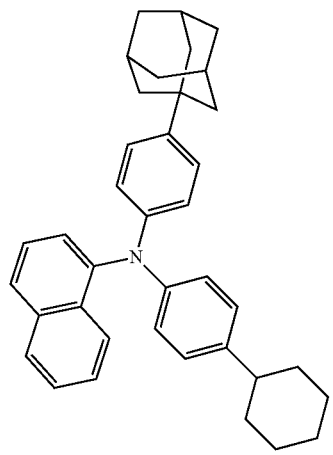

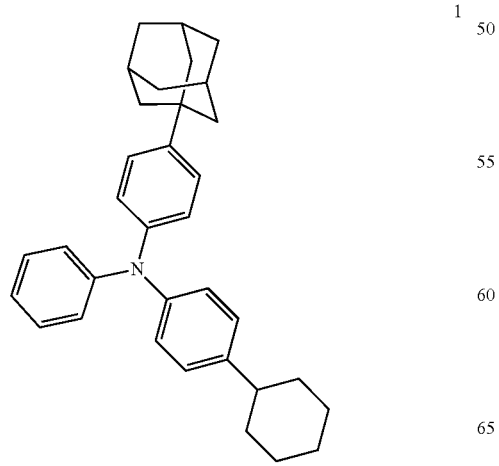

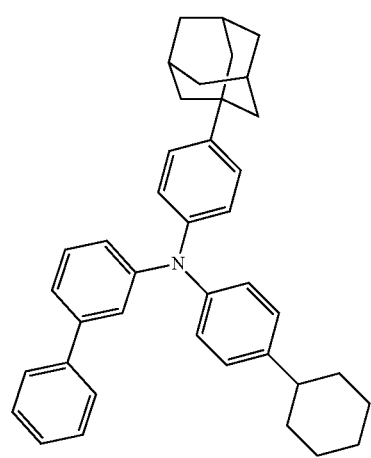
5
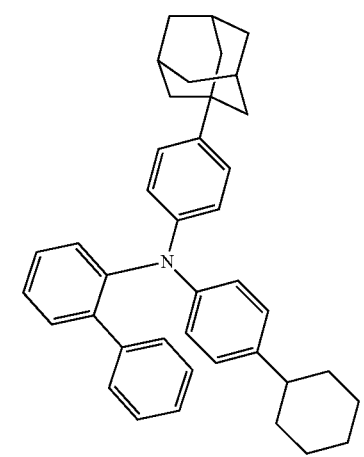
6
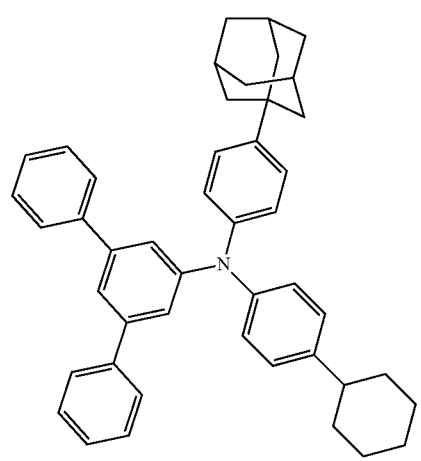
7
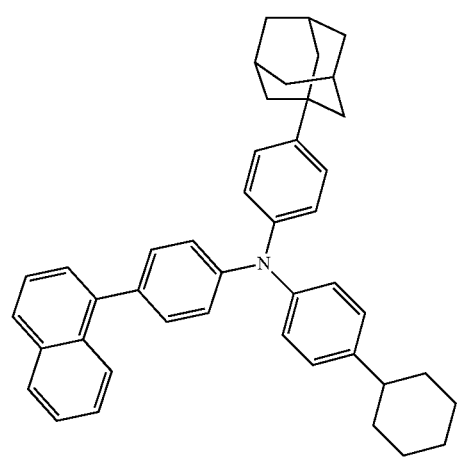
8
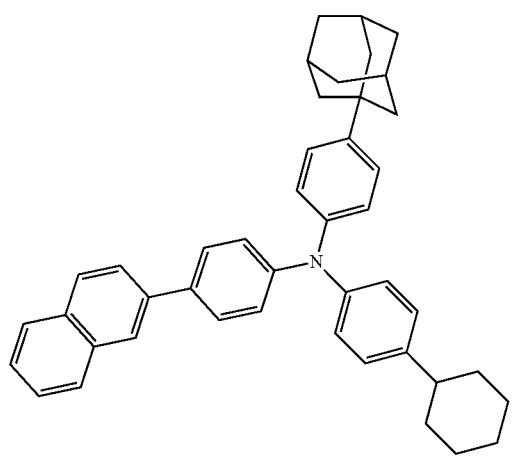
9
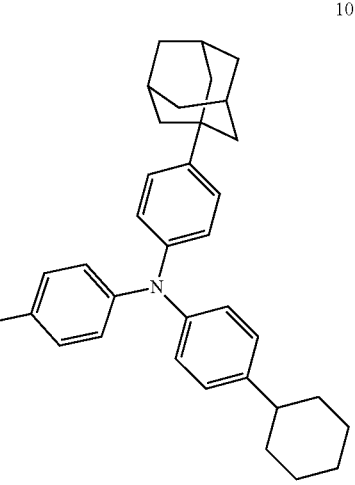
10

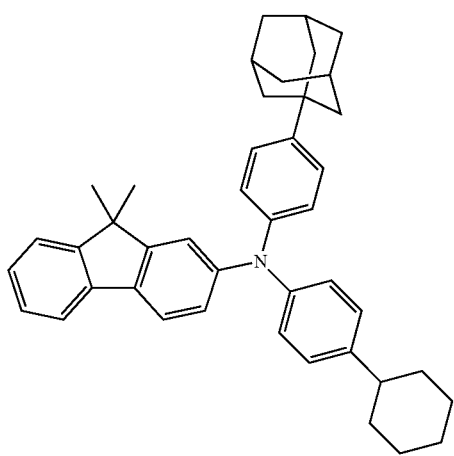 11
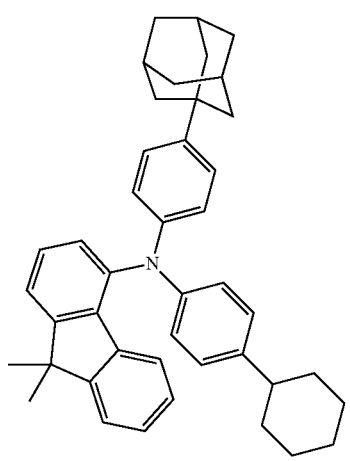 14
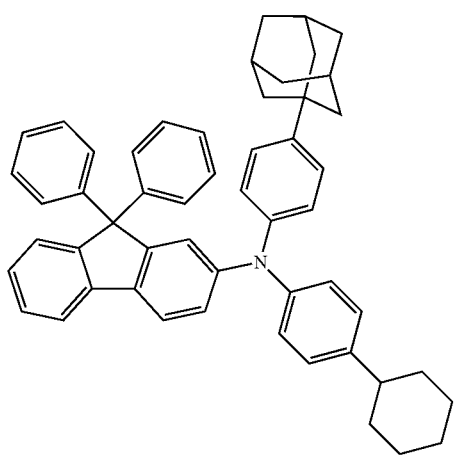 12
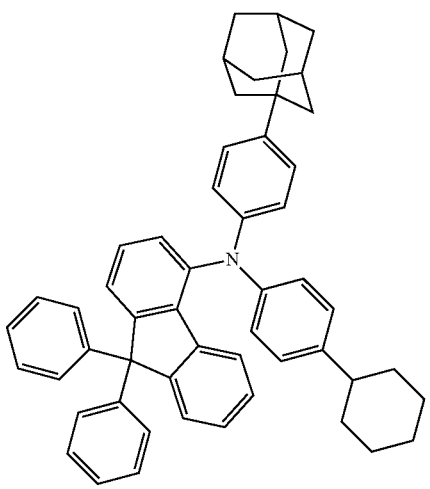 15
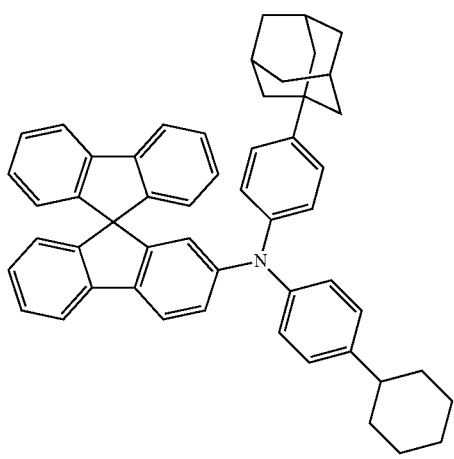 13
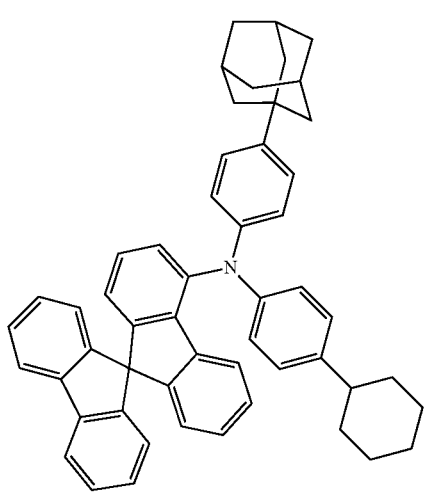 16

17
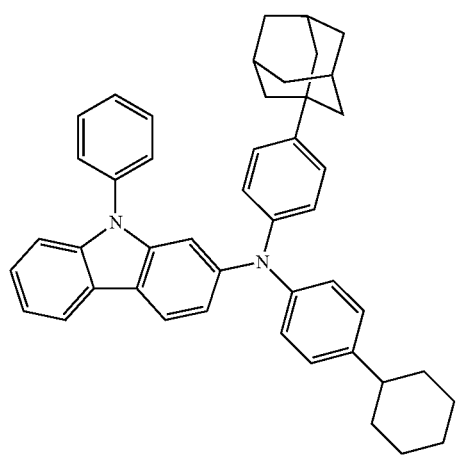
18
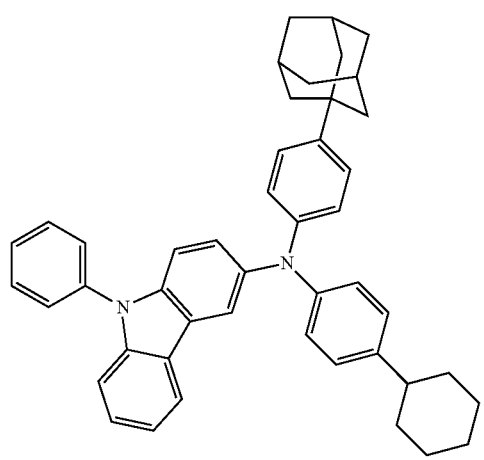
19
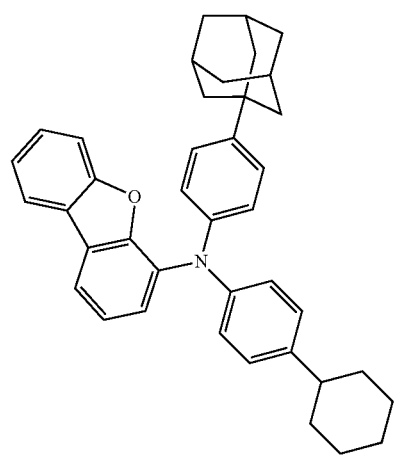
20
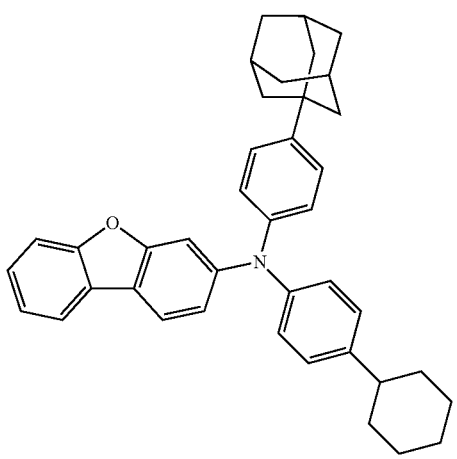
21
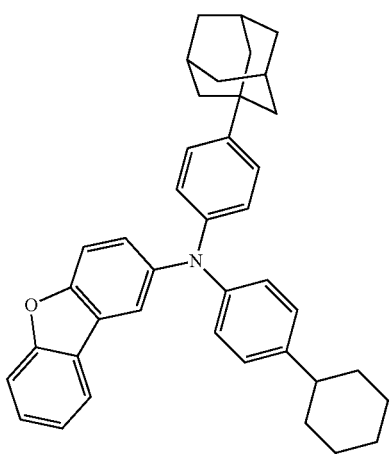
22
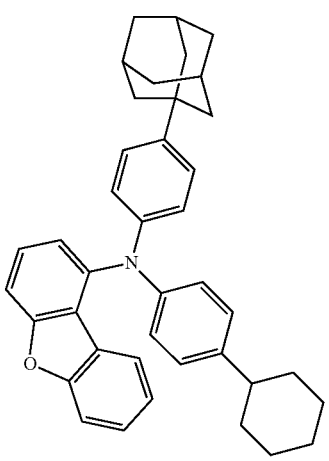

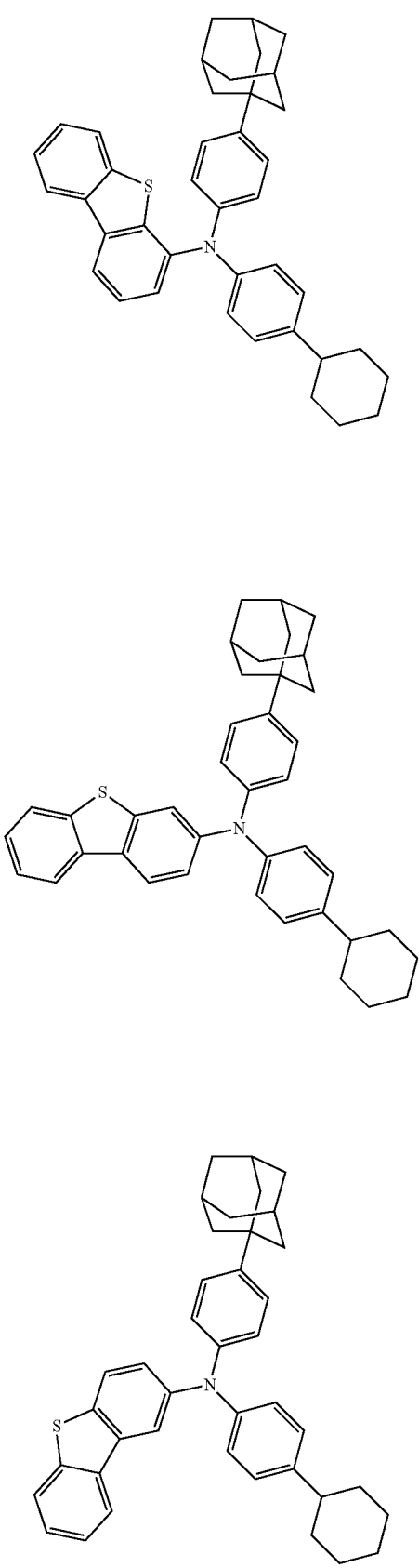
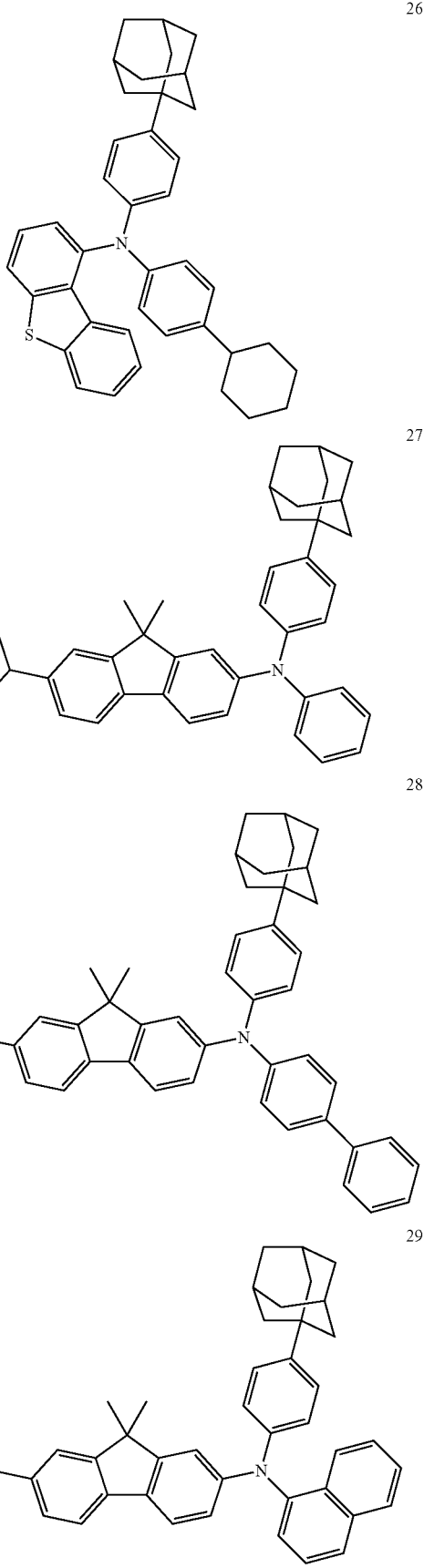

30
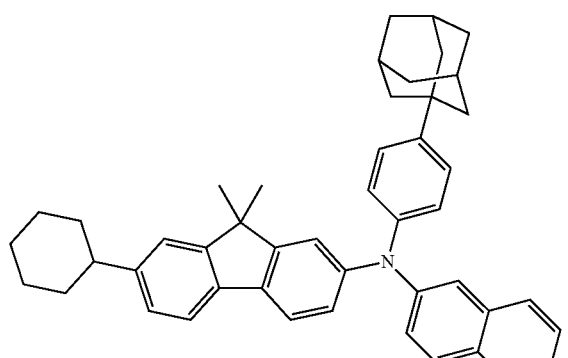
31
32
33
34
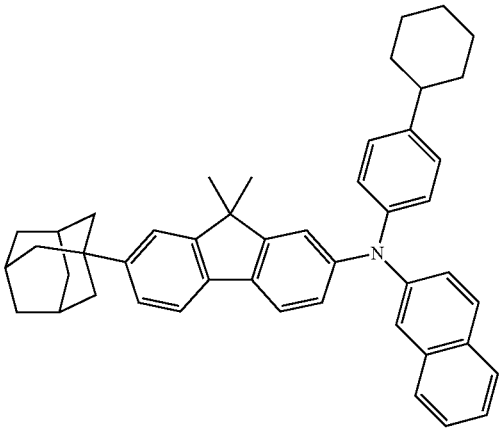
35
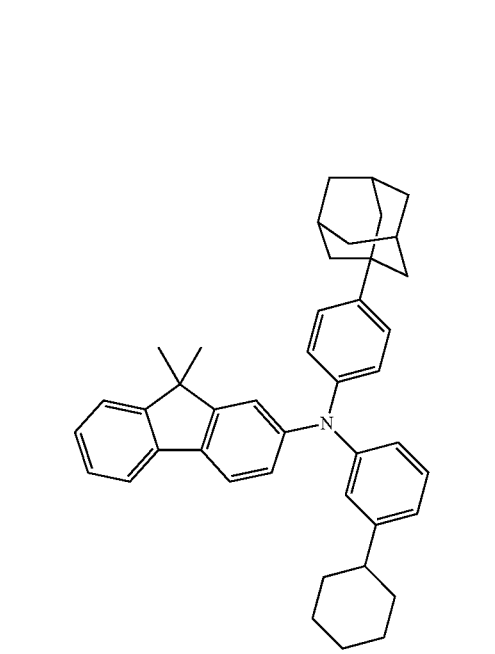
36
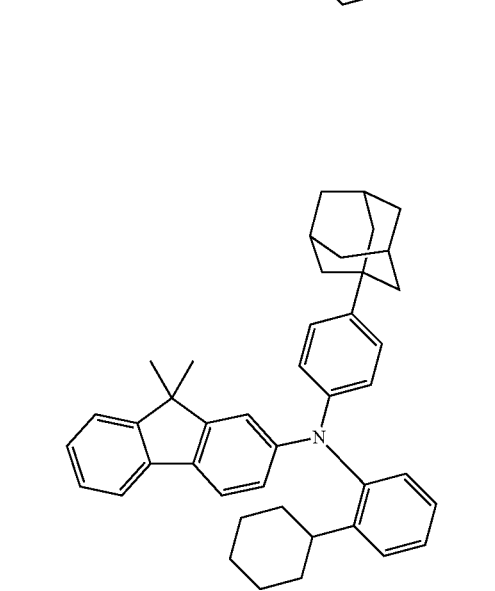

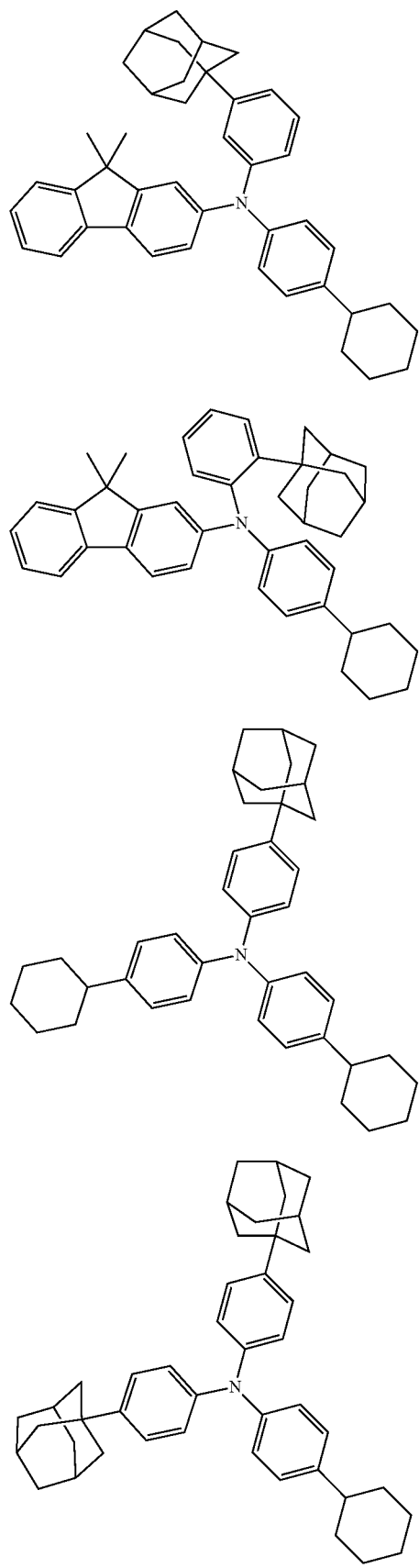
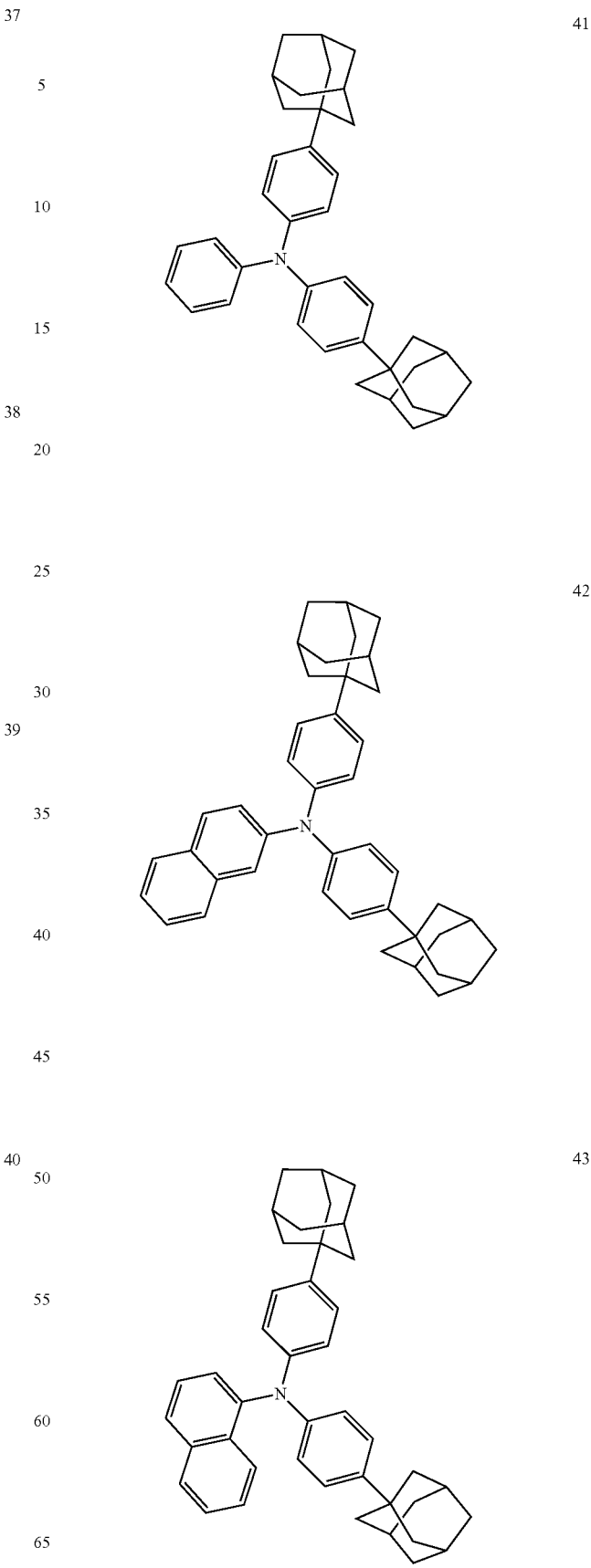

44
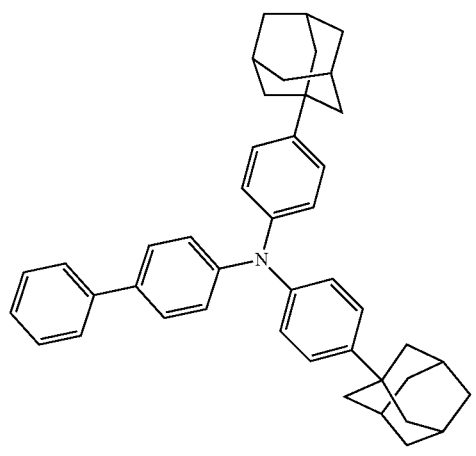
45
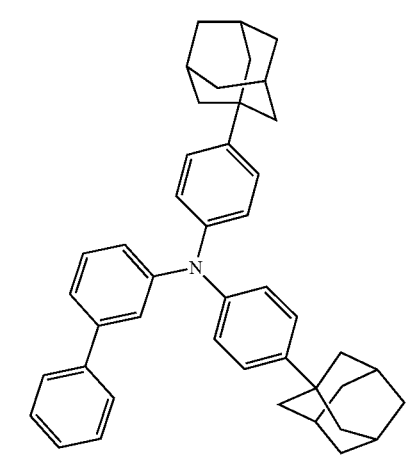
46
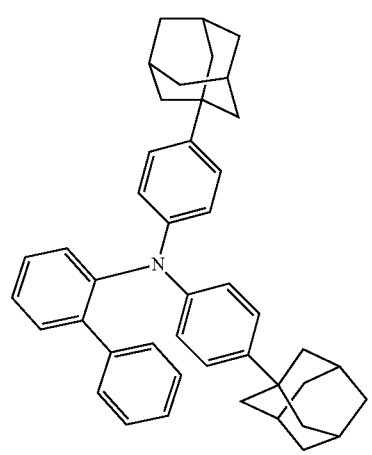
47
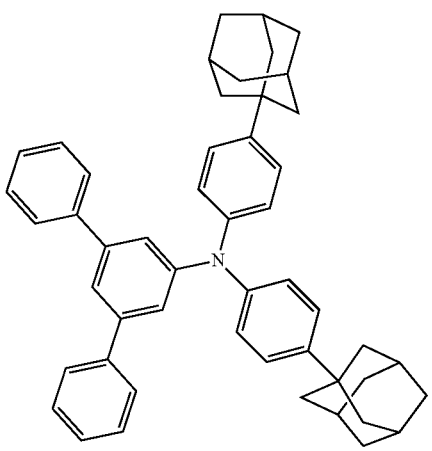
48
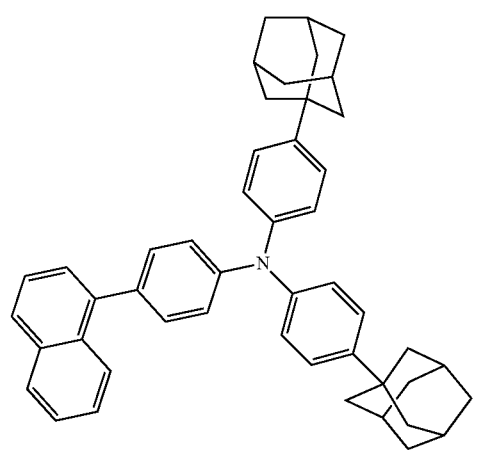
49
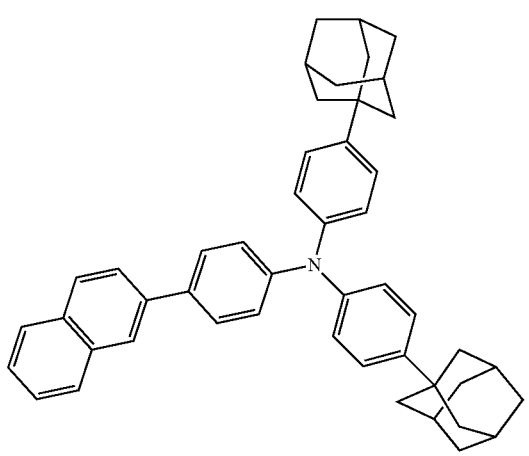

50
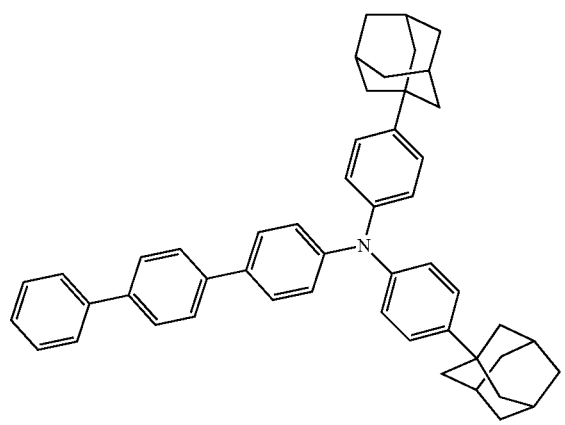
51
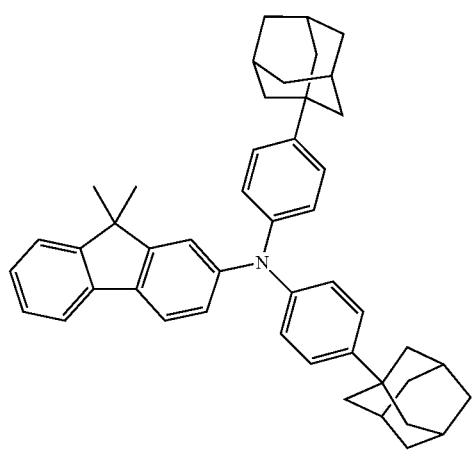
52
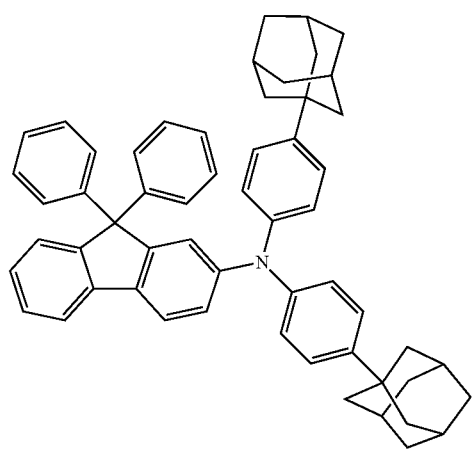
53
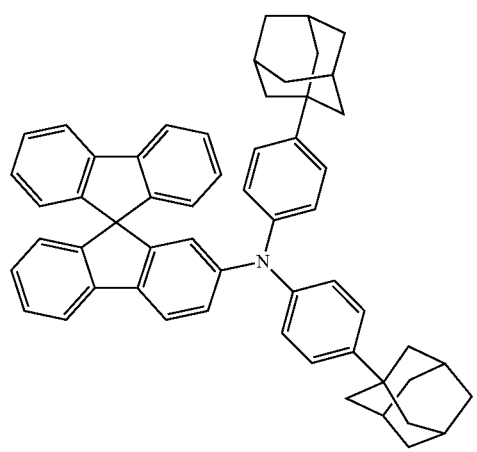
54
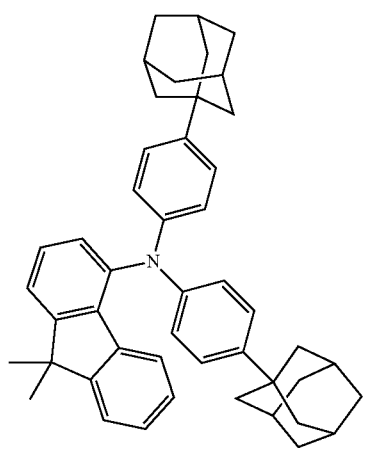
55
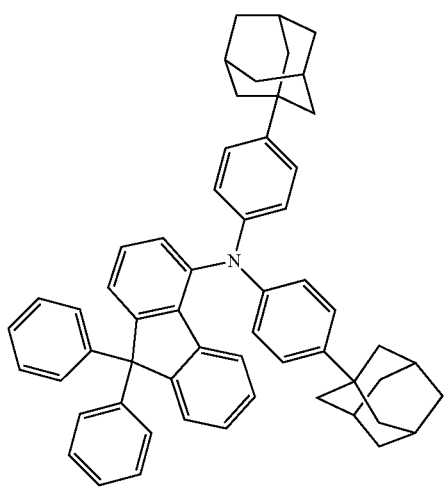

56
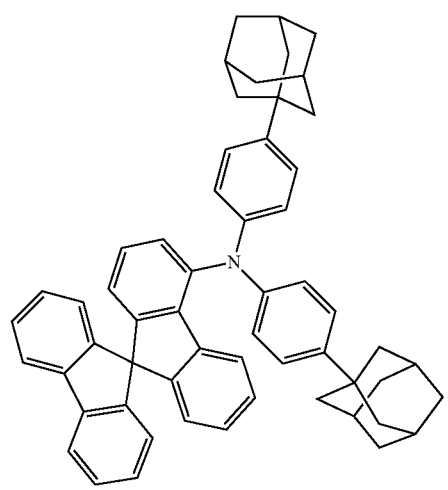
57
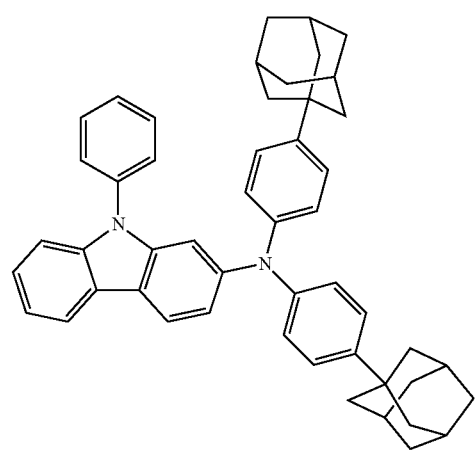
58
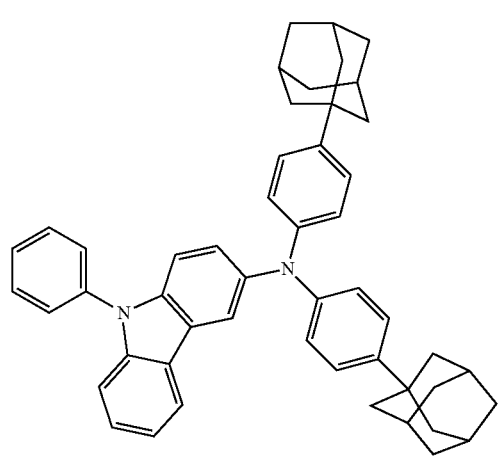
59
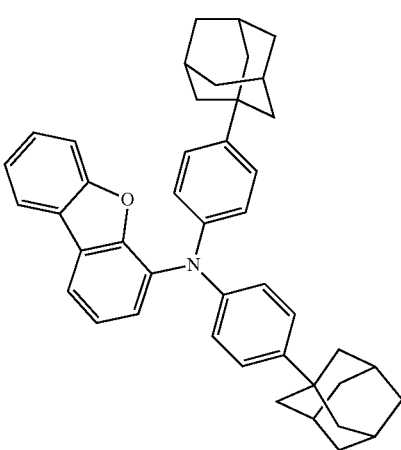
60
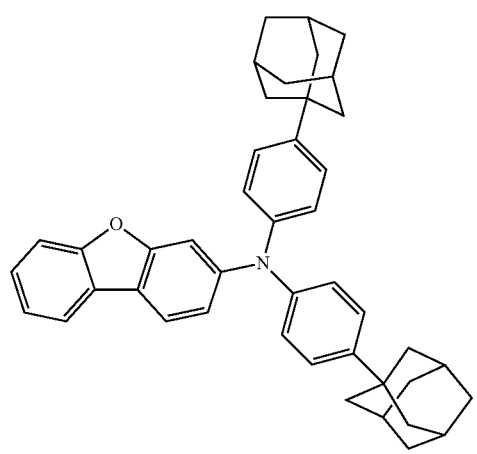
61
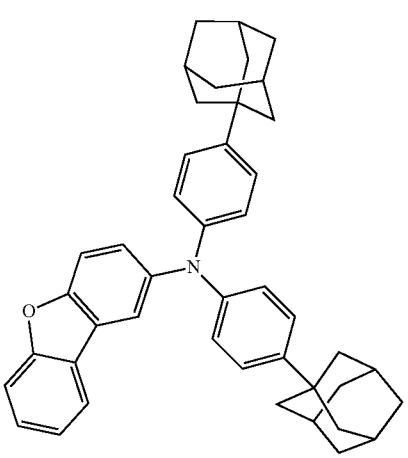

62
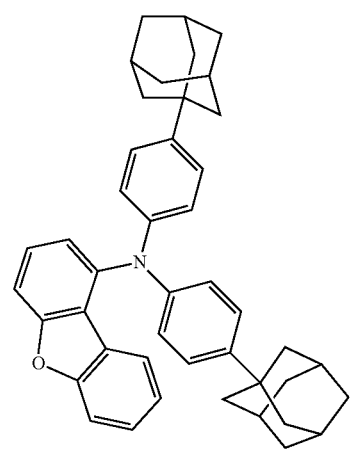
63
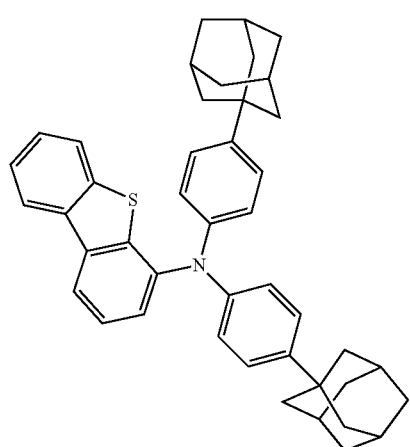
64
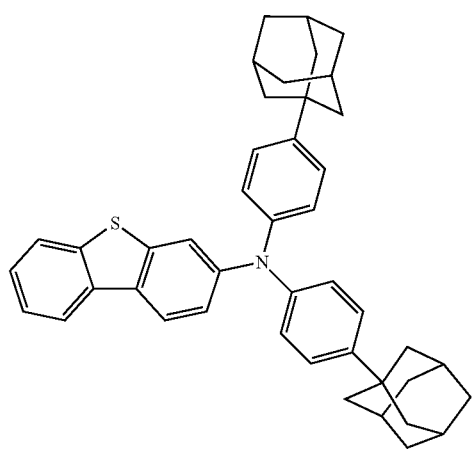
65
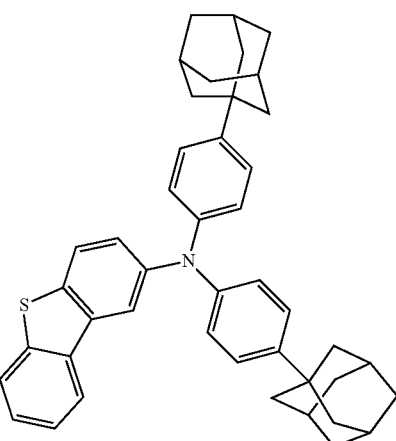
66
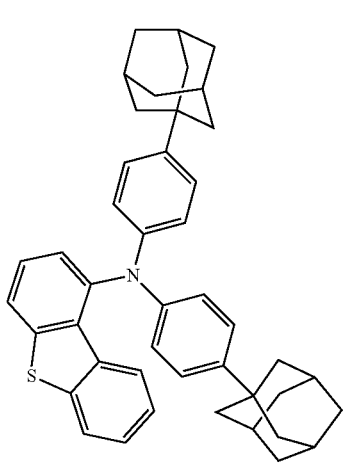
67
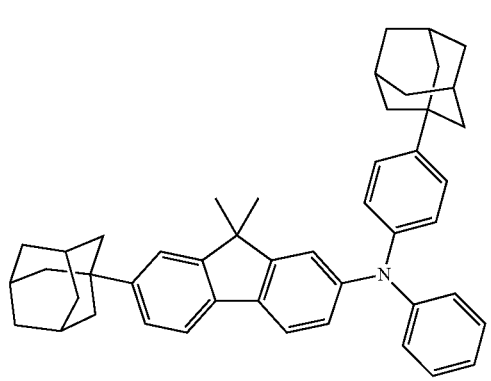

68
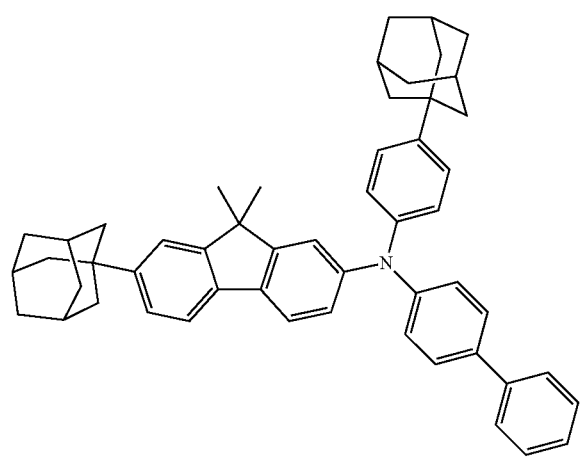
69
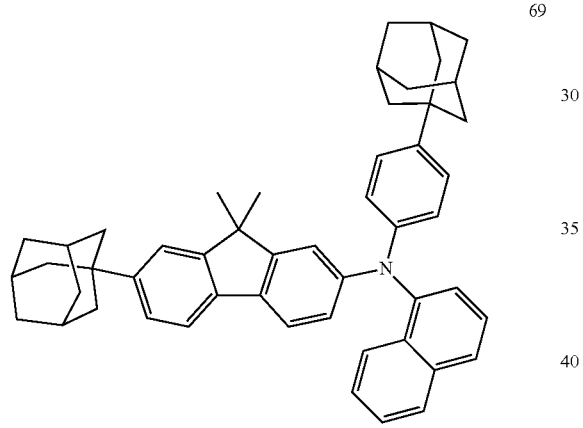
70
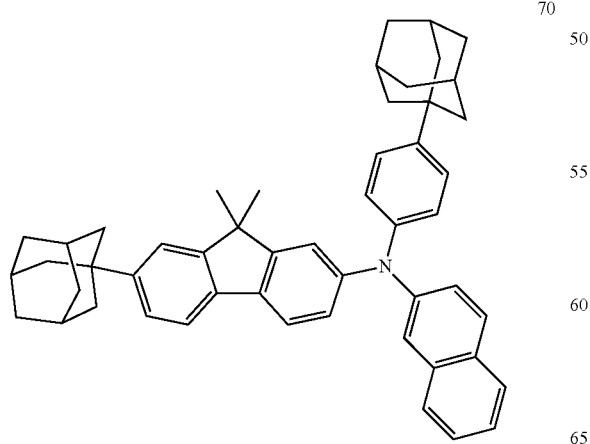
71
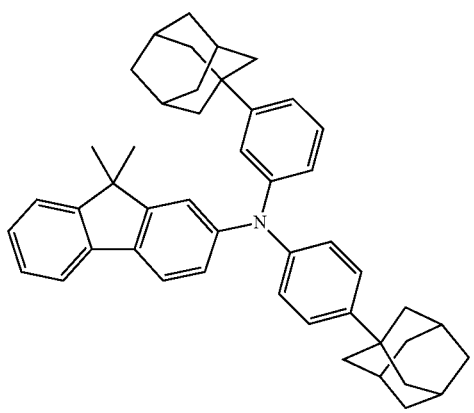
72
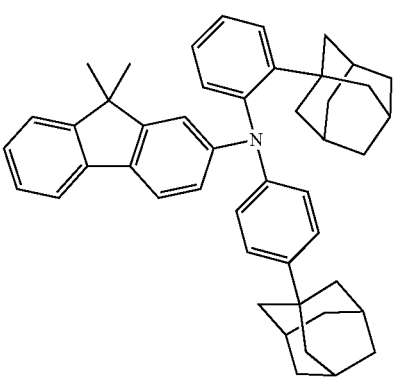
73
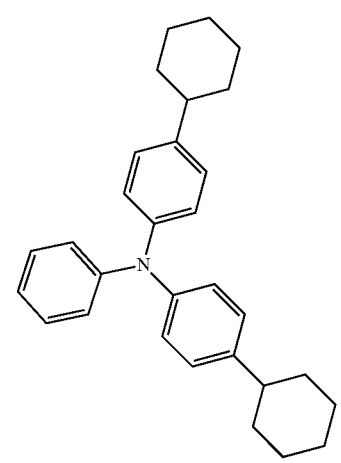

74
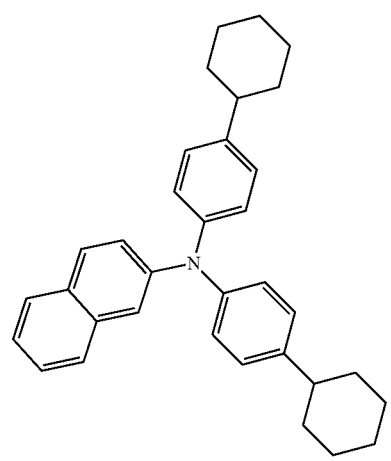
75
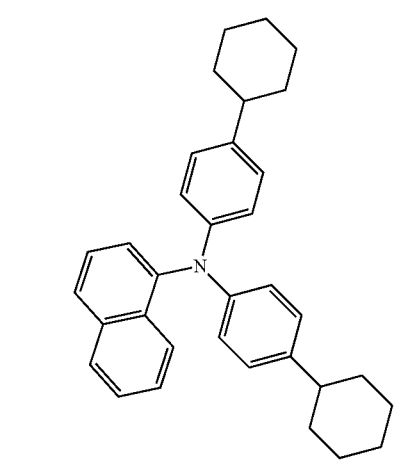
76
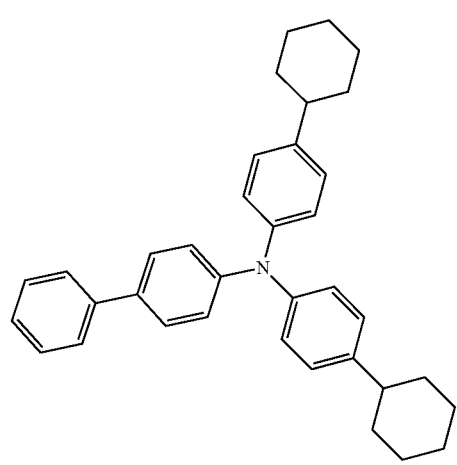
77
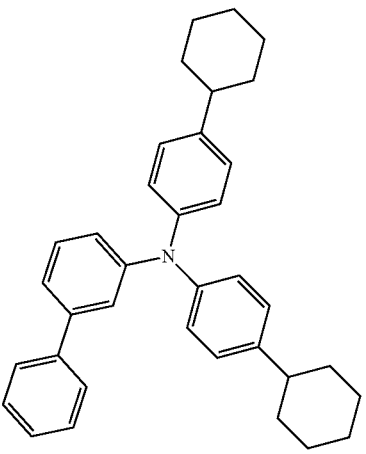
78
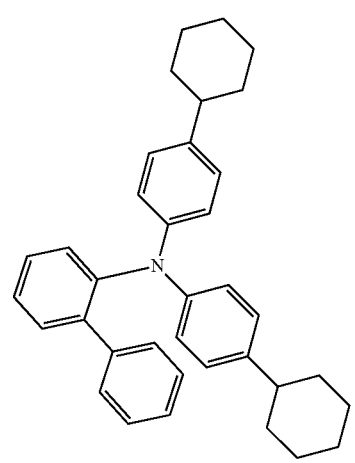
79
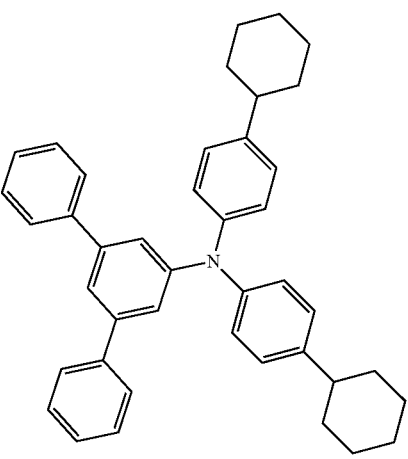

80
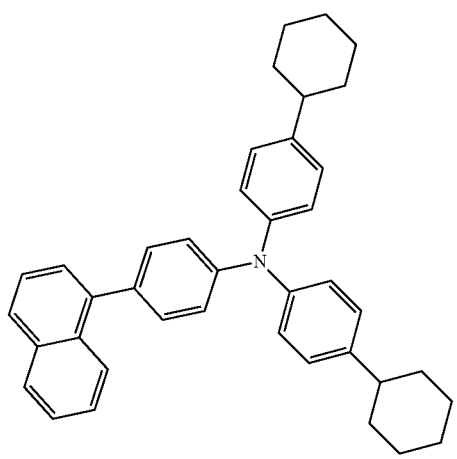
81
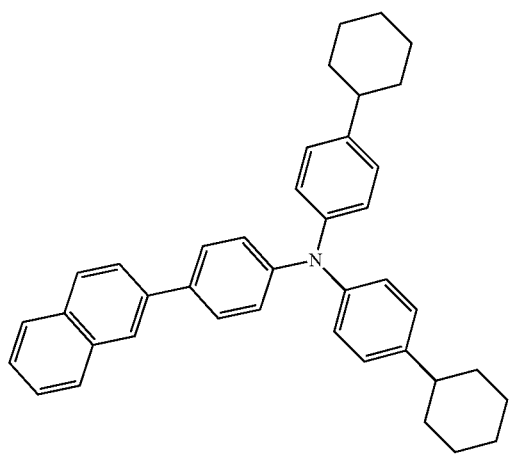
82
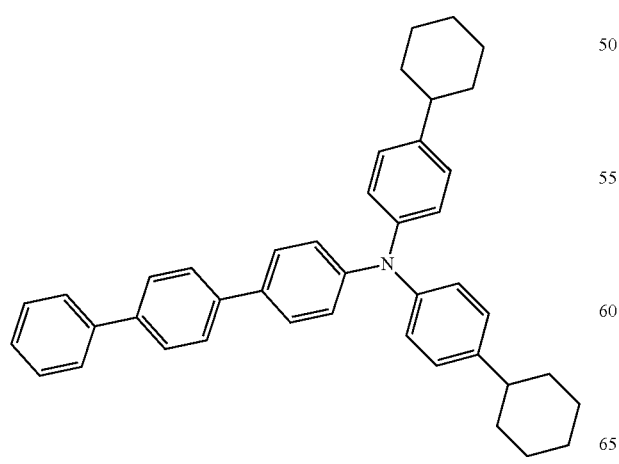
83
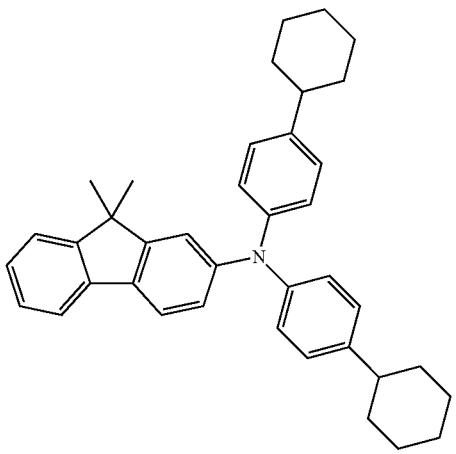
84
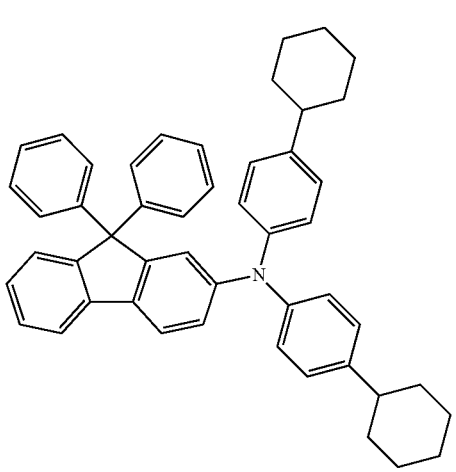
85
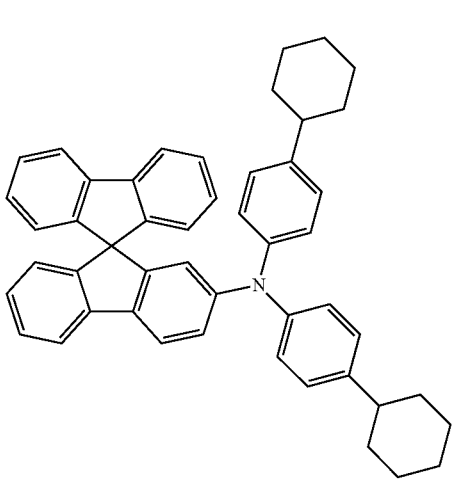

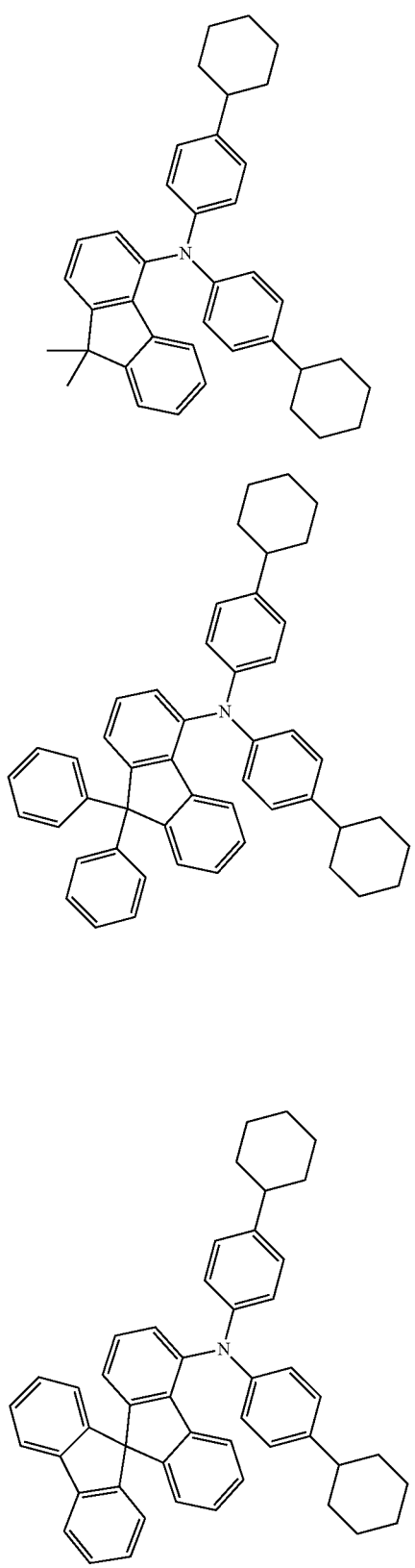
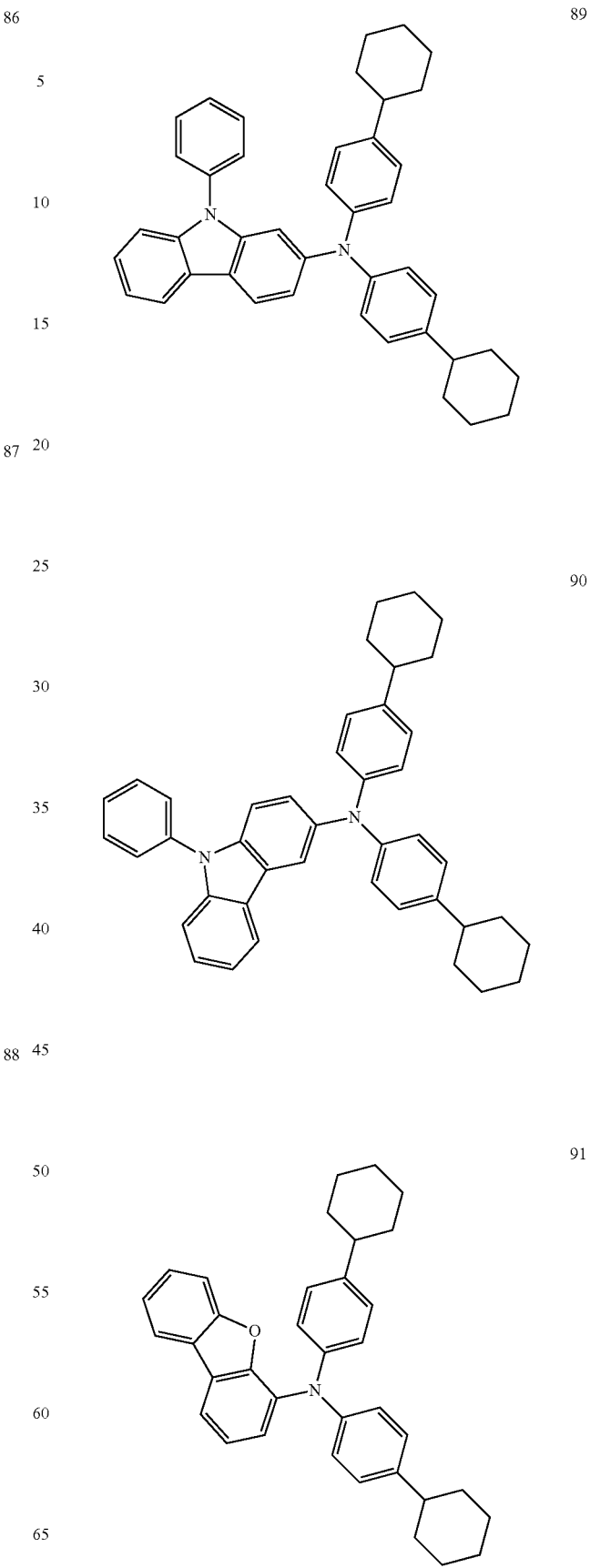

92
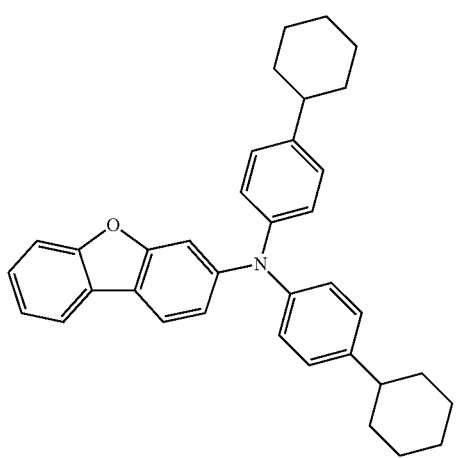
95
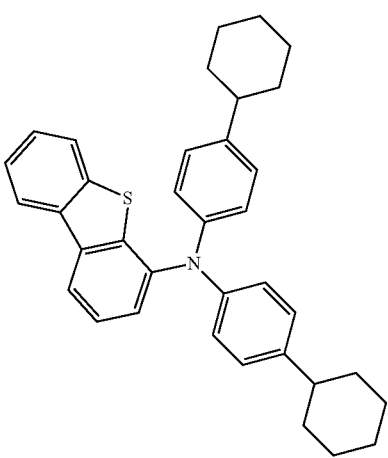
93
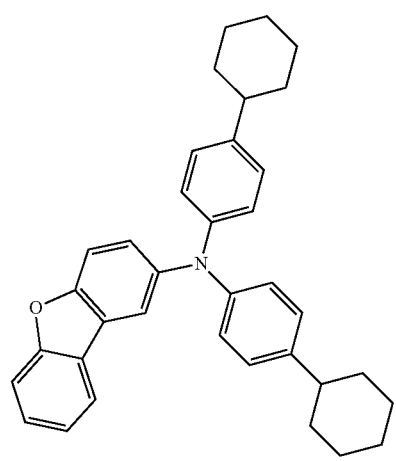
96
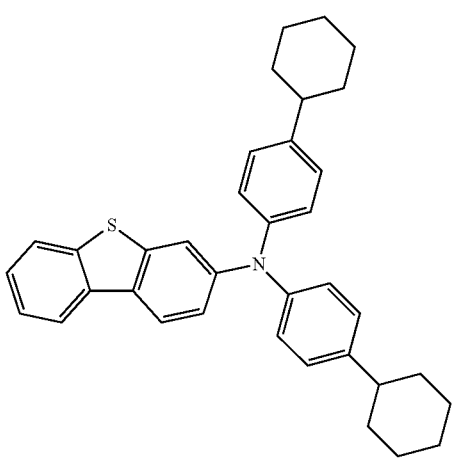
94
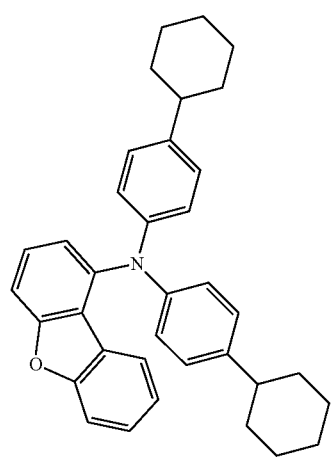
97
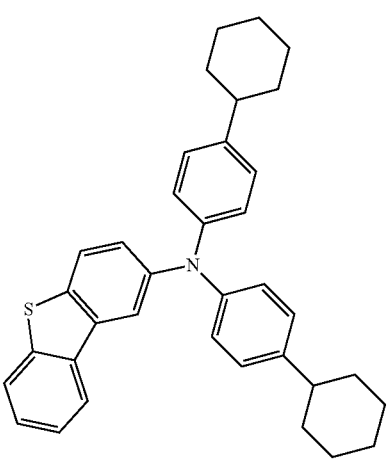

98
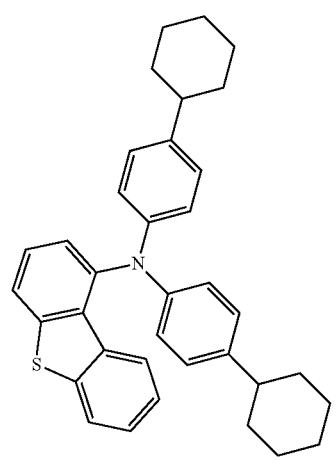
99
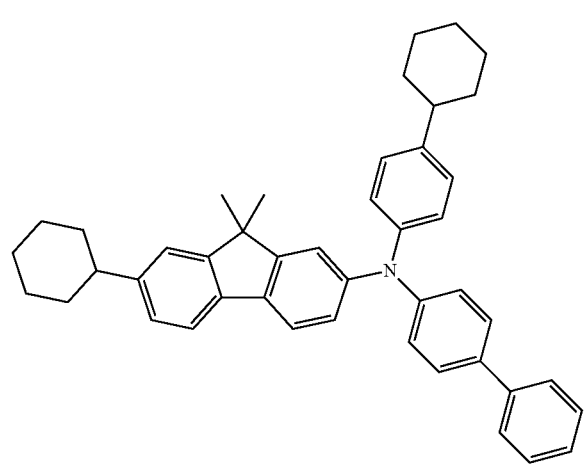
100
101
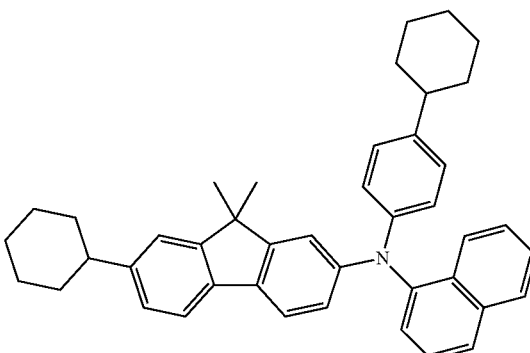
102
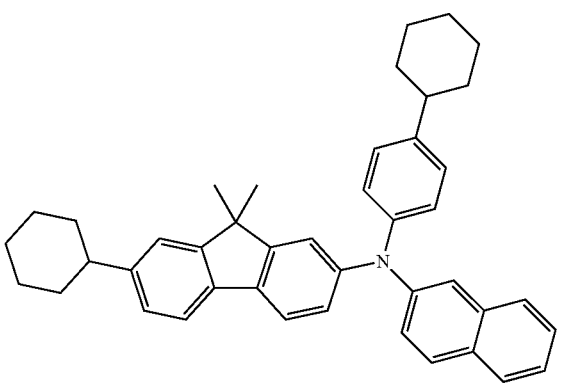
103
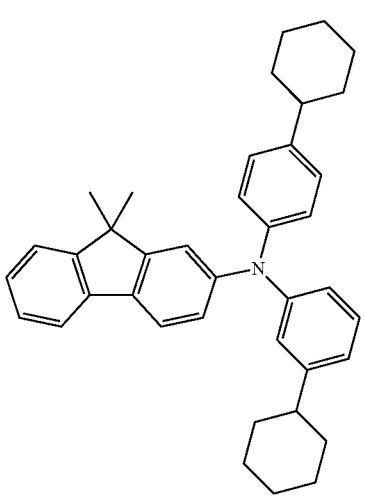

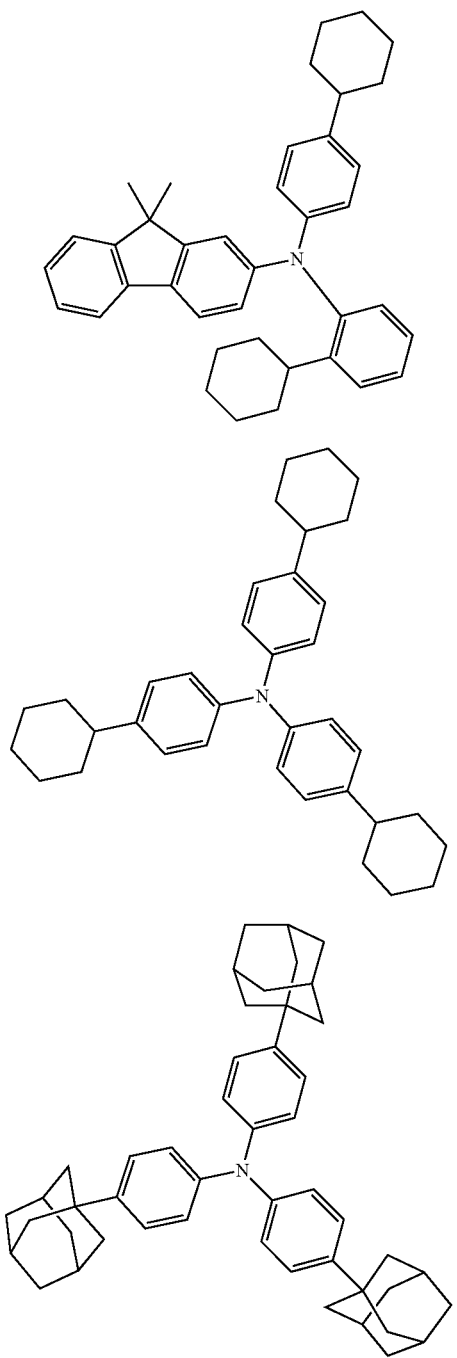

In the description, the term "substituted or unsubstituted" corresponds to substituted or unsubstituted with one or more substituents selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. Each of the listed substituents may be substituted or unsubstituted. For example, a biphenyl group may be interpreted as an aryl group or a phenyl group substituted with a phenyl group.

In the description, the term "combined with an adjacent group to form a ring" may mean forming a substituted or unsubstituted hydrocarbon ring, or a substituted or unsubstituted heterocycle via the combination with an adjacent group. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocyclic rings or polycyclic rings. The ring formed via the combination with an adjacent group may be combined with another ring to form a spiro structure.

In the description, the term "adjacent group" may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentane, two ethyl groups may be interpreted as "adjacent groups" to each other.

In the description, the halogen atom may be a fluorine atom, a chlorine atom, a bromine atom, or an iodine atom.

In the description, the alkyl may be a linear, branched, or cyclic type. The carbon number of the alkyl may be 1 to 50, 1 to 30, 1 to 20, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the aryl group means an optional functional group or substituent derived from an aromatic hydrocarbon ring. The aryl group may be a monocyclic aryl group or a polycyclic aryl group. The carbon number for forming rings in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the description, the fluorenyl group may be substituted, and two substituents may be combined with each other to form a spiro structure. Examples of a substituted fluorenyl group are as follows. However, an embodiment of the inventive concept is not limited thereto.

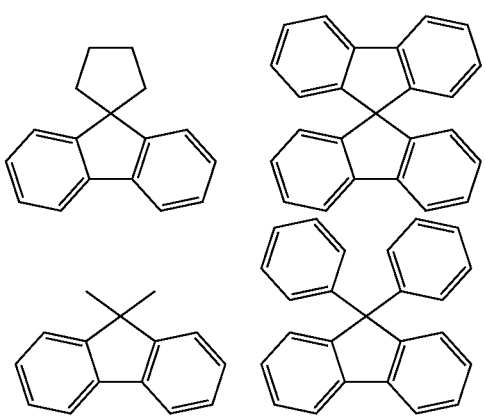

In the description, the heteroaryl group may include one or more among B, O, N, P, Si, and S as heteroatoms. If the heteroaryl group includes two or more heteroatoms, two or more heteroatoms may be the same or different. The heteroaryl group may be a monocyclic heterocyclic group or polycyclic heterocyclic group. The carbon number for forming rings of the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc., without limitation.

In the description, the explanation on the aryl group may be applied to the arylene group except that the arylene group is a divalent group. The explanation on the heteroaryl group may be applied to the heteroarylene group except that the heteroarylene group is a divalent group.

In the description, the silyl group includes an alkyl silyl group and an aryl silyl group. Examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc. However, an embodiment of the inventive concept is not limited thereto.

In the description, the carbon number of the amino group is not specifically limited, but may be 1 to 30. The amino group may include an alkyl amino group, an aryl amino group, or a heteroaryl amino group. Examples of the amino group include a methylamino group, a dimethylamino group, a phenylamino group, a diphenylamino group, a 9-methyl-anthracenylamino group, etc., without limitation.

In the description, the thio group may include an alkyl thio group and an aryl thio group. The thio group may mean the above-defined alkyl group or aryl group combined with a sulfur atom. Examples of the thio group include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., without limitation.

In the description, the oxy group may mean the above-defined alkyl group or aryl group which is combined with an oxygen atom. The oxy group may include an alkoxy group and an aryl oxy group. The alkoxy group may be a linear, branched, or cyclic chain. The carbon number of the alkoxy group is not specifically limited but may be, for example, 1 to 20 or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc. However, an embodiment of the inventive concept is not limited thereto.

In the description, the carbon number of the amine group is not specifically limited, but may be 1 to 30. The amine group may include an alkyl amine group and an aryl amine group. Examples of the amine group include a methylamine group, a dimethylamine group, a phenylamine group, a diphenylamine group, a naphthylamine group, a 9-methylanthracenylamine group, etc., without limitation.

In the description, an alkyl group in the alkylthio group, alkylsulfoxy group, alkylaryl group, alkylamino group, alkylboron group, alkyl silyl group, and alkyl amine group may be the same as the examples of the above-described alkyl group.

In the description, an aryl group in the aryloxy group, arylthio group, arylsulfoxy group, arylamino group, arylboron group, aryl silyl group, and aryl amine group may be the same as the examples of the above-described aryl group.

The third hole transport layer HTL3 may include a compound represented by Formula 2 below. The compound represented by Formula 2 may have a refractive index value of about 1.85 to about 2.40 at a wavelength of about 460 nm.

[Formula 2]

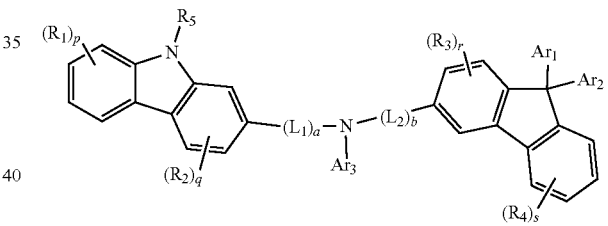

In Formula 2, $Ar_1$ and $Ar_2$ may be each independently a hydrogen atom, a deuterium atom, a halogen atom, a substituted or unsubstituted alkyl group of 1 to 30 carbon atoms, a substituted or unsubstituted aryl group of 6 to 30 ring-forming carbon atoms, or a substituted or unsubstituted heteroaryl group of 2 to 30 ring-forming carbon atoms, or combined with an adjacent group to form a ring. $Ar_3$ may be a substituted or unsubstituted aryl group of 6 to 30 ring-forming carbon atoms, or a substituted or unsubstituted heteroaryl group of 2 to 30 ring-forming carbon atoms. In Formula 2, a and b may each independently be 0 or 1, and $L_1$ and $L_2$ may be each independently a substituted or unsubstituted cycloalkylene group of 3 to 10 ring-forming carbon atoms, a substituted or unsubstituted heterocycloalkylene group of 2 to 10 ring-forming carbon atoms, a substituted or unsubstituted cycloalkenylene group of 3 to 10 ring-forming carbon atoms, a substituted or unsubstituted arylene group of 6 to 30 ring-forming carbon atoms, or a substituted or unsubstituted heteroarylene group of 2 to 60 ring-forming carbon atoms. In Formula 2, p and s may each independently be an integer from 0 to 4, q and r may each independently be an integer from 0 to 3, and $R_1$ to $R_5$ may each independently be a hydrogen atom, a deuterium atom, a halogen atom, a hydroxyl group, a cyano group, a nitro group, an amino group, a substituted or unsubstituted silyl group, a substituted or unsubstituted oxy group, a substituted or unsubstituted alkyl group of 1 to 60 carbon atoms, a substituted or unsubstituted heterocycloalkyl group of 3 to 60 ring-forming carbon atoms, a substituted or unsubstituted aryl group of 6 to 60 ring-forming carbon atoms, or a substituted or unsubstituted heteroaryl group of 2 to 60 ring-forming carbon atoms.

The compound for the third hole transport layer HTL3, represented by Formula 2 may be selected from any one among the compounds in Compound Group 2 below. In the light emitting diode OEL of an embodiment, the third hole transport layer HTL3 may include at least one among the compounds in the Compound Group 2 below.

[Compound Group 2]

1

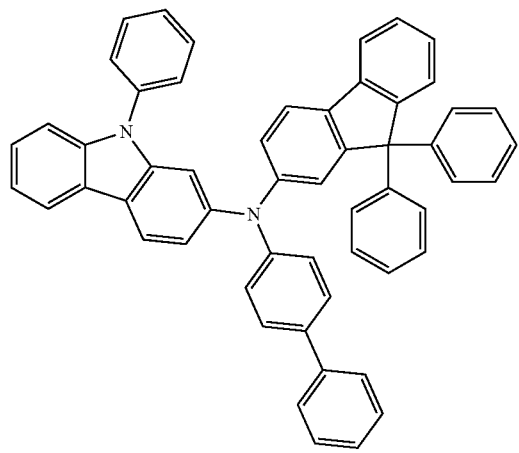

2

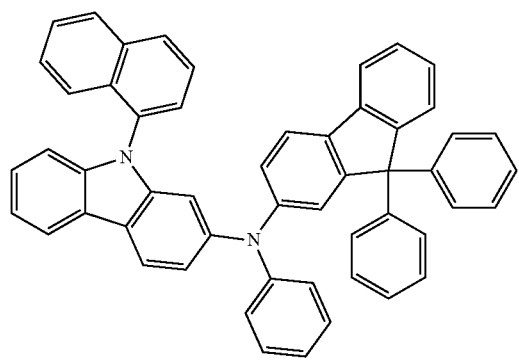

3

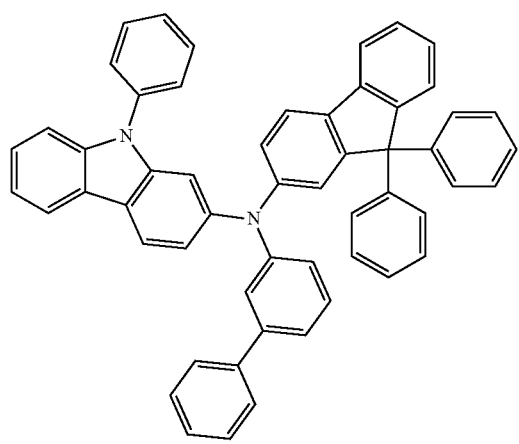

4

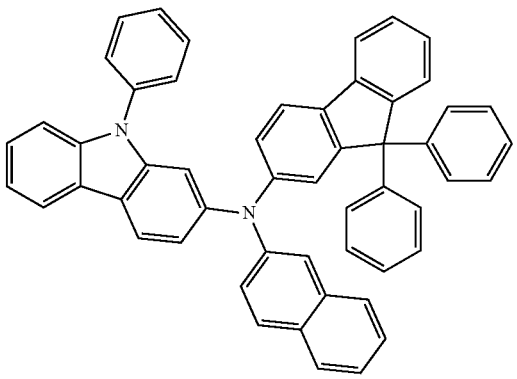

5

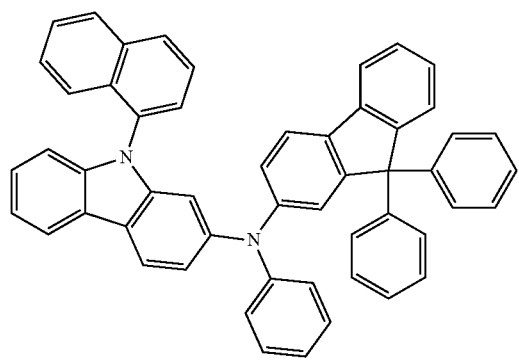

6

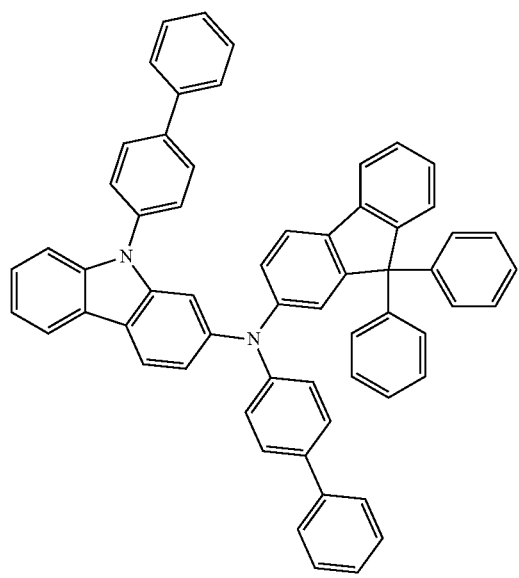
7
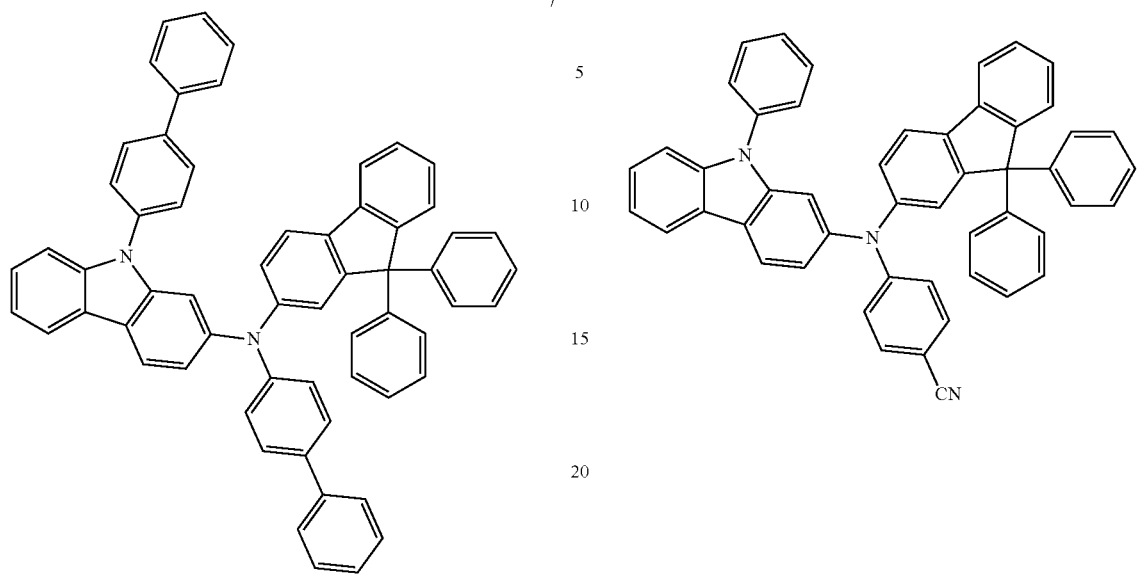
8
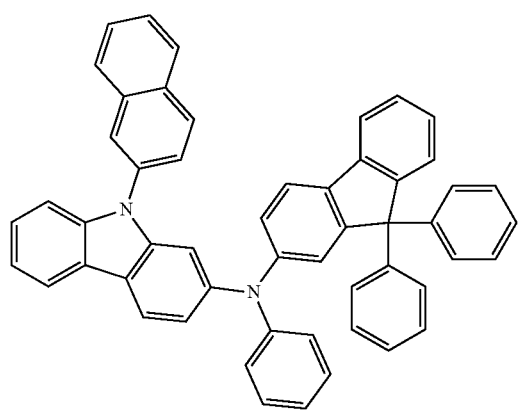
9
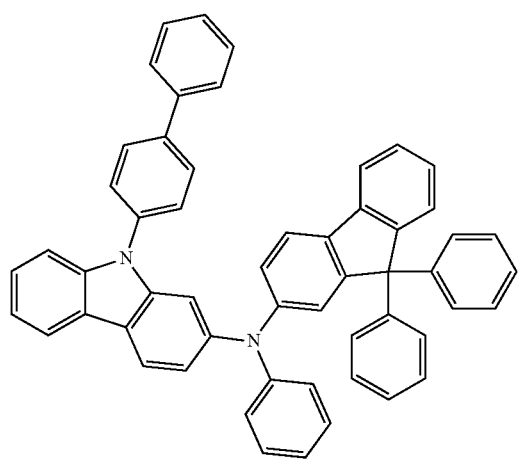
10
11
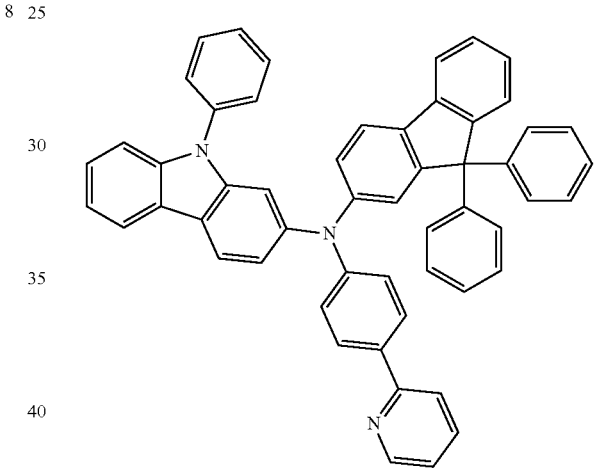
12

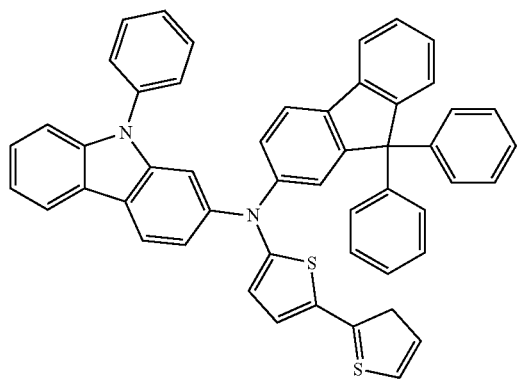
13
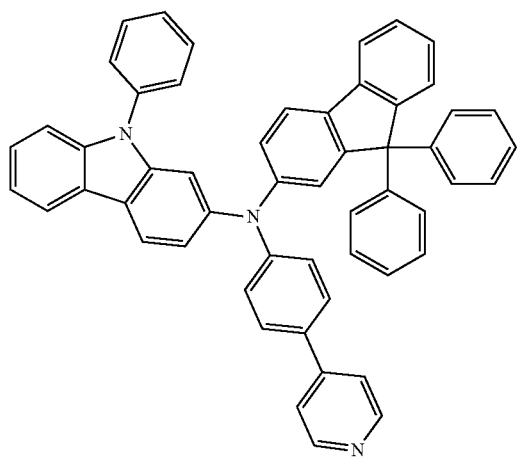
14
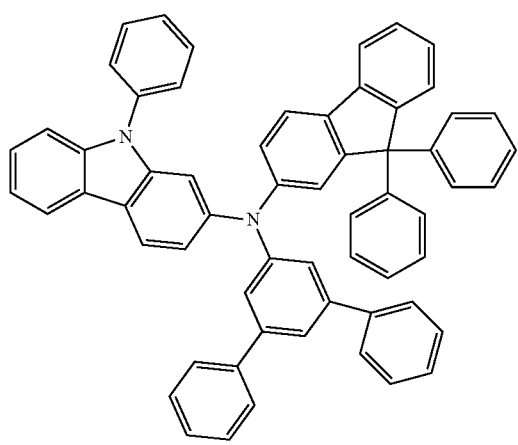
15
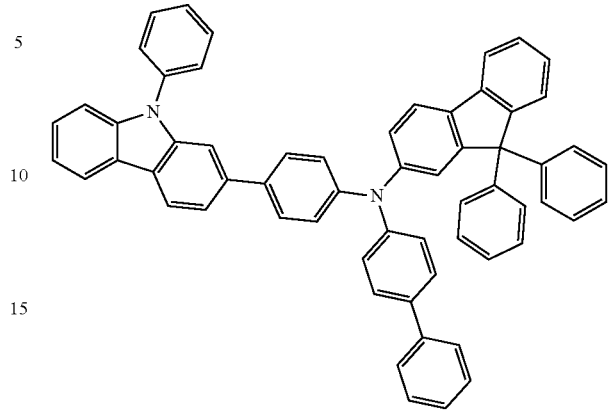
16
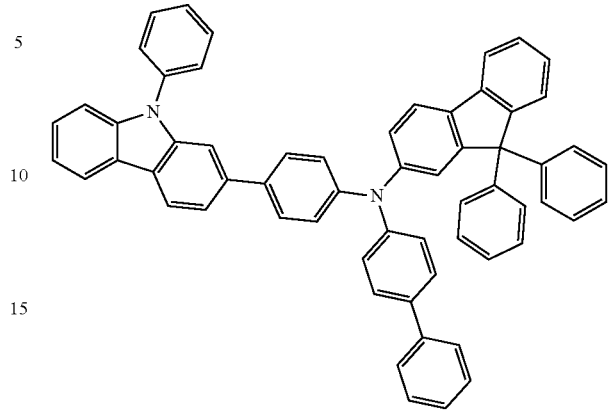
17
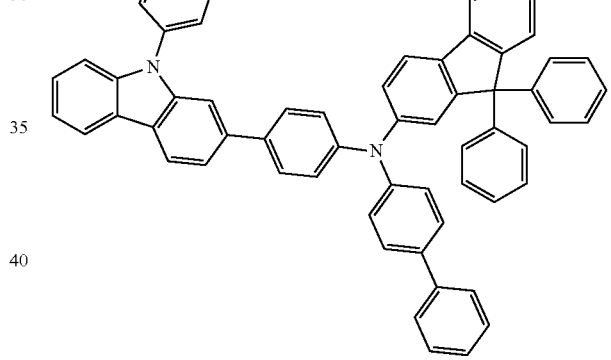
18

19
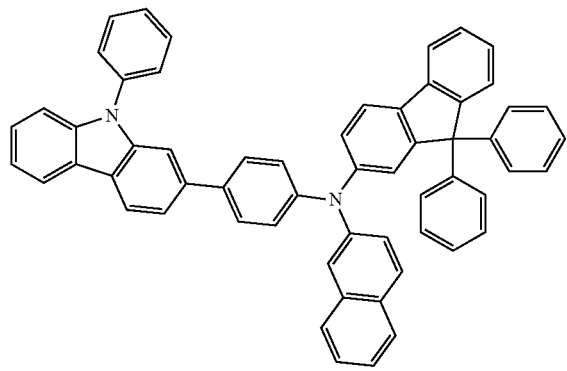
20
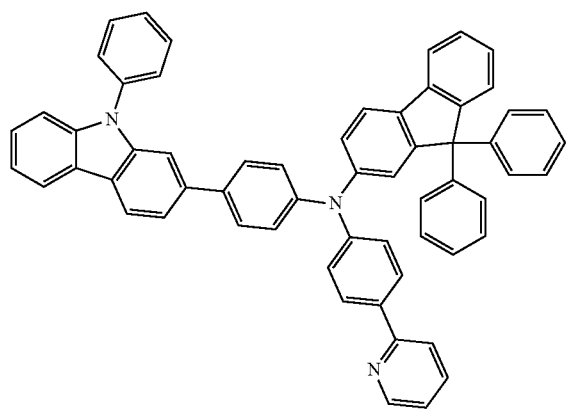
21
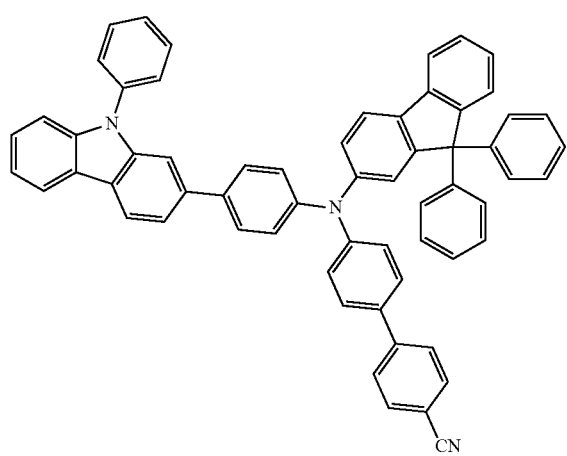
-continued
22
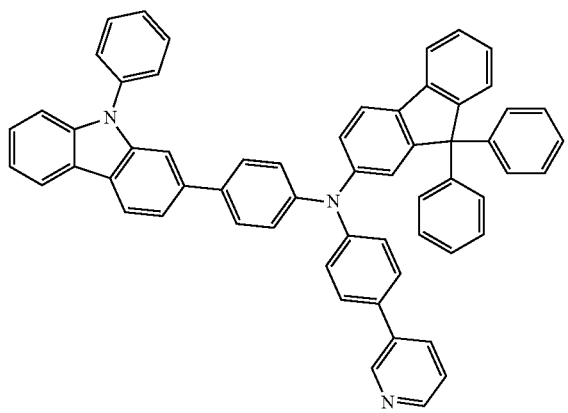
23
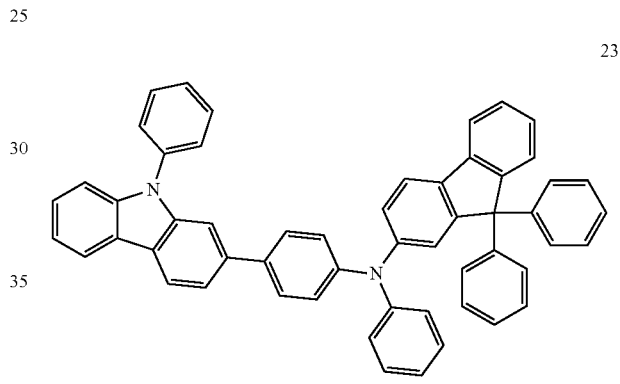
24
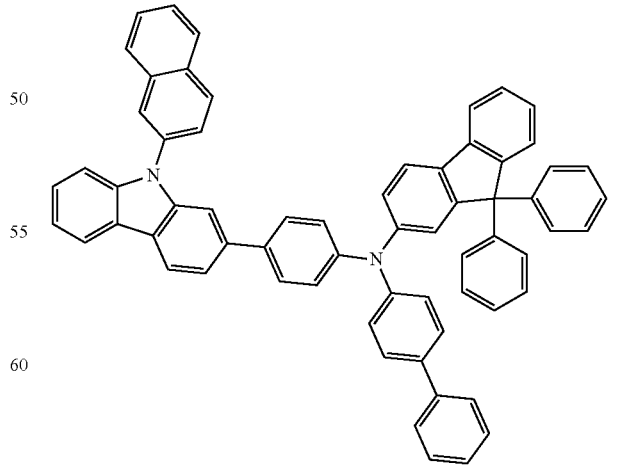

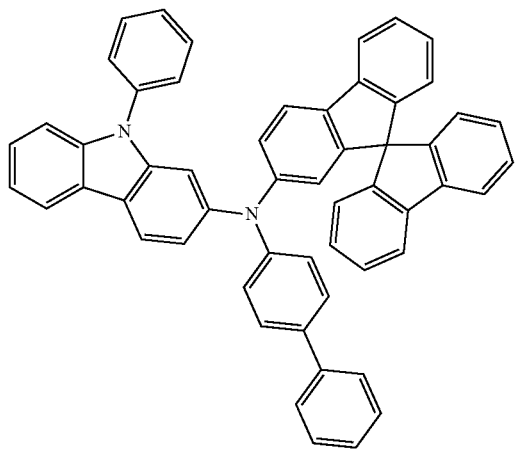
25
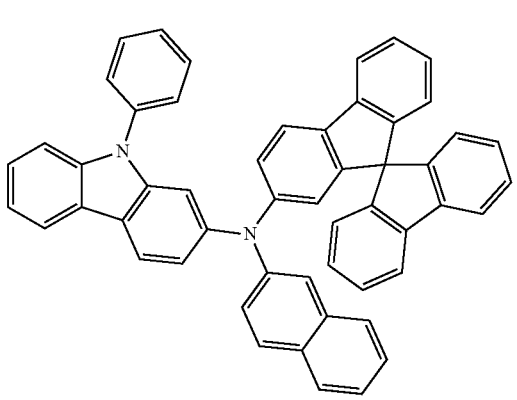
28
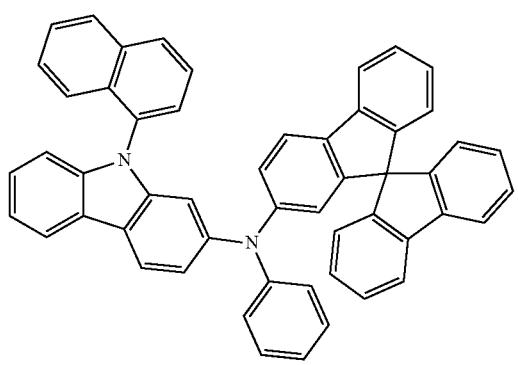
26
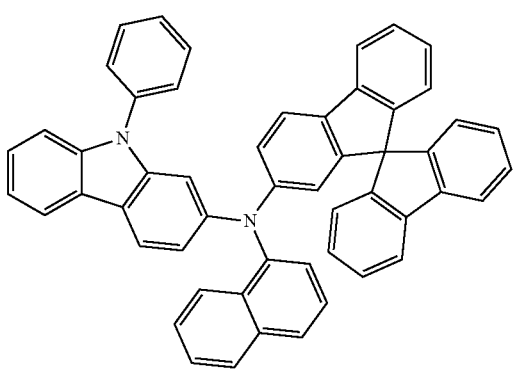
29
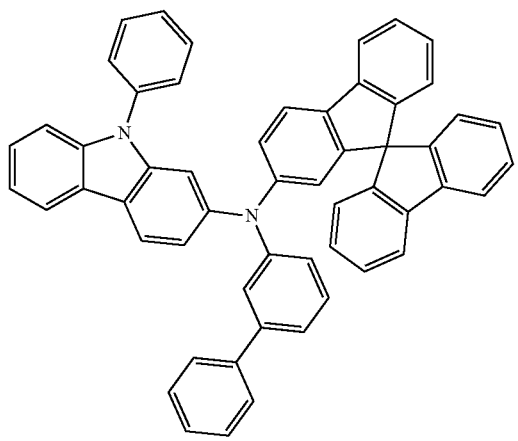
27
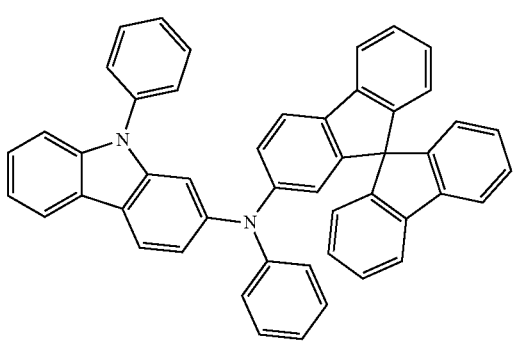
30

31
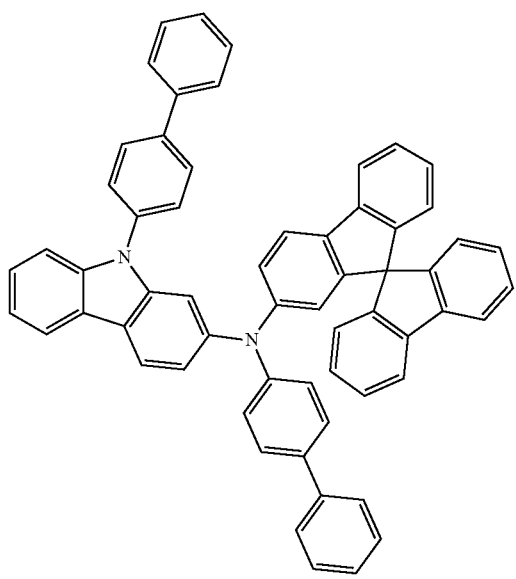
32
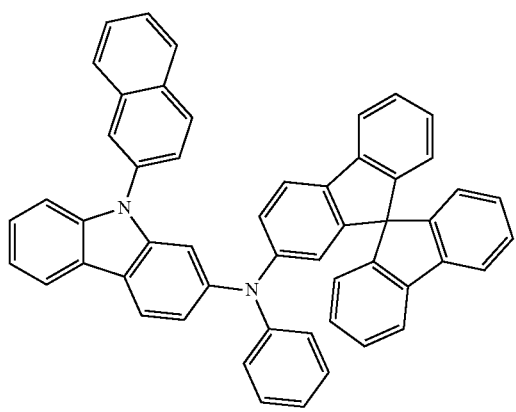
33
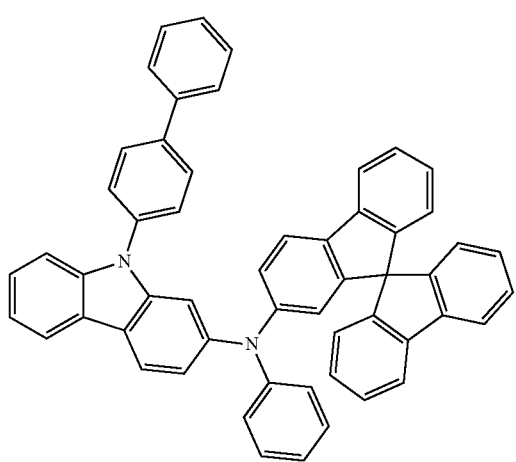
34
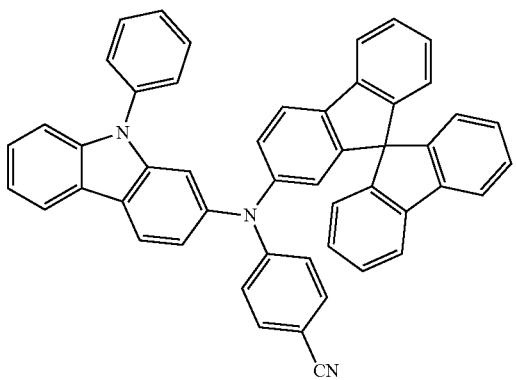
35
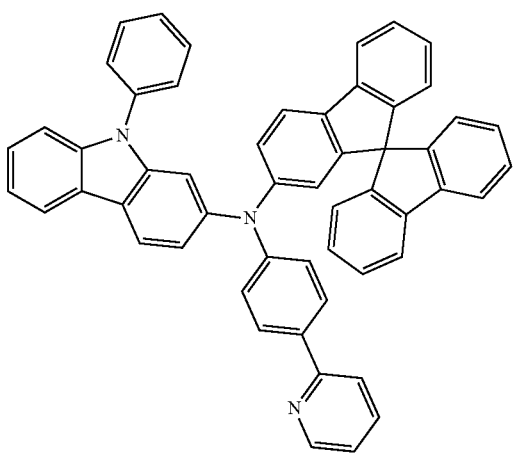
36
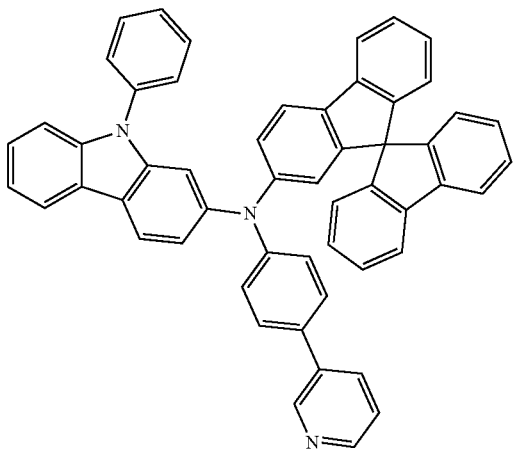

37
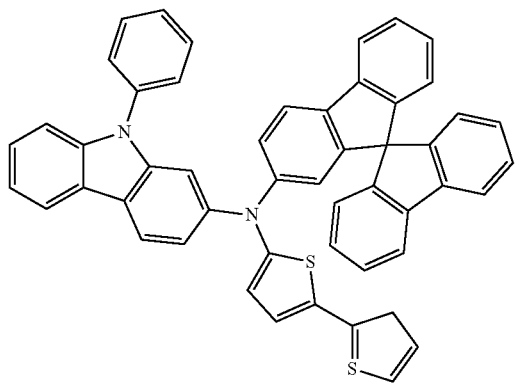
38
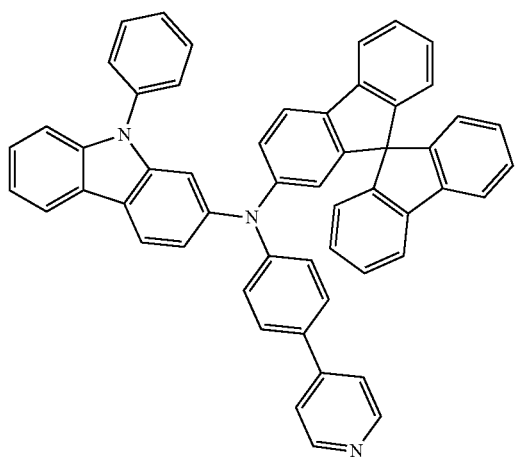
39
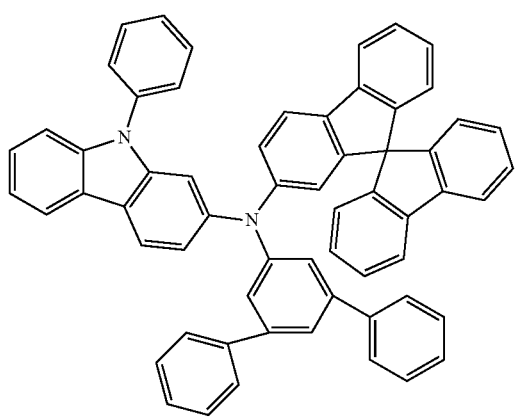
40
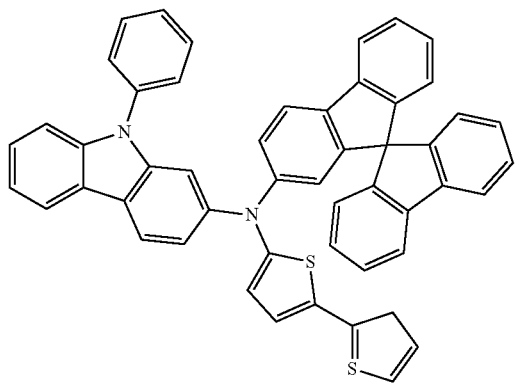
41
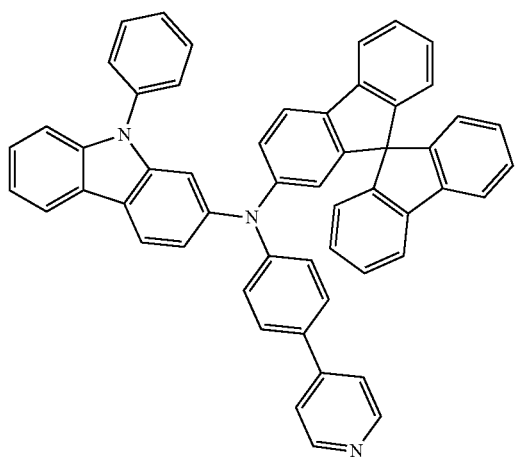
42
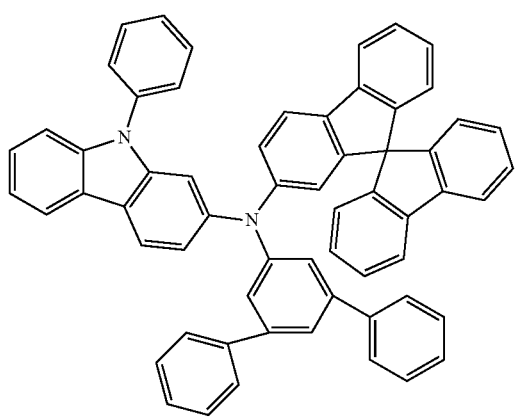

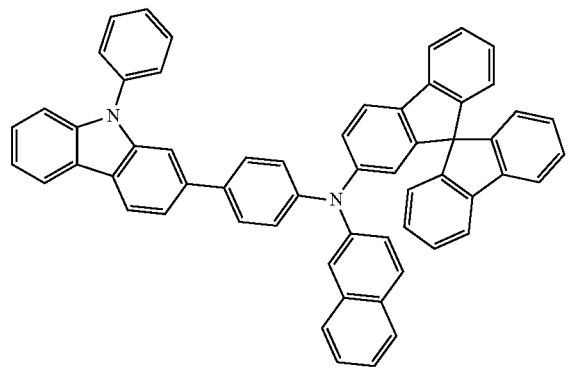
43
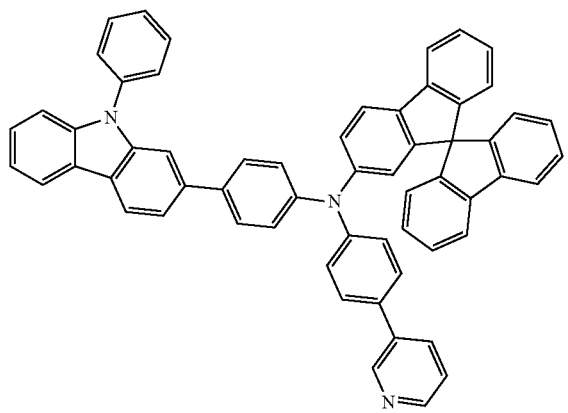
46
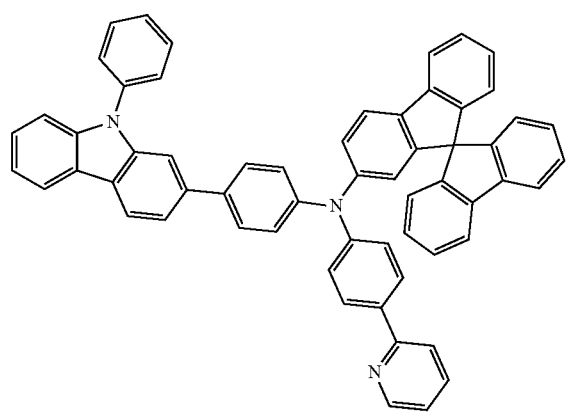
44
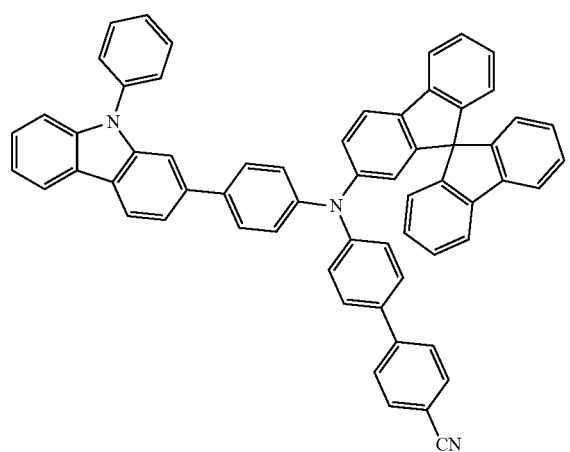
45
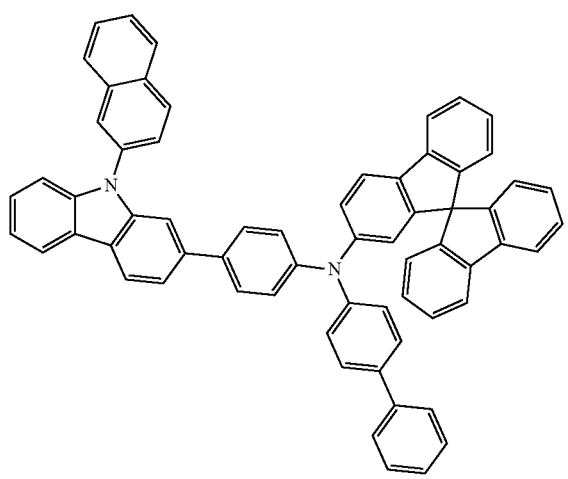
47
48

49
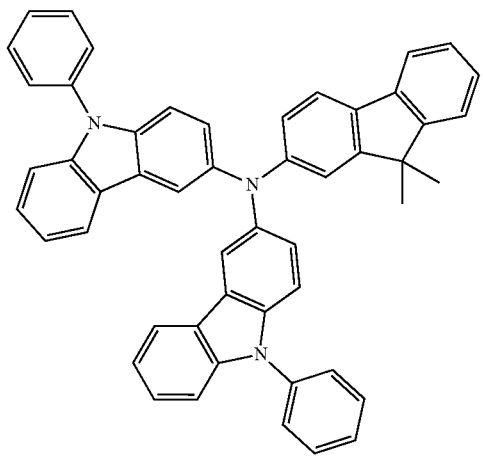
50
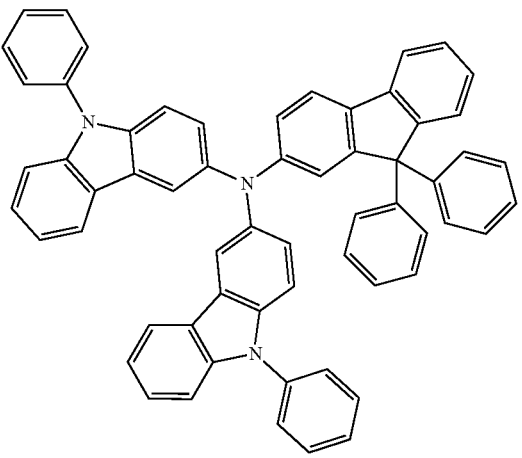
51
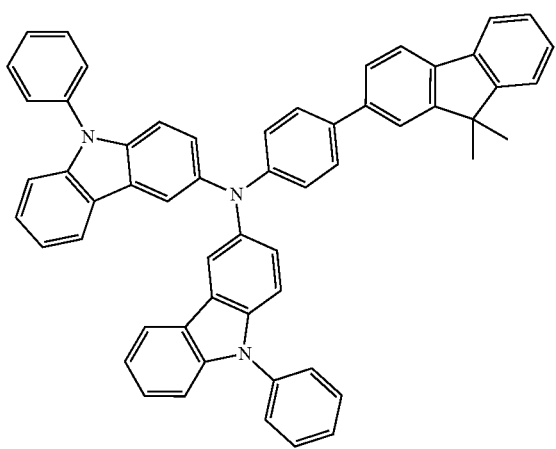
52
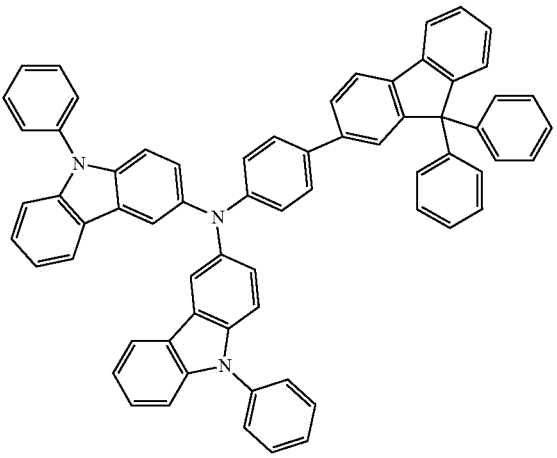
53
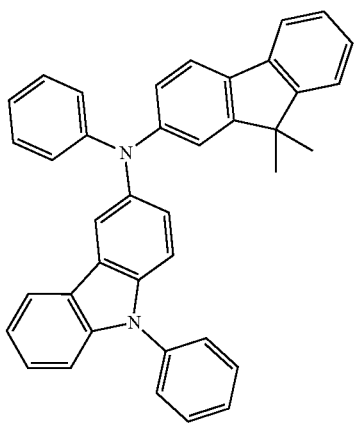
54
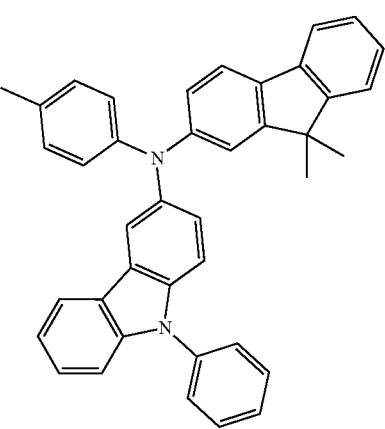

-continued
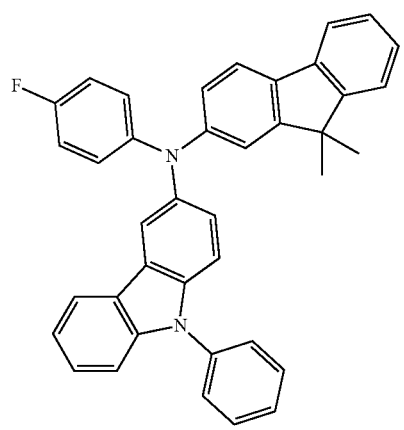
55
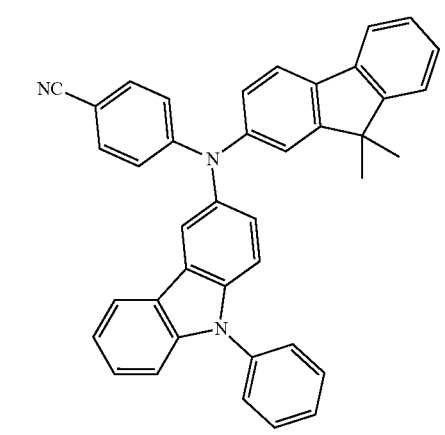
56
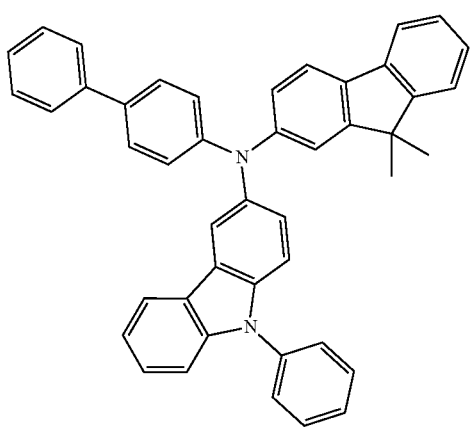
57
-continued
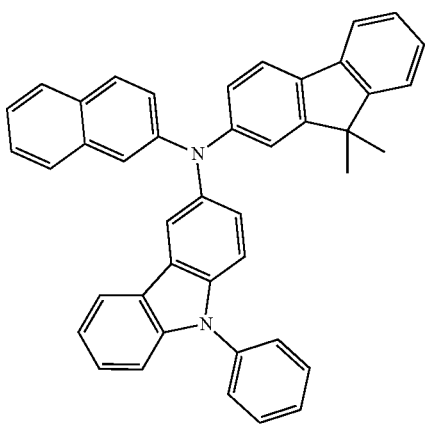
58
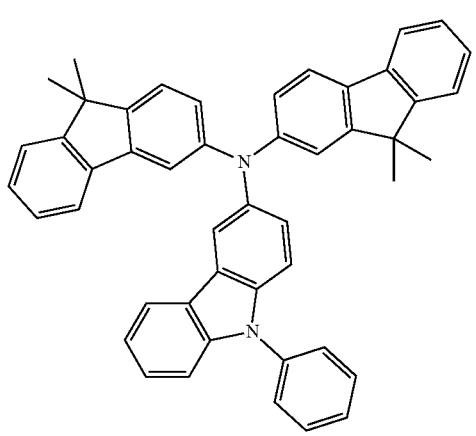
59
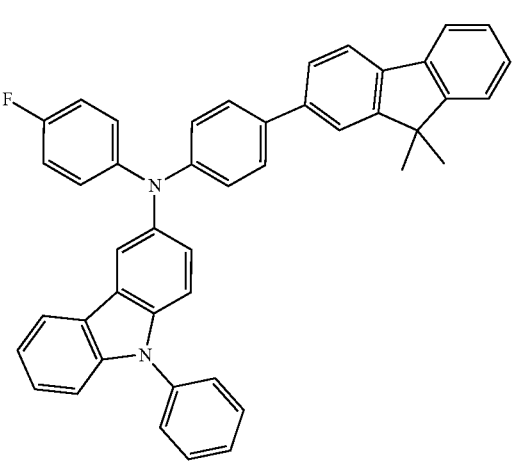
60

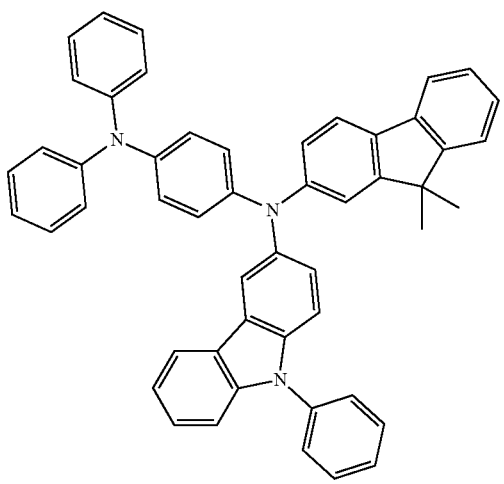
61
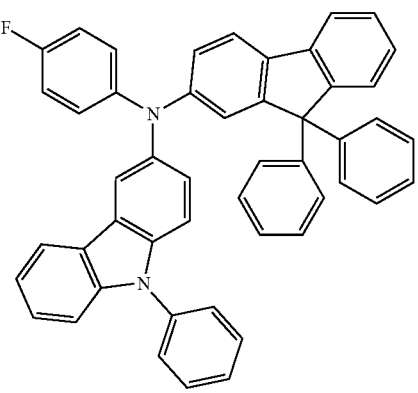
64
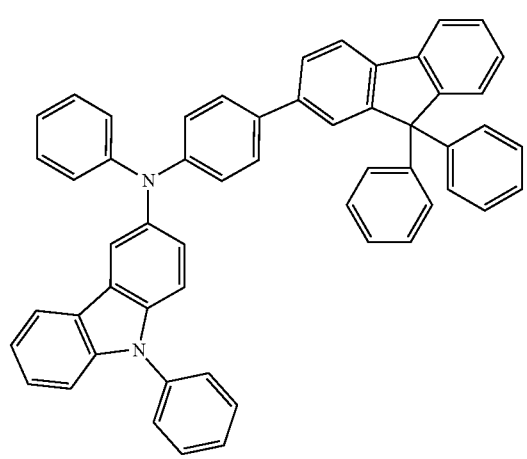
62
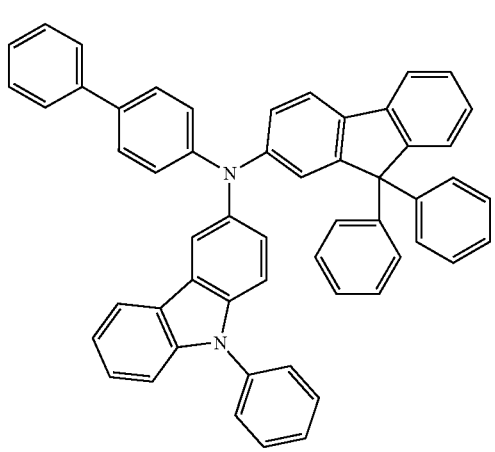
65
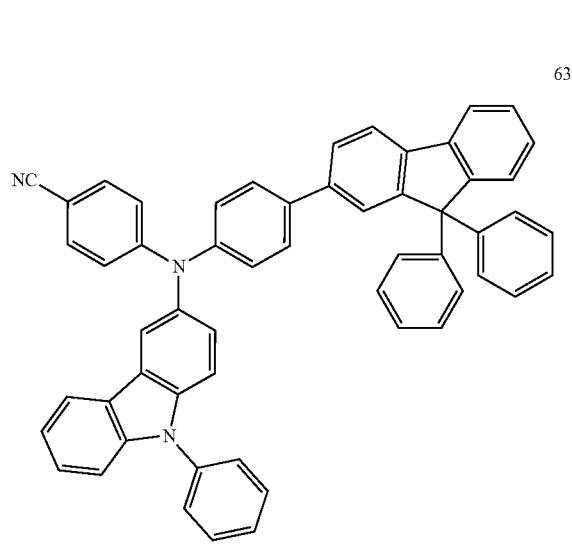
63
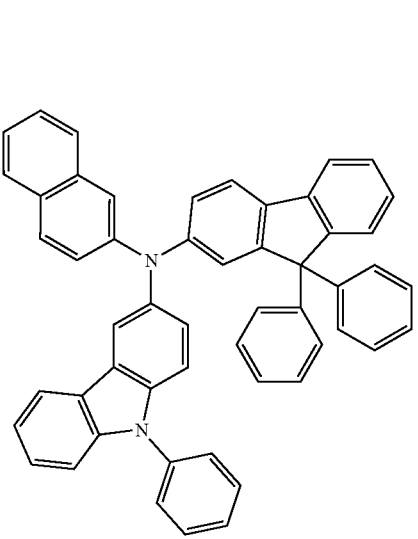
66

-continued

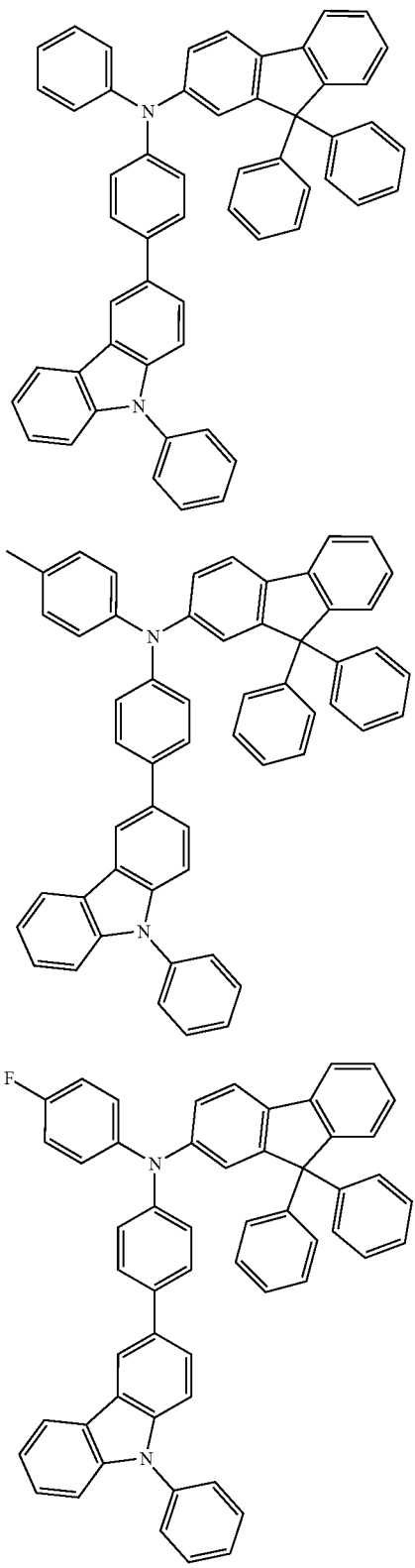

The hole transport region HTR of the light emitting diode OEL of an embodiment may include three hole transport layers HTL1, HTL2, and HTL3. The light emitting diode OEL of an embodiment may include hole transport layers obtained by stacking first hole transport layer HTL1/third hole transport layer HTL3/second hole transport layer HTL2 in order between the first electrode EL1 and the emission layer EML, and may show excellent emission efficiency properties. In an embodiment, the refractive indexes of the first hole transport layer HTL1 and the second hole transport layer HTL2 may each be less than the refractive index of the third hole transport layer HTL3, and a refractive index difference may be greater than about 0.1.

The emission layer EML is provided on the hole transport region HTR. The emission layer EML may have a thickness in a range of, for example, about 100 Å to about 1,000 Å. For example, the thickness of the emission layer EML may be in a range of about 100 Å to about 300 Å. The emission layer EML may be a single layer formed using a single material, a single layer formed using multiple different materials, or have a multilayer structure having multiple layers formed using multiple different materials.

The emission layer EML may emit any one among red light, green light, blue light, white light, yellow light, and cyan light. The emission layer EML may include a fluorescence emitting material or a phosphorescence emitting material. In an embodiment, the emission layer EML may include a quantum dot.

In the light emitting diode OEL of an embodiment, the emission layer EML may include anthracene derivatives, pyrene derivatives, fluoranthene derivatives, chrysene derivatives, dihydrobenzanthracene derivatives, or triphenylene derivatives. For example, the emission layer EML may include anthracene derivatives or pyrene derivatives. However, an embodiment of the inventive concept is not limited thereto, and the emission layer EML may include other light emitting materials used in the art.

In the light emitting diode OEL of an embodiment, the electron transport region ETR is provided on the emission layer EML. The electron transport region ETR may include at least one of a hole blocking layer, an electron transport layer, and an electron injection layer, but an embodiment of the inventive concept is not limited thereto.

The electron transport region ETR may have a single layer formed using a single material, a single layer formed using multiple different materials, or a multilayer structure having multiple layers formed using multiple different materials.

For example, the electron transport region ETR may have a single layer structure of an electron injection layer or an electron transport layer, or a single layer structure formed using an electron injection material and an electron transport material. Also, the electron transport region ETR may have a single layer structure formed using multiple different materials, or a structure stacked from the emission layer EML of electron transport layer/electron injection layer, or hole blocking layer/electron transport layer/electron injection layer, without limitation. A thickness of the electron transport region ETR may be, for example, in a range of about 1,000 Å to about 1,500 Å.

If the electron transport region ETR includes the electron injection layer, the electron transport region ETR may include a metal halide such as LiF, NaCl, CsF, RbCl, RbI, and CuI, a lanthanide metal such as Yb, a metal oxide such as $Li_2O$ and BaO, or lithium quinolate (LiQ). However, an embodiment of the inventive concept is not limited thereto. The electron injection layer may also be formed using a mixture material of an electron transport material and an insulating organo-metal salt. The organo-metal salt may be a material having an energy band gap of about 4 eV or more. For example, the organo-metal salt may include, for example, metal acetates, metal benzoates, metal acetoacetates, metal acetylacetonates, or metal stearates. If the electron transport region ETR includes the electron transport layer, the electron transport region ETR may include an anthracene-based compound. However, an embodiment of the inventive concept is not limited thereto. The electron transport region ETR may include other electron transport materials used in the art.

The second electrode EL2 is provided on the electron transport region ETR. The second electrode EL2 may be a common electrode or a cathode. The second electrode EL2 may be a transmissive electrode or a transflective electrode. If the second electrode EL2 is the transmissive electrode, the second electrode EL2 may be formed using a transparent metal oxide, for example, ITO, IZO, ZnO, ITZO, etc. If the second electrode EL2 is the transflective electrode, the second electrode EL2 may include Ag, Mg, Cu, Al, Pt, Pd, Au, Ni, Nd, Ir, Cr, Li, Ca, LiF/Ca, LiF/Al, Mo, Ti, compounds including thereof, or mixtures thereof (for example, a mixture of Ag and Mg). Otherwise, the second electrode EL2 may have a multilayered structure including a reflective layer or a transflective layer formed using the above-described materials and a transparent conductive layer formed using ITO, IZO, ZnO, ITZO, etc.

On the second electrode EL2 of the light emitting diode OEL of an embodiment, a capping layer (not shown) may be further disposed. The capping layer (not shown) may include, for example, α-NPD, NPB, TPD, m-MTDATA, Alq$_3$, CuPc, N4,N4,N4',N4'-tetra(biphenyl-4-yl) biphenyl-4,4'-diamine (TPD15), 4,4',4"-tris(carbazol-9-yl) triphenylamine (TCTA), etc.

The display device of an embodiment includes multiple light emitting diodes, and at least one light emitting diode among the multiple light emitting diodes may have the above-described configuration of the light emitting diode according to an embodiment.

Figure 6:
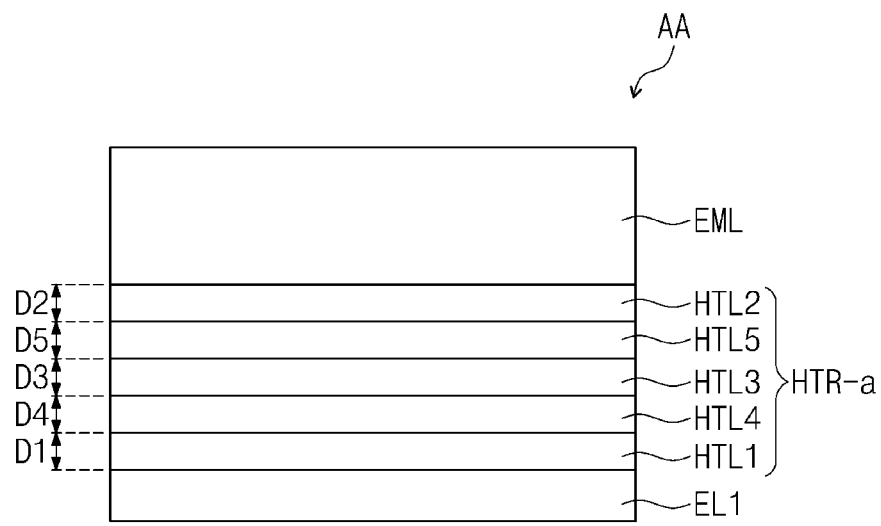
FIG. 6 is a schematic cross-sectional view of a portion of a light emitting diode according to an embodiment.

FIG. 6 is a schematic cross-sectional view of a portion of a light emitting diode according to an embodiment. When compared with a portion of the light emitting diode shown in FIG. 5, the light emitting diode according to an embodiment, shown in FIG. 6 is different only in the configuration of a hole transport region.

Referring to FIG. 6, in an embodiment, a hole transport region HTR-a may include first to fifth hole transport layers HTL1 to HTL5. For example, when compared with an embodiment shown in FIG. 5, the hole transport region HTR-a in the light emitting diode according to an embodiment may further include a fourth hole transport layer HTL4 and a fifth hole transport layer HTL5.

The fourth hole transport layer HTL4 may be disposed between the first hole transport layer HTL1 and the third hole transport layer HTL3, and the fifth hole transport layer HTL5 may be disposed between the second hole transport layer HTL2 and the third hole transport layer HTL3.

The fourth hole transport layer HTL4 may include both the amine compound represented by Formula 1 and included in the first hole transport layer HTL1, and the compound represented by Formula 2 and included in the third hole transport layer HTL3. In the fourth hole transport layer HTL4, the amount of the amine compound represented by Formula 1 at a portion adjacent to the first hole transport layer HTL1 may be greater than the amount of the amine compound represented by Formula 1 at a portion adjacent to the third hole transport layer HTL3. In the fourth hole transport layer HTL4, the amount of the compound represented by Formula 2 at a portion adjacent to the third hole transport layer HTL3 may be greater than the amount of the compound represented by Formula 2 at a portion adjacent to the first hole transport layer HTL1. For example, the fourth hole transport layer HTL4 is a layer including both the compound forming the first hole transport layer HTL1 and the compound forming the third hole transport layer HTL3, and in the fourth hole transport layer HTL4, the amount of the amine compound represented by Formula 1 among the amount of the total fourth hole transport layer HTL4 may be gradually reduced in a direction from the first hole transport layer HTL1 toward the third hole transport layer HTL3. In the fourth hole transport layer HTL4, the amount of the compound represented by Formula 2 among the amount of the total fourth hole transport layer HTL4 may be gradually reduced in a direction from the third hole transport layer HTL3 toward the first hole transport layer HTL1.

The fourth hole transport layer HTL4 may have a value between the first refractive index of the first hole transport layer HTL1 and the third refractive index of the third hole transport layer HTL3 at a wavelength of about 460 nm. The refractive index of the fourth hole transport layer HTL4 may be gradually increased in a direction from the first hole transport layer HTL1 to the third hole transport layer HTL3.

In an embodiment, the fifth hole transport layer HTL5 may include both the amine compound represented by Formula 1 and included in the second hole transport layer HTL2, and the compound represented by Formula 2 and included in the third hole transport layer HTL3. In the fifth hole transport layer HTL5, the amount of the amine compound represented by Formula 1 at a portion adjacent to the second hole transport layer HTL2 may be greater than the amount of the amine compound represented by Formula 1 at a portion adjacent to the third hole transport layer HTL3. In the fifth hole transport layer HTL5, the amount of the compound represented by Formula 2 at a portion adjacent to the third hole transport layer HTL3 may be greater than the amount of the compound represented by Formula 2 at a portion adjacent to the second hole transport layer HTL2. For example, the fifth hole transport layer HTL5 is a layer including both the compound forming the second hole transport layer HTL2 and the compound forming the third hole transport layer HTL3, and in the fifth hole transport layer HTL5, the amount of the amine compound represented by Formula 1 among the amount of the total fifth hole transport layer HTL5 may be gradually reduced in a direction from the second hole transport layer HTL2 toward the third hole transport layer HTL3. In the fifth hole transport layer HTL5, the amount of the compound represented by Formula 2 among the amount of the total fifth hole transport layer HTL5 may be gradually reduced in a direction from the third hole transport layer HTL3 toward the second hole transport layer HTL2.

The fifth hole transport layer HTL5 may have a value between the second refractive index of the second hole transport layer HTL2 and the third refractive index of the third hole transport layer HTL3 at a wavelength of about 460 nm. The refractive index of the fifth hole transport layer HTL5 may be gradually increased in a direction from the second hole transport layer HTL2 to the third hole transport layer HTL3.

In an embodiment including the first to fifth hole transport layers HTL1 to HTL5, a thickness of each of the first to fifth hole transport layers HTL1 to HTL 5 may each be in a range of about 100 Å to about 1,000 Å. The thicknesses of the first to fifth hole transport layers HTL1 to HTL5 may be the same, or at least one thereof may be different from the thicknesses of the remainder. The thicknesses of the first to fifth hole transport layers HTL1 to HTL5 may be the combination of various types according to the properties of the light emitting diode required.

Referring to FIG. 3 again, the display device DD of an embodiment may include the first to third light emitting diodes OEL-1, OEL-2, and OEL-3 divided by the pixel defining layer PDL, and the first to third light emitting diodes OEL-1, OEL-2, and OEL-3 may have different configurations of the emission layers EML-B, EML-G, and EML-R and may emit light in different wavelength regions. One light emitting diode among the first to third light emitting diodes OEL-1, OEL-2, and OEL-3 may have the configurations of the light emitting diodes of FIG. 4 to FIG. 6. In another embodiment, two light emitting diodes or three light emitting diodes selected among the first to third light emitting diodes OEL-1, OEL-2, and OEL-3 may have the configurations of the light emitting diodes of FIG. 4 to FIG. 6.

In the display device DD of an embodiment, in a case where all three light emitting diodes OEL-1, OEL-2, and OEL-3 have the configuration of the light emitting diode of FIG. 4 and FIG. 5, the hole transport region HTR may be provided as a common layer for all the first to third light emitting diodes OEL-1, OEL-2, and OEL-3. For example, the hole transport region HTR provided as the common layer may have a structure including the first to third hole transport layers HTL1, HTL2, and HTL3.

In the display device of an embodiment, in contrast to FIG. 3, the hole transport region HTR may be disposed in the opening portion OH defined in the pixel defining layer PDL and may be separately provided corresponding to emission layers EML-B, EML-G, and EML-R. The hole transport region HTR included in each of the light emitting diodes OEL-1, OEL-2, and OEL-3 may also have a structure including the first to third hole transport layers HTL1, HTL2, and HTL3. If the hole transport region HTR is provided not as a common layer but separately corresponding to the light emitting diodes OEL-1, OEL-2, and OEL-3, a thickness ratio of the first to third hole transport layers HTL1, HTL2, and HTL3 included in the light emitting diodes OEL-1, OEL-2, and OEL-3 may be controlled differently according to the wavelength region of light emitted from each of the light emitting diodes OEL-1, OEL-2, and OEL-3.

In another embodiment, in the display device DD of an embodiment, the first light emitting diode OEL-1 emitting blue light may have a light emitting diode structure including the first to third hole transport layers HTL1, HTL2 and HTL3. However, an embodiment of the inventive concept is not limited thereto.

In the display device DD of an embodiment shown in FIG. 3, the hole transport region HTR may have the structure of the hole transport region HTR-a shown in FIG. 6. The hole transport region HTR-a including the first to fifth hole transport layers HTL1 to HTL5 may be provided as a common layer for the whole first to third light emitting diodes OEL-1, OEL-2, and OEL-3. In another embodiment, the display device of an embodiment may include the hole transport region HTR-a disposed in the opening portion OH defined by the pixel defining layer PDL and separately provided corresponding to the emission layers EML-B, EML-G, and EML-R. For example, the hole transport region HTR-a included in each of the light emitting diodes OEL-1, OEL-2, and OEL-3 may have a structure including the first to fifth hole transport layers HTL1 to HTL5.

Figure 7:
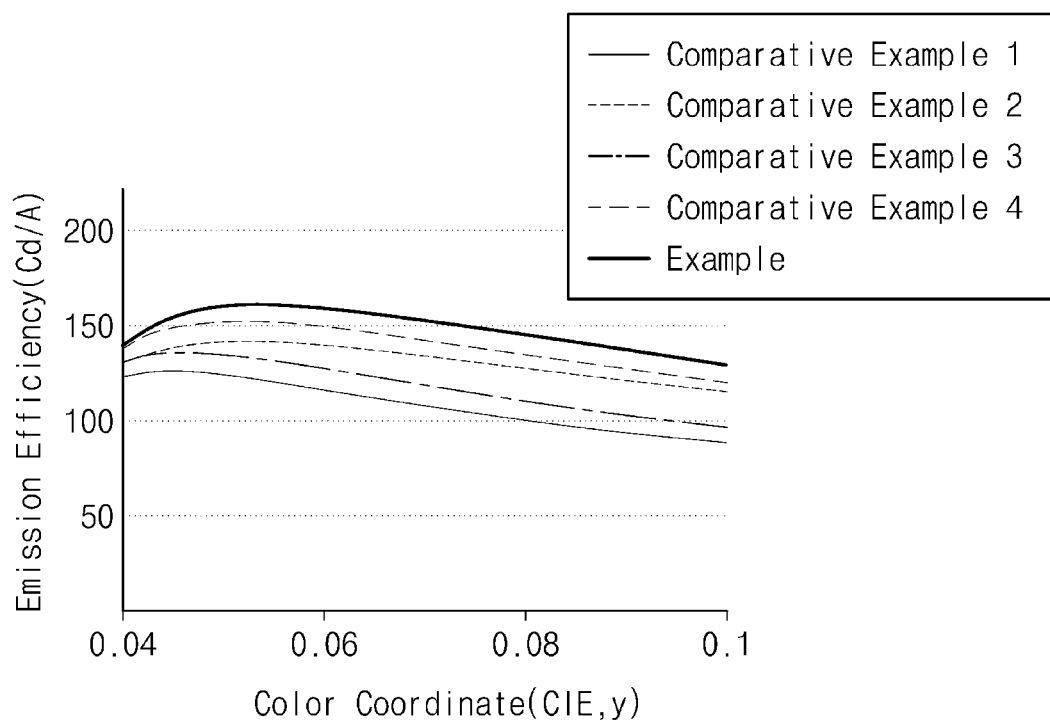
FIG. 7 is a graph comparing and showing efficiency properties of light emitting diodes of the Comparative Examples and the Example.

FIG. 7 is a graph comparing and showing emission efficiency of the Comparative Examples and the Example. The Example corresponds to evaluation results on a light emitting diode having the above-described hole transport region structure of the light emitting diode of an embodiment, and Comparative Example 1 to Comparative Example 4 correspond to evaluation results on light emitting diodes having different configurations of the hole transport regions from the Example. Except for the different configurations of the hole transport regions, the configurations of other functional layers were the same in the Comparative Examples and the Example. The Comparative Examples and the Example correspond to light emitting diodes emitting blue light having a central wavelength around 464 nm.

Comparative Example 1 and Comparative Example 2 correspond to cases where the hole transport region is formed of one hole transport layer. Comparative Example 1 corresponds to a case of including only one hole transport layer having a refractive index of about 1.9, and Comparative Example 2 corresponds to a case of including only one hole transport layer having a refractive index of about 1.4.

Comparative Example 3 and Comparative Example 4 correspond to cases where the hole transport region is formed of two hole transport layers. Comparative Example 3 corresponds to a case where the refractive index of a hole transport layer adjacent to a first electrode is about 1.4, and the refractive index of a hole transport layer adjacent to an emission layer is about 1.9. Comparative Example 4 corresponds to a case where the refractive index of a hole transport layer adjacent to a first electrode is about 1.9, and the refractive index of a hole transport layer adjacent to an emission layer is about 1.4. Comparative Example 3 and Comparative Example 4 correspond to cases having different stacking order of the hole transport layer of a low refractive index and the hole transport layer of a high refractive index.

The Example corresponds to a case of including the aforementioned hole transport region structure of the light emitting diode and includes three hole transport layers, wherein the refractive indexes of a first hole transport layer adjacent to a first electrode and a second hole transport layer adjacent to an emission layer are about 1.4, and the refractive index of a third hole transport layer disposed between the first hole transport layer and the second hole transport layer is about 1.9.

In FIG. 7, the horizontal axis represents color coordinate values and corresponds to "y" values of the color coordinate of light emitted from a light emitting diode. In FIG. 7, the value shown in the horizontal axis corresponds to the y value in a CIE color coordinate. The graph of FIG. 7 represents emission efficiency according to the color coordinates of light emitted. Referring to the results of FIG. 7, it could be found that the light emitting diode of the Example shows higher emission efficiency when compared with the Comparative Examples in a range of a color coordinate value of about 0.04 to about 0.1. The Example showed improving effects of emission efficiency by about 34% when compared with Comparative Example 1.

Hereinafter, referring to embodiments and comparative embodiments, the light emitting diode according to an embodiment of the inventive concept will be explained. The following embodiments are only illustrations to assist the understanding of the inventive concept, and the scope of the inventive concept is not limited thereto.

EXAMPLES

1. Synthesis of Amine Compound

First, the synthesis method of an amine compound according to an embodiment will be explained to illustrate the synthesis methods of Compound 7, Compound 11, Compound 22, Compound 38, Compound 51, Compound 57, Compound 72, Compound 83, Compound 89, and Compound 95 in Compound Group 1. The synthesis methods of the amine compounds explained hereinafter are embodiments, and the synthesis method of the amine compound according to an embodiment is not limited thereto.

<Synthesis of Compound 7>

Amine Compound 7 according to an embodiment may be synthesized, for example, by the steps of Reaction 1 below.

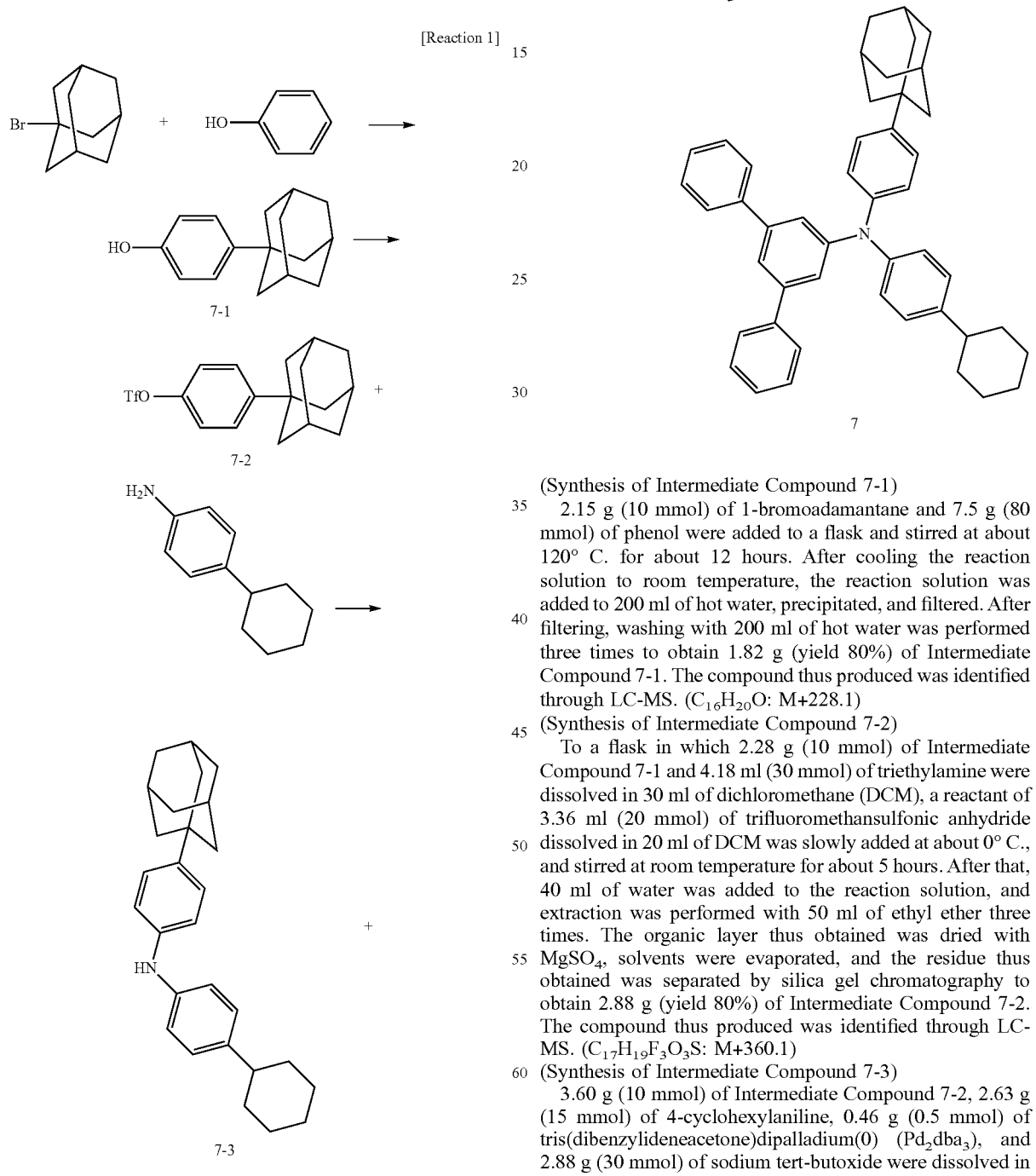

(Synthesis of Intermediate Compound 7-1)

2.15 g (10 mmol) of 1-bromoadamantane and 7.5 g (80 mmol) of phenol were added to a flask and stirred at about 120° C. for about 12 hours. After cooling the reaction solution to room temperature, the reaction solution was added to 200 ml of hot water, precipitated, and filtered. After filtering, washing with 200 ml of hot water was performed three times to obtain 1.82 g (yield 80%) of Intermediate Compound 7-1. The compound thus produced was identified through LC-MS. ($C_{16}H_{20}O$: M+228.1)

(Synthesis of Intermediate Compound 7-2)

To a flask in which 2.28 g (10 mmol) of Intermediate Compound 7-1 and 4.18 ml (30 mmol) of triethylamine were dissolved in 30 ml of dichloromethane (DCM), a reactant of 3.36 ml (20 mmol) of trifluoromethansulfonic anhydride dissolved in 20 ml of DCM was slowly added at about 0° C., and stirred at room temperature for about 5 hours. After that, 40 ml of water was added to the reaction solution, and extraction was performed with 50 ml of ethyl ether three times. The organic layer thus obtained was dried with $MgSO_4$, solvents were evaporated, and the residue thus obtained was separated by silica gel chromatography to obtain 2.88 g (yield 80%) of Intermediate Compound 7-2. The compound thus produced was identified through LC-MS. ($C_{17}H_{19}F_3O_3S$: M+360.1)

(Synthesis of Intermediate Compound 7-3)

3.60 g (10 mmol) of Intermediate Compound 7-2, 2.63 g (15 mmol) of 4-cyclohexylaniline, 0.46 g (0.5 mmol) of tris(dibenzylideneacetone)dipalladium(0) ($Pd_2dba_3$), and 2.88 g (30 mmol) of sodium tert-butoxide were dissolved in 60 ml of toluene, and stirred at about 80° C. for about 3 hours. After cooling the reaction solution to room temperature, 40 ml of water was added, and extraction with 50 ml of ethyl ether was carried out three times. The organic layer thus collected was dried with MgSO$_4$, and solvents were evaporated. The residue thus obtained was separated by silica gel chromatography to obtain 2.70 g (yield 70%) of Intermediate Compound 7-3. The compound thus produced was identified through LC-MS. (C$_{28}$H$_{35}$N: M+385.2)

(Synthesis of Compound 7)

3.85 g (10 mmol) of Intermediate Compound 7-3, 3.09 g (10 mmol) of 5'-bromo-1,1':3',1''-terphenyl, 0.46 g (0.5 mmol) of tris(dibenzylideneacetone)dipalladium(0) (Pd$_2$dba$_3$), and 2.88 g (30 mmol) of sodium tert-butoxide were dissolved in 60 ml of toluene and stirred at about 80° C. for about 3 hours. After cooling the reaction solution to room temperature, 40 ml of water was added, and extraction with 50 ml of ethyl ether was performed three times. The organic layer thus obtained was dried with MgSO$_4$, and solvents were evaporated. The residue thus obtained was separated by silica gel chromatography to obtain 4.30 g (yield 70%) of Compound 7. The compound thus produced was identified through MS/FAB and 1H NMR. (C$_{46}$H$_{47}$N: M+cal.:613.37, found:613.27)

<Synthesis of Compound 11>

Amine Compound 11 according to an embodiment was synthesized by the same synthesis method of Compound 7 except for using 2-bromo-9,9-dimethyl-9H-fluorene instead of 5'-bromo-1,1':3',1''-terphenyl in the synthesis method of Compound 7. The compound thus produced was identified through MS/FAB and 1H NMR. (C$_{43}$H$_{47}$N: M+cal.: 577.37, found: 577.27)

<Synthesis of Compound 22>

Amine Compound 22 according to an embodiment may be synthesized, for example, by the steps of Reaction 2 below.

[Reaction 2]

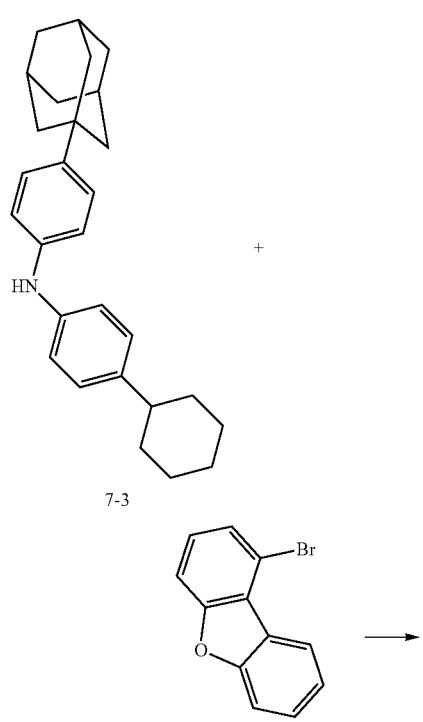

7-3

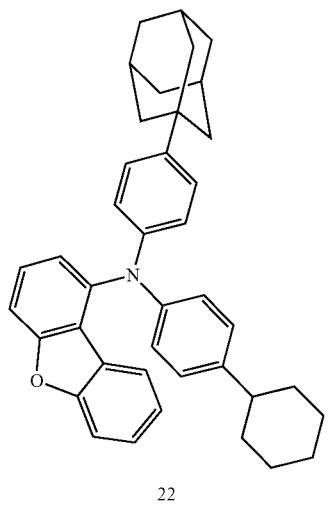

22

Amine Compound 22 according to an embodiment was synthesized by the same synthesis method of Compound 7 except for using 1-bromodibenzo[b,d]furan instead of 5'-bromo-1,1':3',1''-terphenyl in the synthesis method of Compound 7. The compound thus produced was identified through MS/FAB and 1H NMR. (C$_{40}$H$_{41}$NO: M+cal.: 551.32, found: 551.22)

<Synthesis of Compound 38>

Amine Compound 38 according to an embodiment may be synthesized, for example, by the steps of Reaction 3 below.

[Reaction 3]

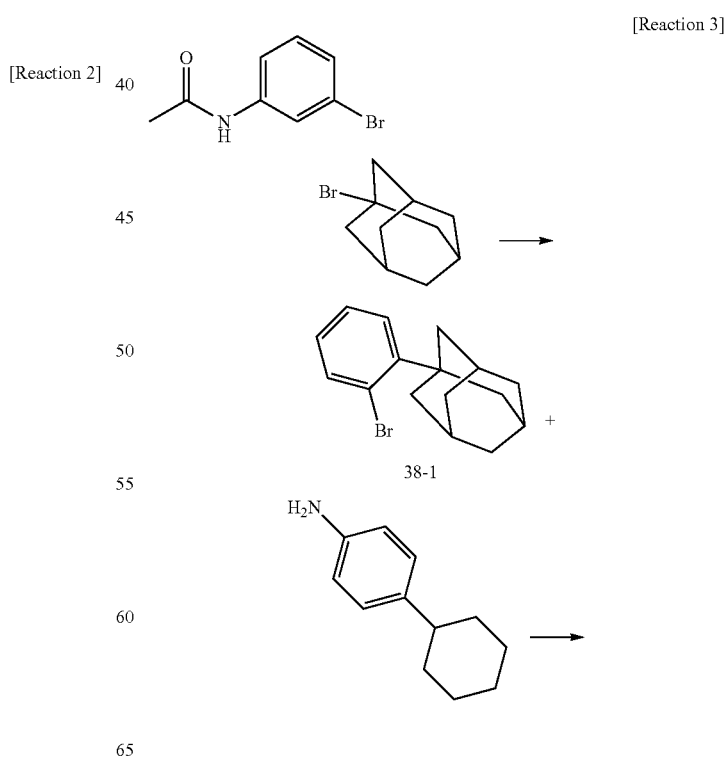

38-1

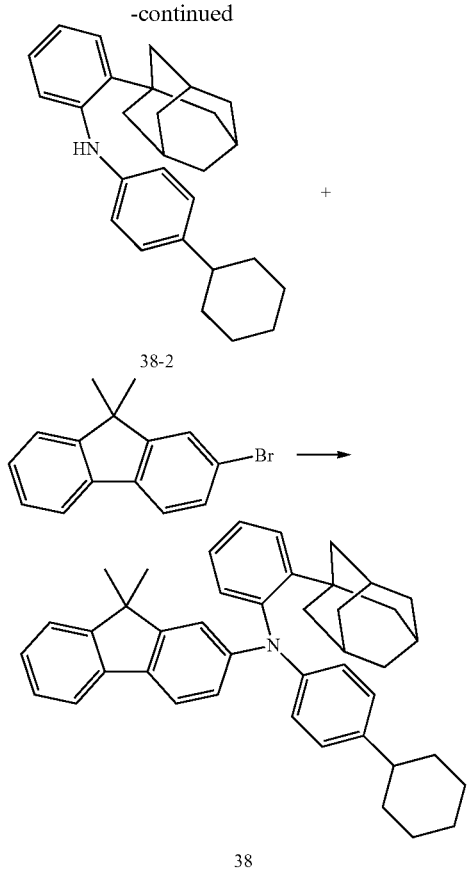

(Synthesis of Intermediate Compound 38-1)

2.15 g (10 mmol) of 1-bromoadamantane and 10.70 g (50 mmol) of N-(3-bromophenyl)acetamide were added to a flask and stirred at about 170° C. for about 18 hours. After cooling the reaction solution to room temperature, HCl (10 ml, 6 N) was added thereto and stirred at about 100° C. After about 4 hours, the reaction solution was cooled to room temperature and neutralized with NaHCO₃. The reaction solution was extracted with 50 ml of ethyl ether three times. The organic layer thus obtained was dried with MgSO₄, and solvents were evaporated. The residue thus obtained was dissolved in THF (20 ml), and isoamylnitride (1.34 ml, 10 mmol) was slowly added thereto. Stirring was carried out at about 60° C. for about 3 hours, the reaction solution was cooled to room temperature, solvents were evaporated, and the residue thus obtained was separated by silica gel chromatography to obtain 0.87 g (yield 30%) of Intermediate Compound 38-1. The compound thus produced was identified through LC-MS. ($C_{16}H_{19}Br$: M+290.0)

(Synthesis of Intermediate Compound 38-2)

2.90 g (10 mmol) of Intermediate Compound 38-1, 2.63 g (15 mmol) of 4-cyclohexylaniline, 0.46 g (0.5 mmol) of tris(dibenzylideneacetone)dipalladium(0) (Pd₂dba₃), and 2.88 g (30 mmol) of sodium tert-butoxide were dissolved in 60 ml of toluene and stirred at about 80° C. for about 3 hours. After cooling the reaction solution to room temperature, 40 ml of water was added, and extraction with 50 ml of ethyl ether was performed three times. The organic layer thus obtained was dried with MgSO₄, and solvents were evaporated. The residue thus obtained was separated by silica gel chromatography to obtain 2.70 g (yield 70%) of Intermediate Compound 38-2. The compound thus produced was identified through LC-MS. ($C_{28}H_{35}N$: M+385.2)

(Synthesis of Compound 38)

3.85 g (10 mmol) of Intermediate Compound 38-2, 2.37 g (10 mmol) of 2-bromo-9,9-dimethyl-9H-fluorene, 0.46 g (0.5 mmol) of tris(dibenzylideneacetone)dipalladium(0) (Pd₂dba₃), and 2.88 g (30 mmol) of sodium tert-butoxide were dissolved in 60 ml of toluene and stirred at about 80° C. for about 3 hours. After cooling the reaction solution to room temperature, 40 ml of water was added, and extraction with 50 ml of ethyl ether was performed three times. The organic layer thus obtained was dried with MgSO₄, and solvents were evaporated. The residue thus obtained was separated by silica gel chromatography to obtain 4.05 g (yield 70%) of Compound 38. The compound thus produced was identified through MS/FAB and 1H NMR. ($C_{43}H_{47}N$: M+cal.:577.37, found:577.27)

<Synthesis of Compound 51>

Amine Compound 51 according to an embodiment may be synthesized, for example, by the steps of Reaction 4 below.

[Reaction 4]

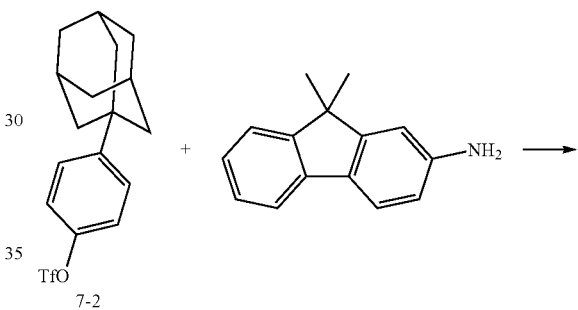

7.20 g (20 mmol) of Intermediate Compound 7-2, 2.09 g (10 mmol) of 2-amino-9,9-dimethyl-9H-fluorene, 0.46 g (0.5 mmol) of tris(dibenzylideneacetone)dipalladium(0) (Pd₂dba₃), and 2.88 g (30 mmol) of sodium tert-butoxide were dissolved in 60 ml of toluene, and stirred at about 80° C. for about 3 hours. After cooling the reaction solution to room temperature, 40 ml of water was added, and extraction with 50 ml of ethyl ether was performed three times. The organic layer thus obtained was dried with MgSO₄, and solvents were evaporated. The residue thus obtained was separated by silica gel chromatography to obtain 4.36 g (yield 70%) of Compound 51. The compound thus produced was identified through MS/FAB and 1H NMR. (C$_{47}$H$_{51}$N: M+cal.:629.40, found:629.30)

<Synthesis of Compound 57>

Amine Compound 57 according to an embodiment may be synthesized, for example, by the steps of Reaction 5 below.

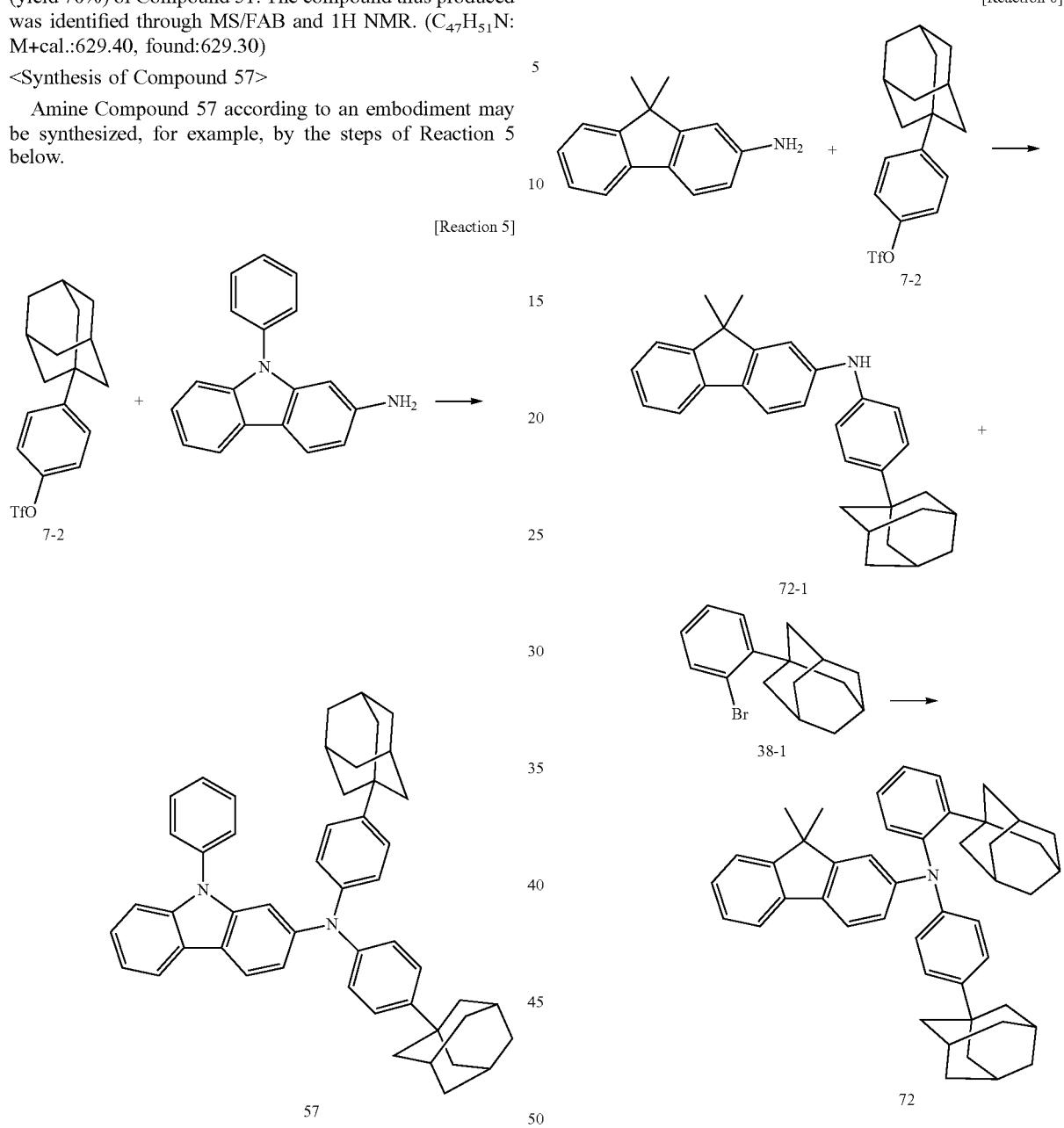

Amine Compound 57 was synthesized by the same synthesis method of Compound 51 except for using 9-phenyl-9H-carbazol-2-amine instead of 2-amino-9,9-dimethyl-9H-fluorene in the synthesis method of Compound 51. The compound thus produced was identified through MS/FAB and 1H NMR. (C$_{50}$H$_{50}$N$_2$: M+cal.: 678.40, found: 678.40)

<Synthesis of Compound 72>

Amine Compound 72 according to an embodiment may be synthesized, for example, by the steps of Reaction 6 below.

(Synthesis of Intermediate Compound 72-1)

3.60 g (10 mmol) of Intermediate Compound 7-2, 3.14 g (15 mmol) of 2-amino-9,9-dimethyl-9H-fluorene, 0.46 g (0.5 mmol) of tris(dibenzylideneacetone)dipalladium(0) (Pd$_2$dba$_3$), and 2.88 g (30 mmol) of sodium tert-butoxide were dissolved in 60 ml of toluene and stirred at about 80° C. for about 3 hours. After cooling the reaction solution to room temperature, 40 ml of water was added, and extraction with 50 ml of ethyl ether was performed three times. The organic layer thus obtained was dried with MgSO$_4$, and solvents were evaporated. The residue thus obtained was separated by silica gel chromatography to obtain 2.94 g (yield 70%) of Intermediate Compound 72-1. The compound thus produced was identified through LC-MS. (C$_{31}$H$_{33}$N: M+419.2)

(Synthesis of Compound 72)

4.20 g (10 mmol) of Intermediate Compound 72-1, 2.91 g (10 mmol) of Intermediate Compound 38-1, 0.46 g (0.5 mmol) of tris(dibenzylideneacetone)dipalladium(0) (Pd$_2$dba$_3$), and 2.88 g (30 mmol) of sodium tert-butoxide were dissolved in 60 ml of toluene and stirred at about 80° C. for about 3 hours. After cooling the reaction solution to room temperature, 40 ml of water was added, and extraction with 50 ml of ethyl ether was performed three times. The organic layer thus obtained was dried with MgSO$_4$, and solvents were evaporated. The residue thus obtained was separated by silica gel chromatography to obtain 4.41 g (yield 70%) of Compound 72. The compound thus produced was identified through MS/FAB and 1H NMR. (C$_{47}$H$_{51}$N: M+cal.:629.40, found:629.30)

<Synthesis of Compound 83>

Amine Compound 83 according to an embodiment may be synthesized, for example, by the steps of Reaction 7 below.

[Reaction 7]

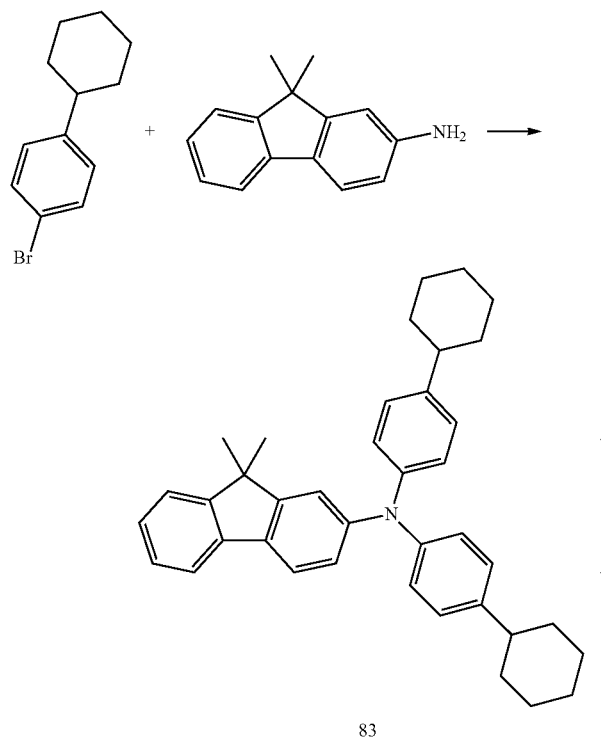

83

4.78 g (20 mmol) of 1-bromo-4-cyclohexylbenzene, 2.09 g (10 mmol) of 2-amino-9,9-dimethyl-9H-fluorene, 0.46 g (0.5 mmol) of tris(dibenzylideneacetone)dipalladium(0) (Pd$_2$dba$_3$), and 2.88 g (30 mmol) of sodium tert-butoxide were dissolved in 60 ml of toluene and stirred at about 80° C. for about 3 hours. After cooling the reaction solution to room temperature, 40 ml of water was added, and extraction with 50 ml of ethyl ether was performed three times. The organic layer thus obtained was dried with MgSO$_4$, and solvents were evaporated. The residue thus obtained was separated by silica gel chromatography to obtain 3.68 g (yield 70%) of Compound 83. The compound thus produced was identified through MS/FAB and 1H NMR. (C$_{39}$H$_{43}$N: M+cal.:525.34, found:525.24)

<Synthesis of Compound 89>

Amine Compound 89 according to an embodiment may be synthesized, for example, by the steps of Reaction 8 below.

[Reaction 8]

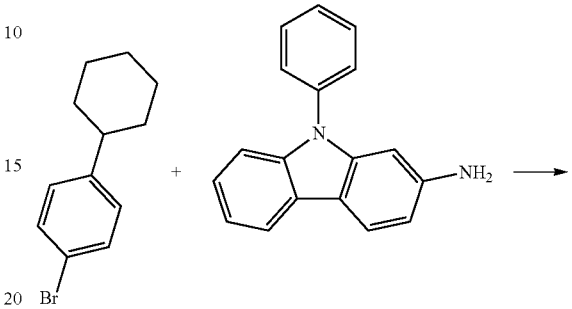

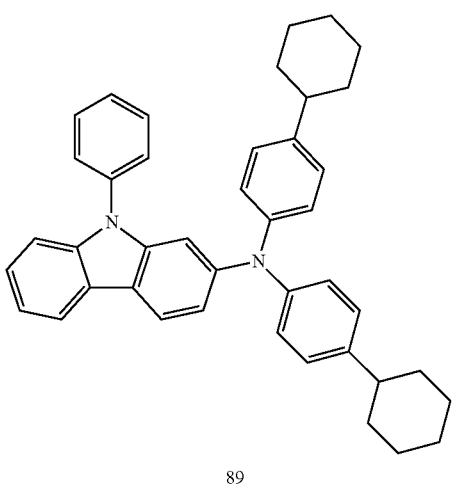

89

Amine Compound 89 was synthesized by the same synthesis method of Compound 83 except for using 9-phenyl-9H-carbazol-2-amine instead of 2-amino-9,9-dimethyl-9H-fluorene. The compound thus produced was identified through MS/FAB and 1H NMR. (C$_{42}$H$_{42}$N2: M+cal.: 574.33, found: 574.23)

<Synthesis of Compound 95>

Amine Compound 95 according to an embodiment may be synthesized, for example, by the steps of Reaction 9 below.

[Reaction 9]

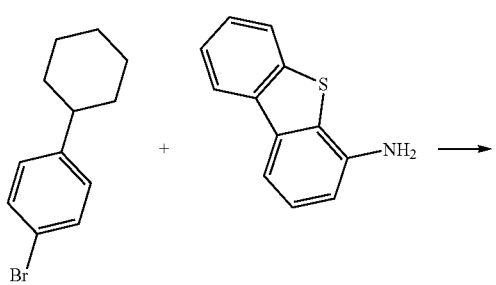

-continued

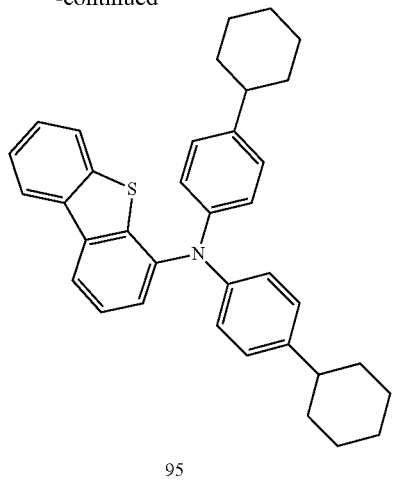

95

Amine Compound 95 was synthesized by the same synthesis method of Compound 83 except for using dibenzo[b,d]thiophen-4-amine instead of 2-amino-9,9-dimethyl-9H-fluorene. The compound thus produced was identified through MS/FAB and 1H NMR. ($C_{36}H_{37}NS$: M+cal.: 515.26, found: 515.16)

<NMR Results of Synthesized Compounds>

In Table 1 below, 1H NMR results on the compounds synthesized by the above-described synthesis methods of the compounds are shown.

An emission layer was formed using 9,10-di(naphthalene-2-yl)anthracene (ADN) doped with 3% of 2,5,8,11-tetra-t-butylperylene (TBP) into a thickness of about 250 Å. $Alq_3$ was deposited to a thickness of about 250 Å to form an electron transport layer, and LiF was deposited to a thickness of about 10 Å to form an electron injection layer.

After that, AgMg was provided to a thickness of about 1,000 Å to form a second electrode. On the second electrode, a capping layer including a compound of P4 below was formed to a thickness of about 600 Å.

P4

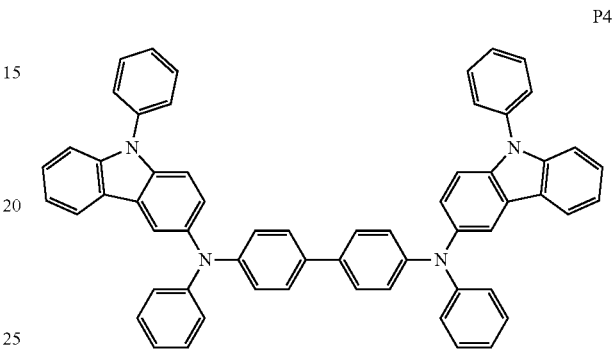

In the Example, the first electrode, the hole injection layer, the hole transport region, the emission layer, the electron transport layer, the electron injection layer and the second electrode were formed using a vacuum deposition apparatus.

TABLE 1

| Compound | $^1$H NMR (CDCl$_3$, 400 MHz) |
|---|---|
| Compound 7 | 7.75(d, 4H), 7.60(s, 1H), 7.49-7.37(m, 8H), 7.18(d, 2H), 7.10-7.06(m, 6H), 2.72(m, 1H), 2.05(d, 3H), 1.87-1.43(m, 22H) |
| Compound 11 | 7.90(d, 1H), 7.86(d, 1H), 7.55(d, 1H), 7.38-7.28 (m, 3H), 7.18-7.06(m, 9H), 2.72(m, 1H), 2.05(d, 3H), 1.87-1.43(m, 28H) |
| Compound 22 | 7.98(d, 1H), 7.54(d, 1H), 7.9-7.18(m, 6H), 7.10-7.06(m, 6H), 6.91(d 1H), 2.72(m, 1H), 2.05(d, 3H), 1.87-1.43(m, 22H) |
| Compound 38 | 7.90(d, 1H), 7.86(d, 1H), 7.55(d, 1H), 7.40-7.06(m, 12H), 2.72(m, 1H), 2.05(d, 3H), 1.87-1.43(m, 28H) |
| Compound 51 | 7.90(d, 1H), 7.86(d, 1H), 7.55(d, 1H), 7.38-7.28 (m, 3H), 7.16 (d, 1H), 7.10(s, 8H), 2.05(d, 6H), 1.87-1.69(m, 30H) |
| Compound 57 | 8.55(d, 1H), 8.24(d, 1H), 7.94(d, 1H), 7.62-7.50(m, 5H), 7.35-7.25(m, 3H), 7.16-7.10(m, 9H), 2.05(d, 6H), 1.87-1.72(m, 24H) |
| Compound 72 | 7.90(d, 1H), 7.86(d, 1H), 7.55(d, 1H), 7.38-28(m, 3H), 7.40-7.09 (m, 9H), 2.05(d, 6H), 1.87-1.69(m, 30H) |
| Compound 83 | 7.90(d, 1H), 7.86(d, 1H), 7.55(d, 1H), 7.38-7.28 (m, 3H), 7.18-7.16(m, 5H), 7.06(d, 4H), 2.72(m, 2H), 1.86-1.43(m, 26H) |
| Compound 89 | 8.55(d, 1H), 8.24(d, 1H), 7.94(d, 1H), 7.62-7.50(m, 5H), 7.35-7.25(m, 3H), 7.18-7.16(m, 5H), 7.06(d, 4H), 2.72(m, 2H), 1.86-1.43(m, 20H) |
| Compound 95 | 8.45(d, 1H), 8.11(d, 1H), 7.93(d, 1H), 7.56-7.41(m, 4H), 7.18(d, 4H), 7.06(d, 4H), 2.72(m, 2H), 1.86-1.43(m, 20H) |

2. Manufacture and Evaluation of Light Emitting Diode (Manufacture of Light Emitting Diode)

On a glass substrate, a first electrode having a stacked structure of ITO/Ag/ITO was formed. A first hole transport layer was formed using the amine compound of an embodiment, represented by Formula 1, a second hole transport layer was formed using the compound represented by Formula 2, and a third hole transport layer was formed using the amine compound of an embodiment, represented by Formula 1 to form a hole transport region. The first hole transport layer was formed into a thickness of about 300 Å, the second hole transport layer was formed into a thickness of about 300 Å, and the third hole transport layer was formed into a thickness of about 800 Å.

(Evaluation of Properties of Light Emitting Diode)

In Table 2, with respect to the Examples including first to third hole transport layers, evaluation results of light emitting diodes according to the change of the refractive index values of the first to third hole transport layers are compared with those of the Comparative Example and shown. In Table 2, the emission efficiency, driving voltage, and device life of the light emitting diodes manufactured are compared with the Comparative Example and shown. In the evaluation results on properties of the Examples shown in Table 2, the emission efficiency represents relative values in case where the emission efficiency of the Comparative Example is set to 100%. The driving voltage represents relative values with respect to the driving voltage value of the Comparative Example (Ref.). The device life represents relative time until the luminance decreases to a level of about 97% of the initial luminance based on the Comparative Example.

Example 1 to Example 5 included a hole transport region having a stacked structure of first hole transport layer/third hole transport layer/second hole transport layer, and the Comparative Example corresponded to a case of including only the third hole transport layer in the hole transport region. In the configurations of the Comparative Example and the Examples, other elements except for the hole transport region were the same.

The refractive index of the third hole transport layer used in the Comparative Example and the Examples was about 1.95. The refractive index values shown in Table 2 below correspond to the refractive index values of the first and second hole transport layers in the Examples. In Example 1 to Example 5, the refractive indexes of the first and second hole transport layers were the same.

TABLE 2

| | Refractive index | Emission efficiency ratio (%) | Driving voltage difference (V) | Life ratio (%) |
|---|---|---|---|---|
| Comparative Example | — | 100 | Ref. | 100 |
| Example 1 | 1.70 | 116 | −0.1 | 267 |
| Example 2 | 1.75 | 117 | +0.3 | 58 |
| Example 3 | 1.76 | 119 | +0.3 | 28 |
| Example 4 | 1.77 | 117 | +0.2 | 159 |
| Example 5 | 1.73 | 119 | 0 | 100 |

Referring to the results of Table 2, it could be confirmed that the Examples including hole transport layers having different refractive indexes showed improved device properties of emission efficiency or device life when compared with the Comparative Example. With respect to the emission efficiency properties of the light emitting diodes, the Examples including multiple hole transport layers showed improved effects by about 16-19% when compared with the Comparative Example including one hole transport layer of a high refractive index.

The light emitting diode of an embodiment includes a hole transport region having a stacked structure of hole transport layer of a low refractive index/hole transport layer of a high refractive index/hole transport layer of a low refractive index, and may show high light extraction effects, and accordingly, excellent emission efficiency properties. The display device of an embodiment includes a light emitting diode having a hole transport region in which hole transport layers having different refractive indexes are stacked, and may show high luminance properties.

The light emitting diode of an embodiment includes multiple hole transport layers having different refractive indexes and may show improved light extraction properties.

The display device of an embodiment includes a light emitting diode including multiple hole transport layers having different refractive indexes and may show excellent emission efficiency.

Although the embodiments of the invention have been described, it is understood that the invention should not be limited to these embodiments, but that various changes and modifications can be made by one of ordinary skill in the art within the spirit and scope of the invention as hereinafter claimed.

What is claimed is:

1. An amine compound represented by Formula 1:

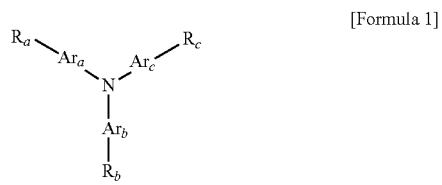

[Formula 1]

wherein in Formula 1, $Ar_a$ to $Ar_c$ are each independently a substituted or unsubstituted aryl group of 6 to 30 ring-forming carbon atoms, or a substituted or unsubstituted heteroaryl group of 3 to 30 ring-forming carbon atoms, at least two of $R_a$ to $R_c$ are each independently an adamantyl group or a cyclohexyl group, and the remainder of $R_a$ to $R_c$ is a hydrogen atom, a deuterium atom, a halogen atom, a cyano group, a substituted or unsubstituted oxy group, a substituted or unsubstituted thio group, a substituted or unsubstituted amine group, or a substituted or unsubstituted alkyl group of 1 to 20 carbon atoms.

2. The amine compound of claim 1, wherein $Ar_a$ to $Ar_c$ are each independently a substituted or unsubstituted phenyl group, a substituted or unsubstituted naphthyl group, a substituted or unsubstituted biphenyl group, a substituted or unsubstituted terphenyl group, a substituted or unsubstituted fluorenyl group, a substituted or unsubstituted carbazole group, a substituted or unsubstituted dibenzofuranyl group, or a substituted or unsubstituted dibenzothiophenyl group.

3. The amine compound of claim 1, wherein Formula 1 is represented by any one selected from Formula 1A to 1C:

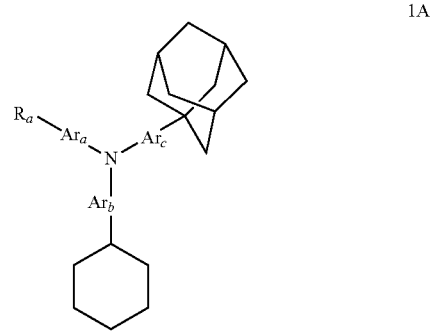

1A

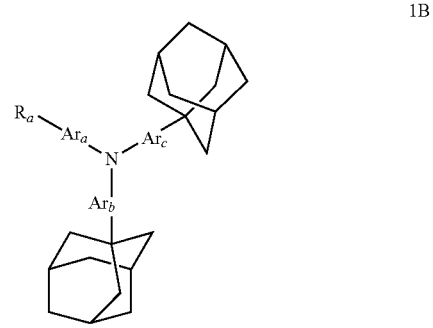

1B

-continued

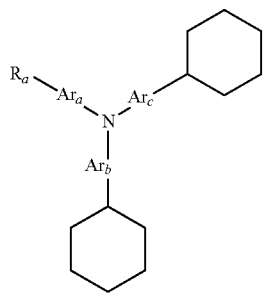

1C wherein in Formula 1A to Formula 1C, $R_a$, $Ar_a$, $Ar_b$, and $Ar_c$ are each independently the same as defined in Formula 1.

4. The amine compound of claim 1, wherein a refractive index is in a range of 1.30 to 1.80 at a wavelength of 460 nm.

5. The amine compound of claim 1, wherein the amine compound is a material for hole transport layer of a light emitting diode.

6. The amine compound of claim 1, wherein Formula 1 is any one selected from the compounds represented by Compound Group 1:

[Compound Group 1]

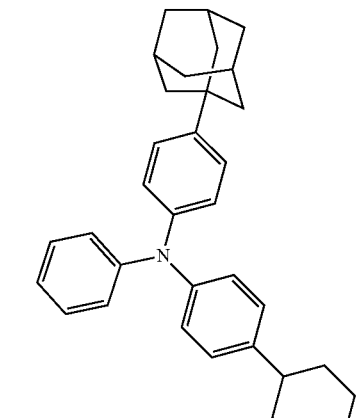

-continued

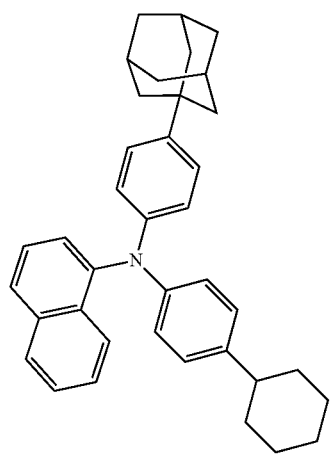

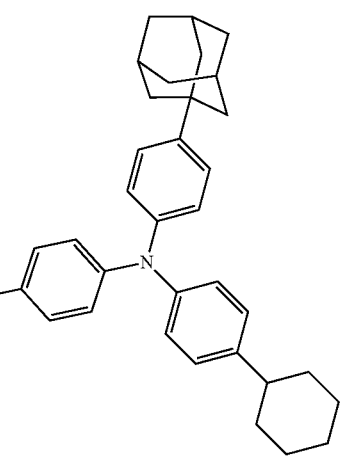

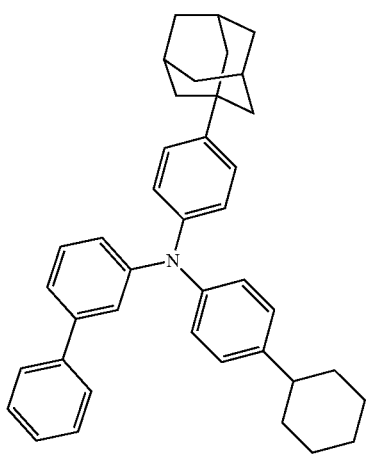

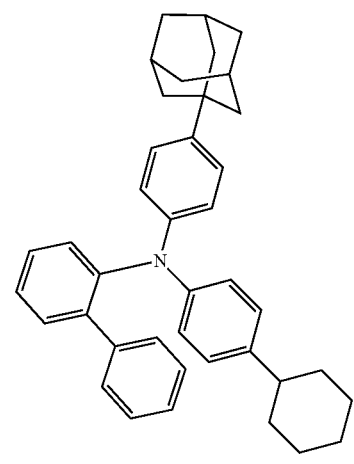
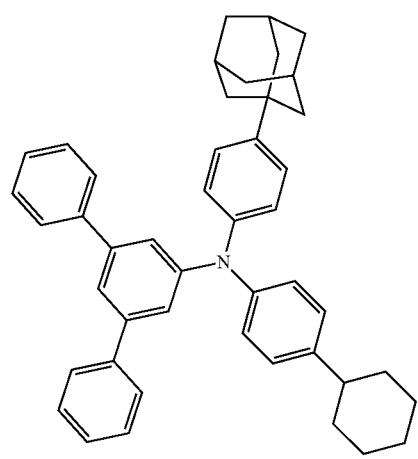
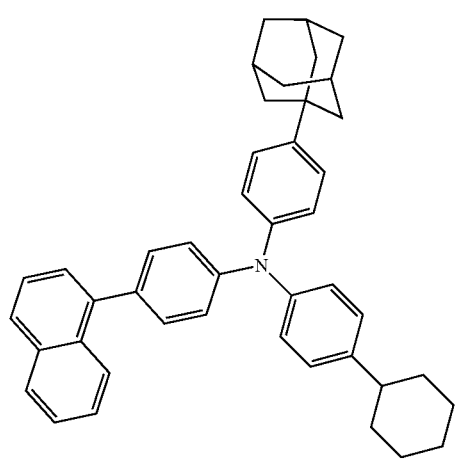
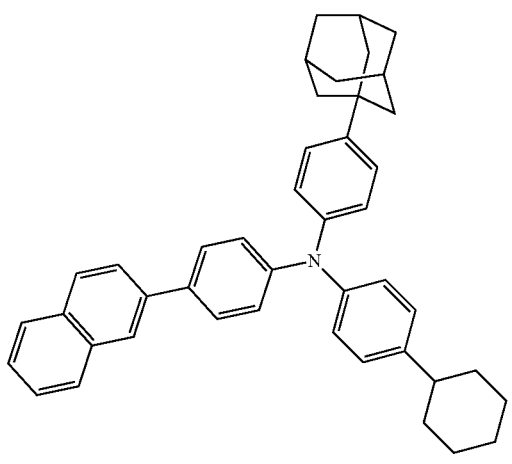
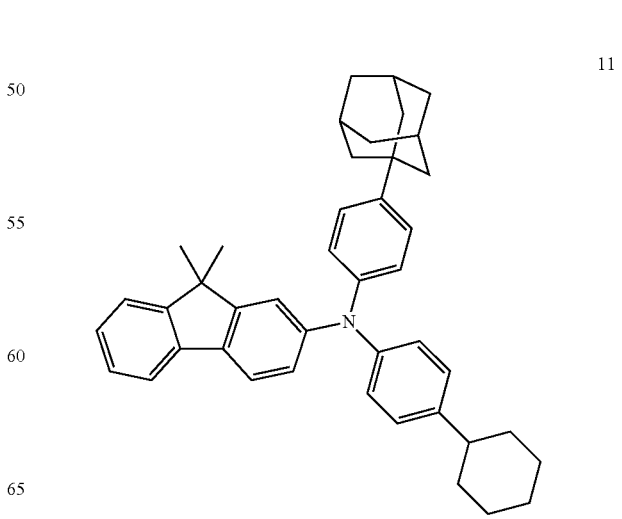

12
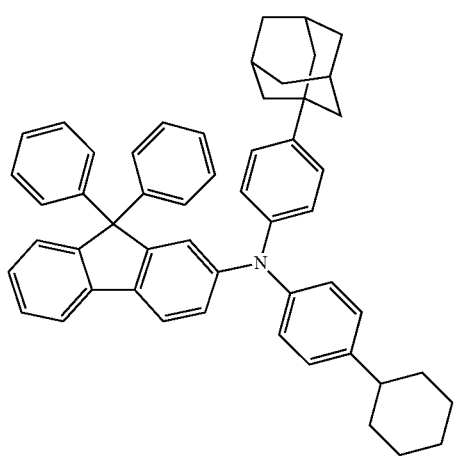
13
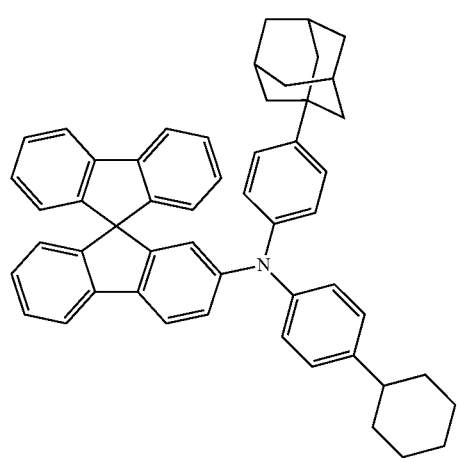
14
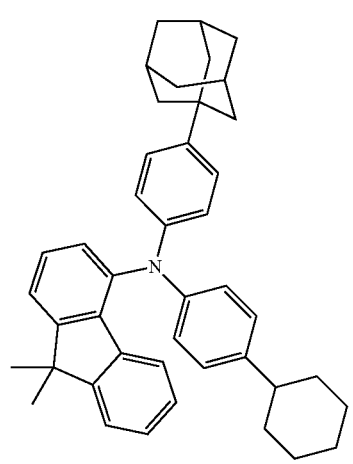
15
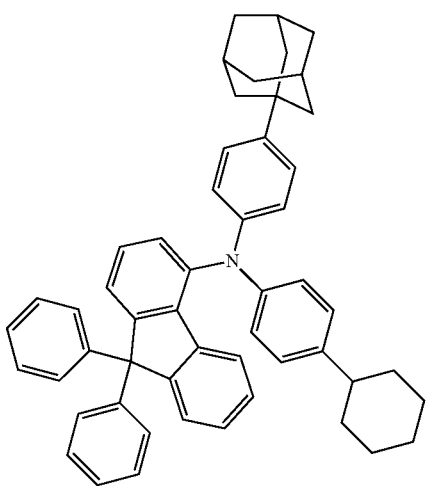
16
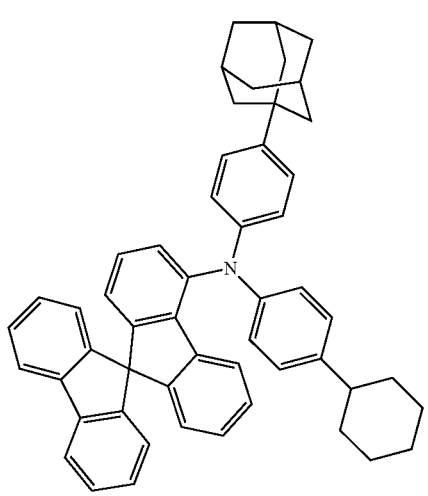
17
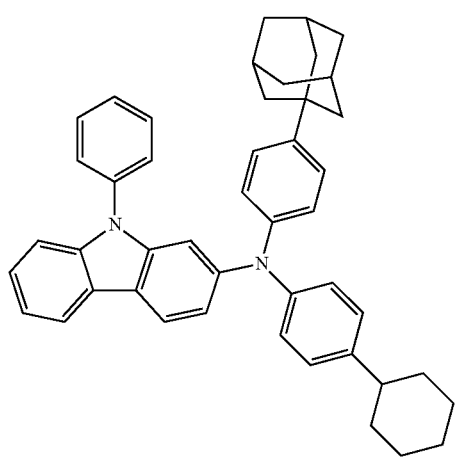

18
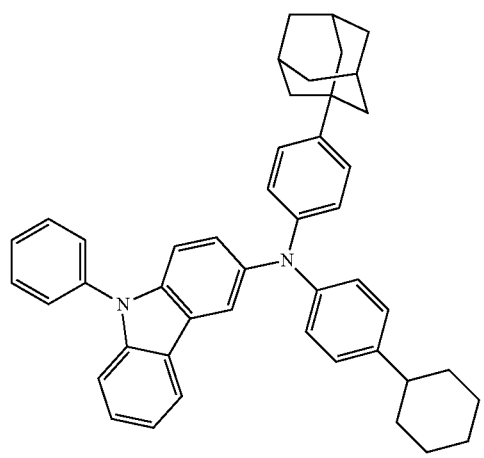
19
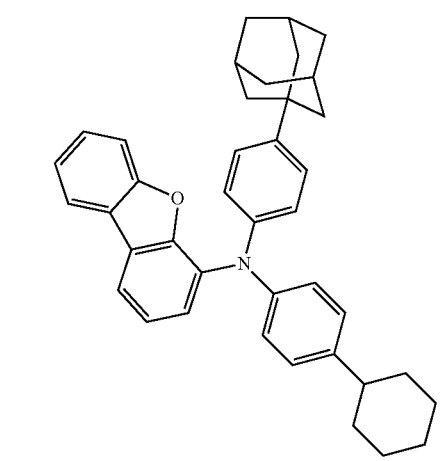
20
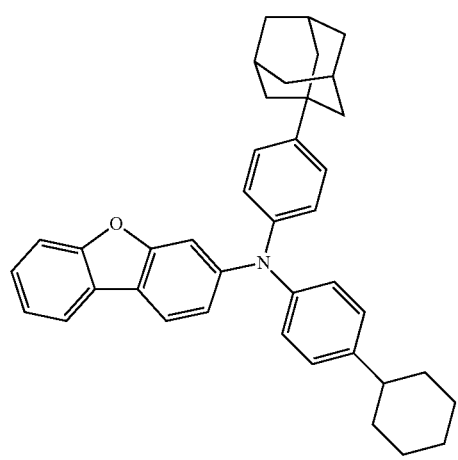
21
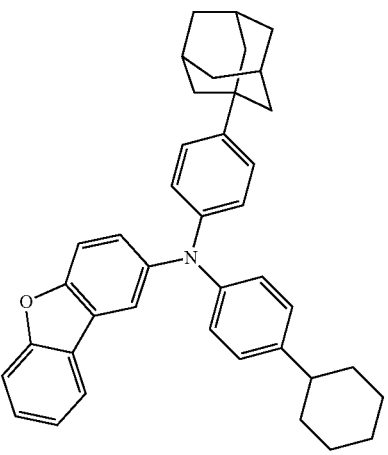
22
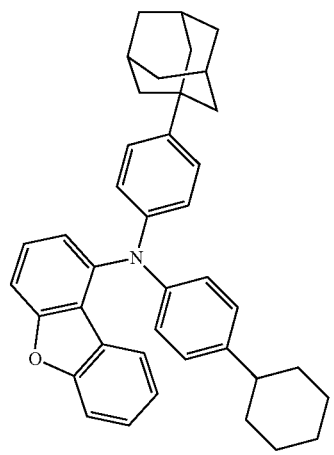
23
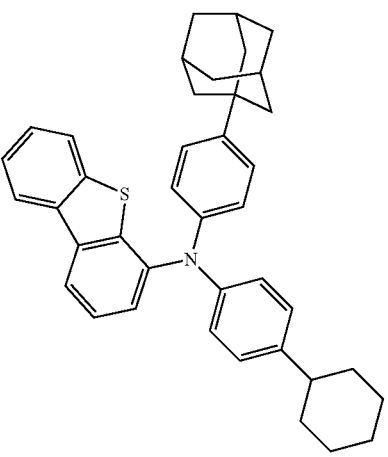

24
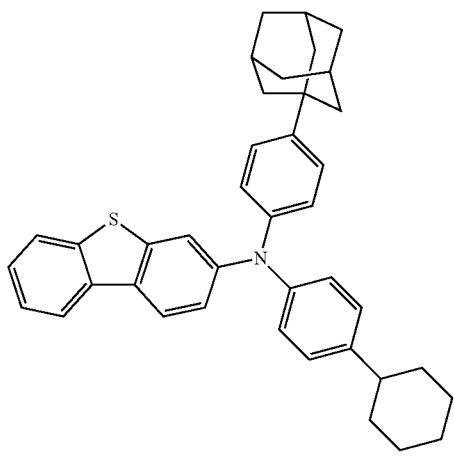
25
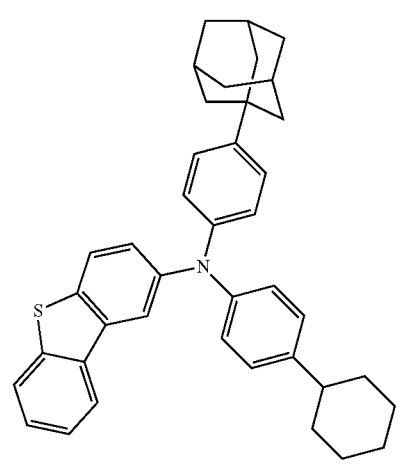
26
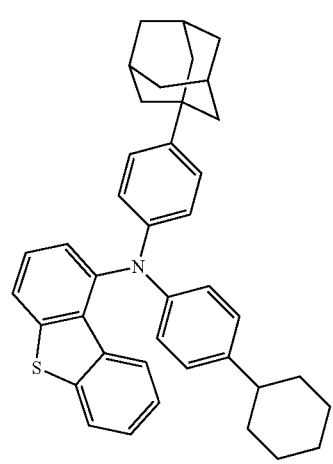
27
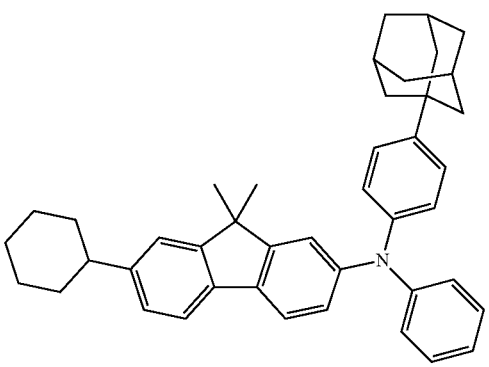
28
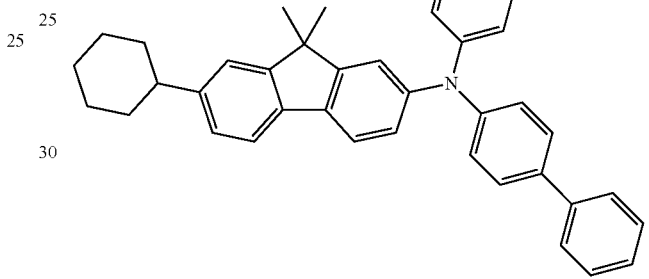
29
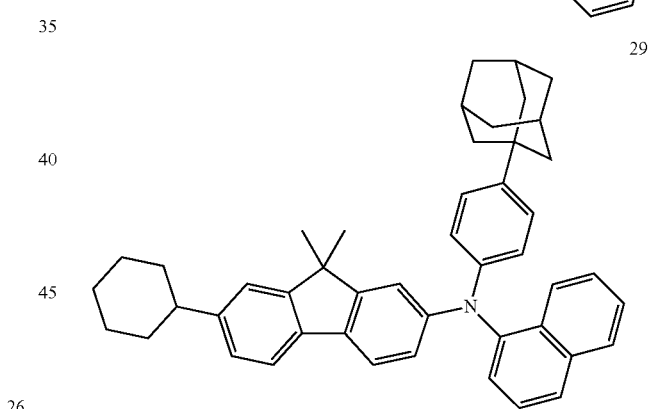
30
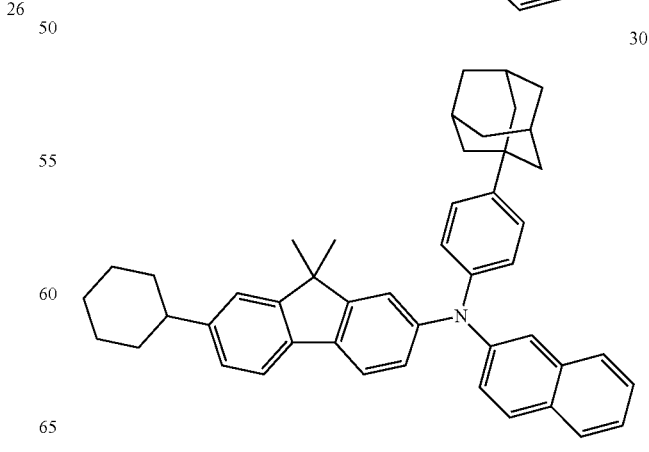

103
-continued
31
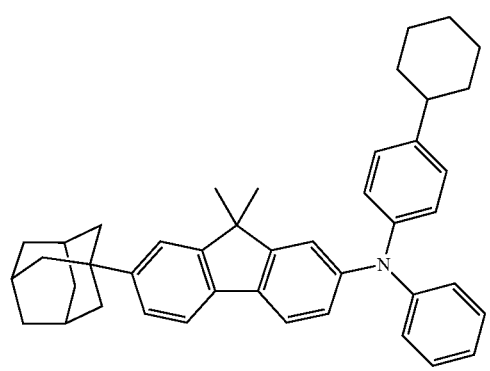
32
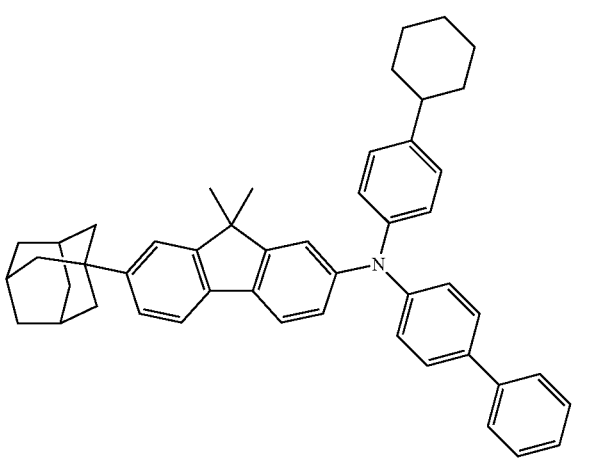
33
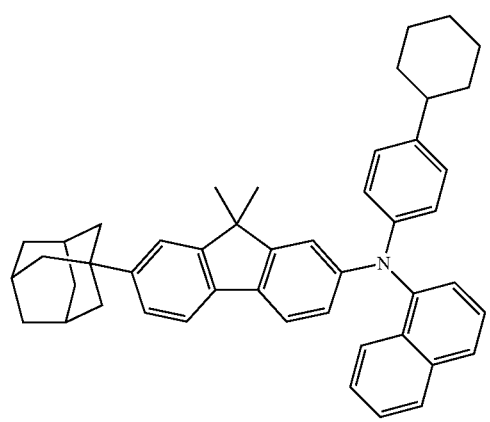
104
-continued
34
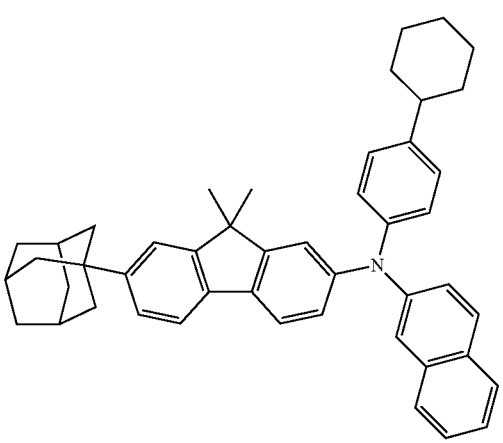
35
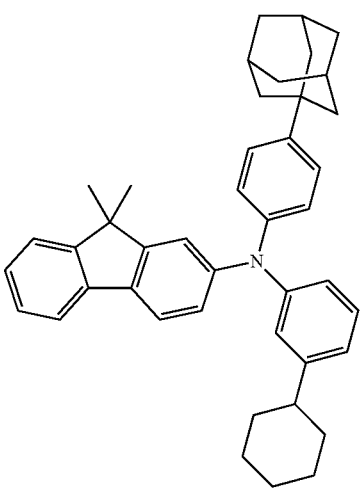
36
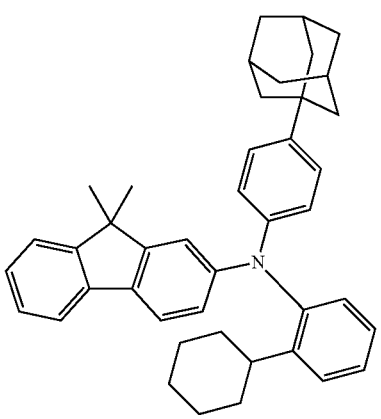

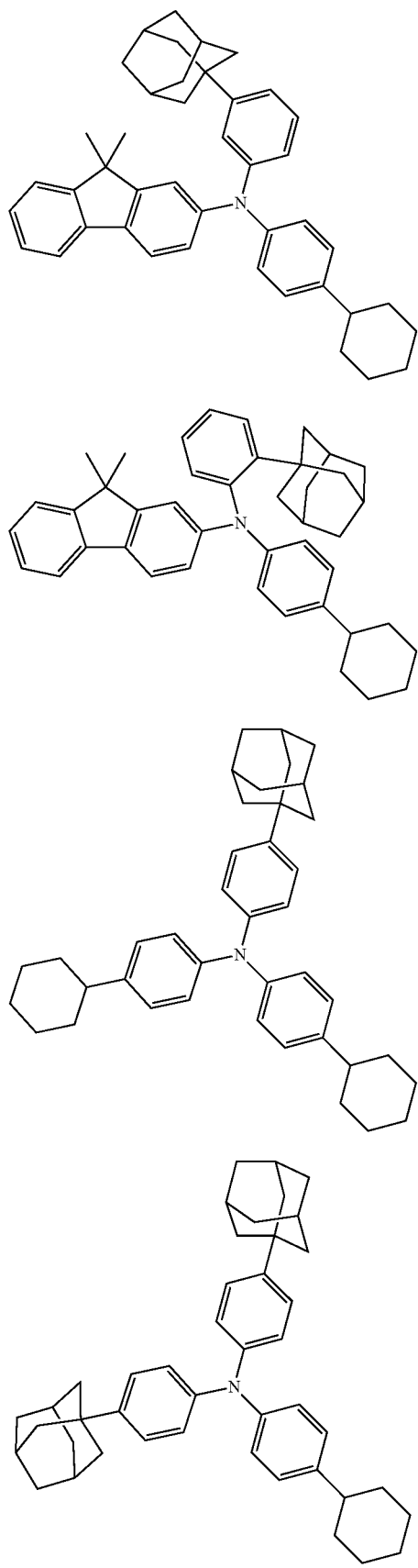
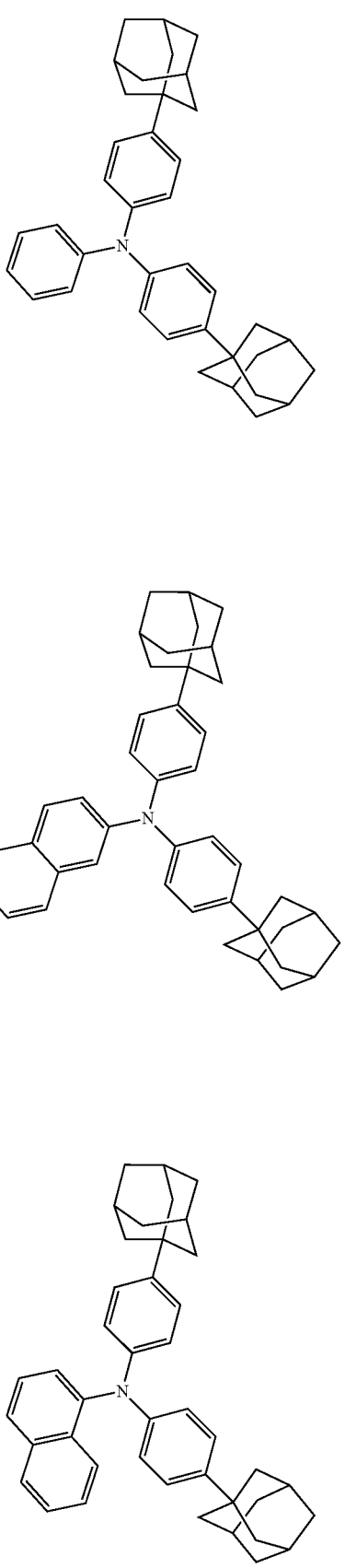

44
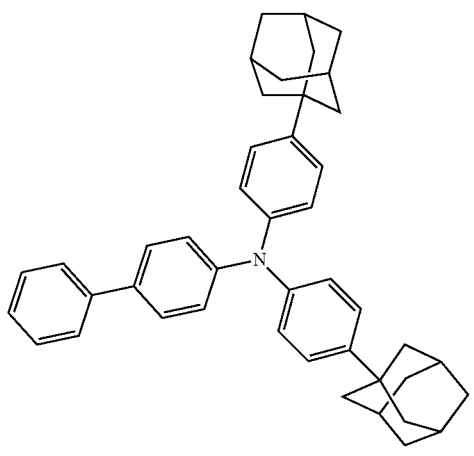
47
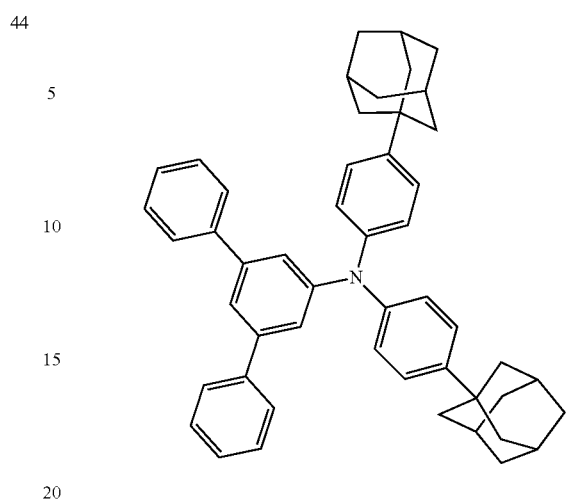
45
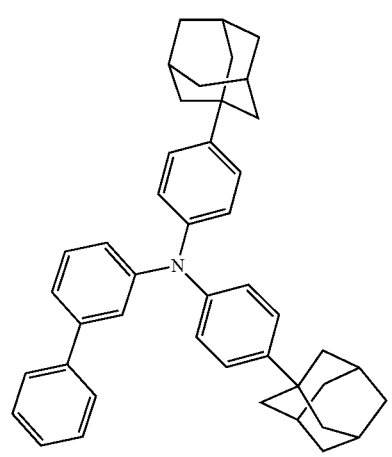
48
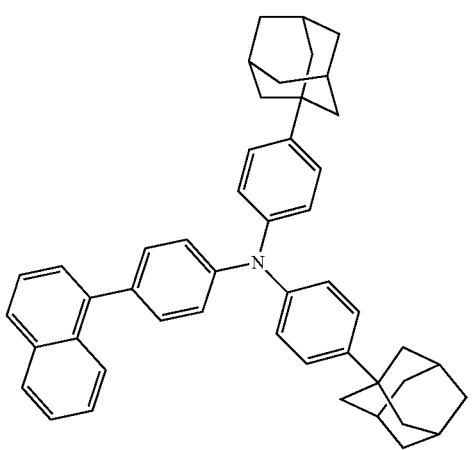
46
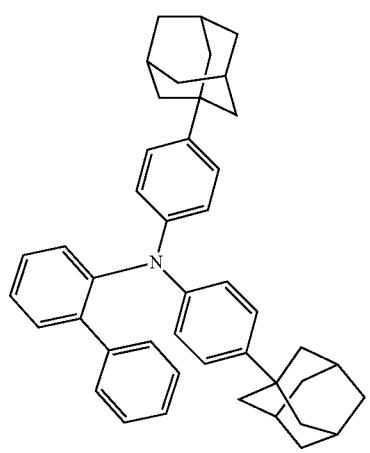
49
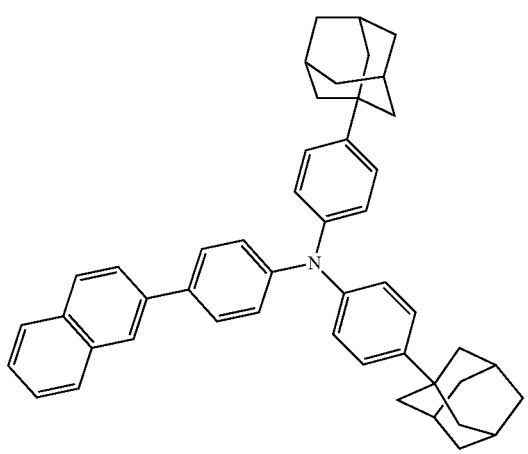

50
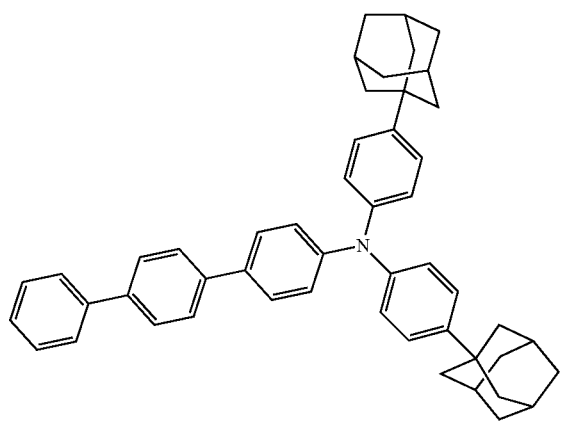
51
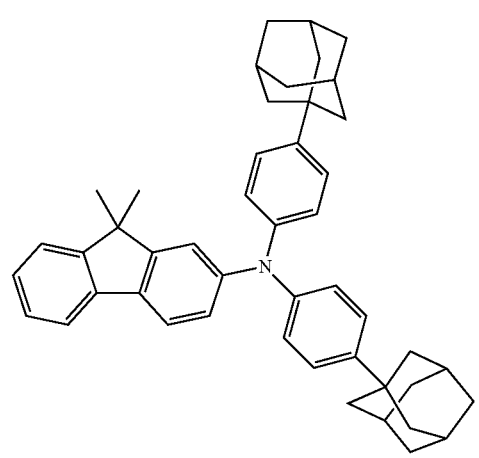
52
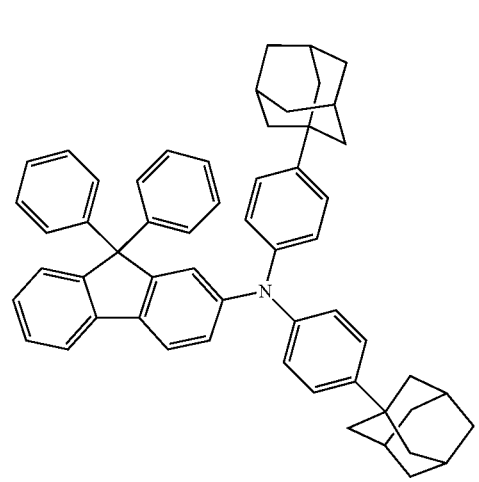
53
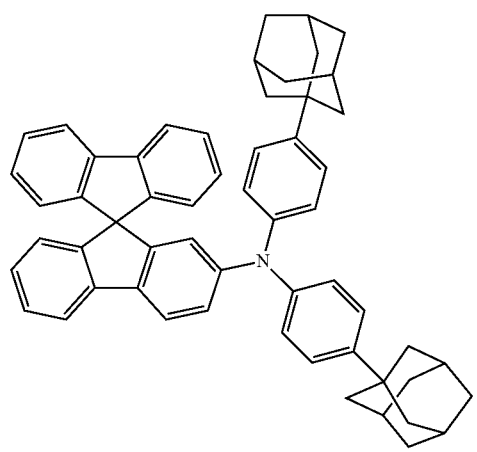
54
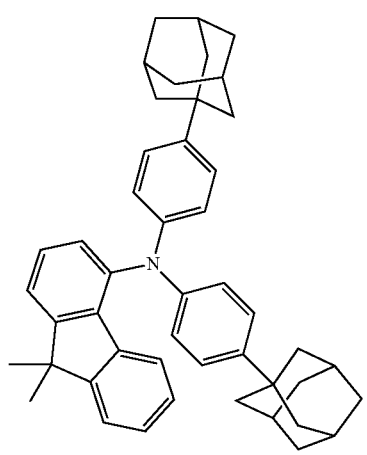
55
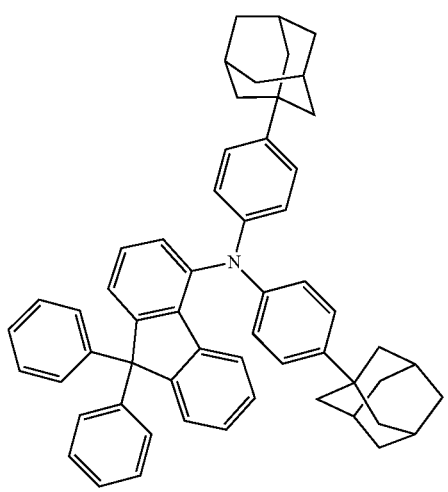

56
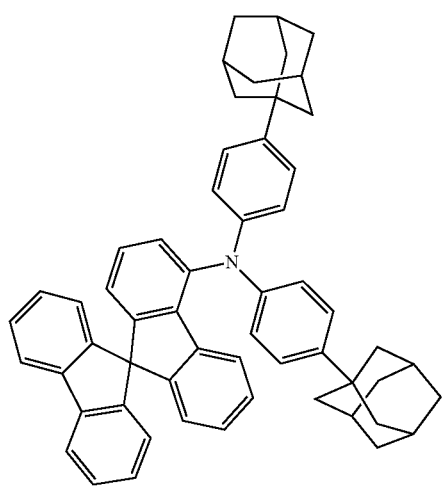
57
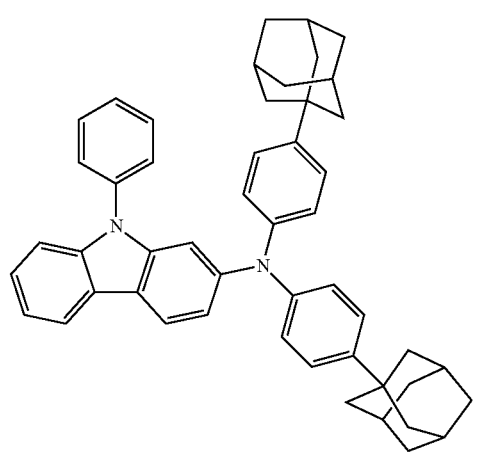
58
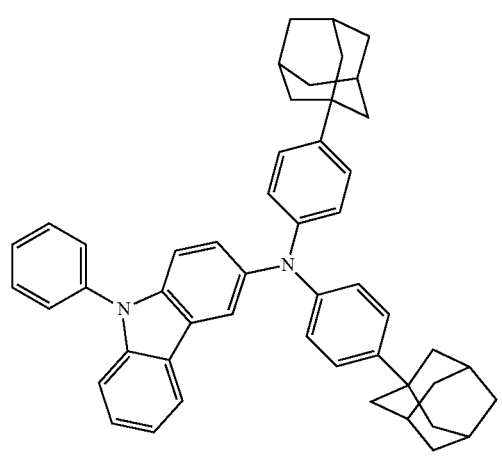
59
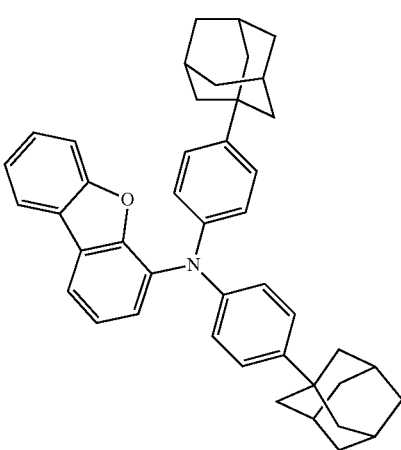
60
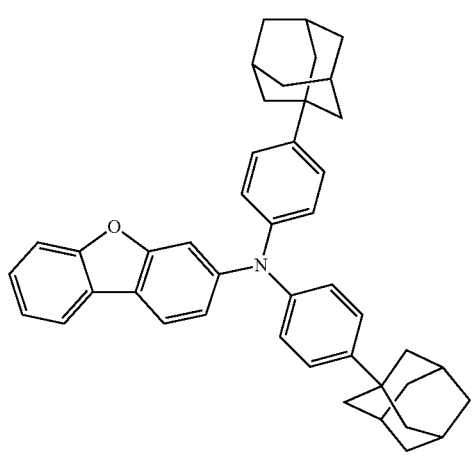
61
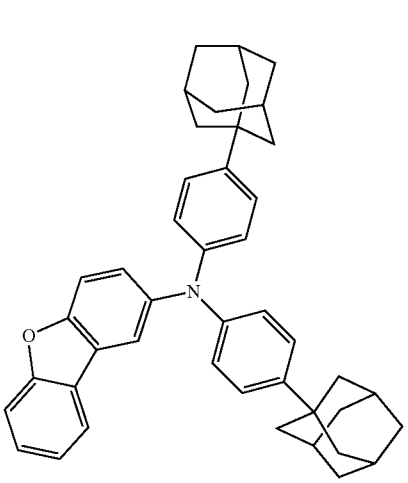

62
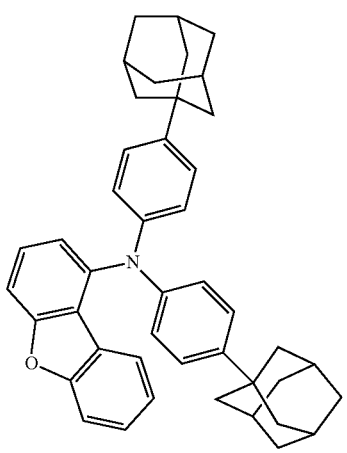
63
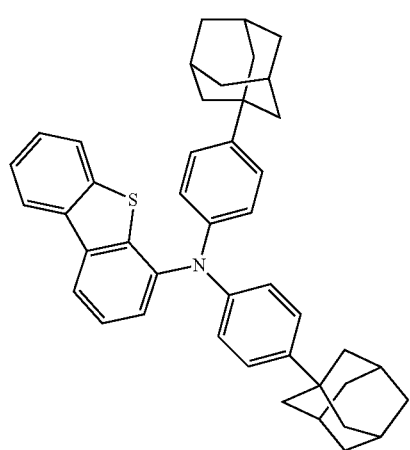
64
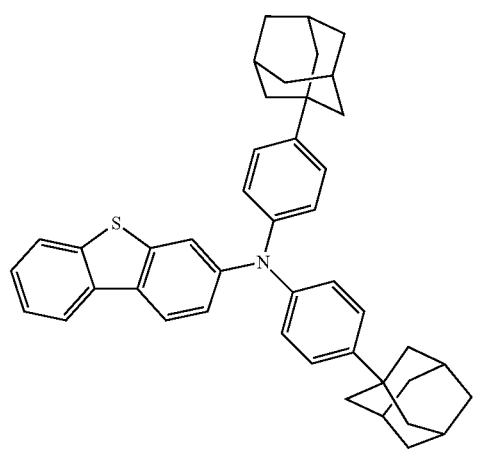
65
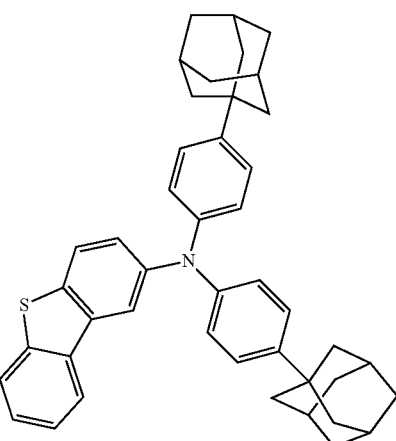
66
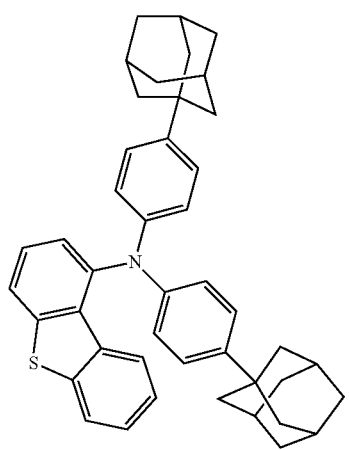
67
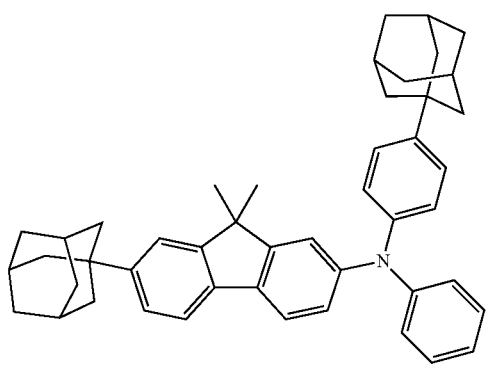

68
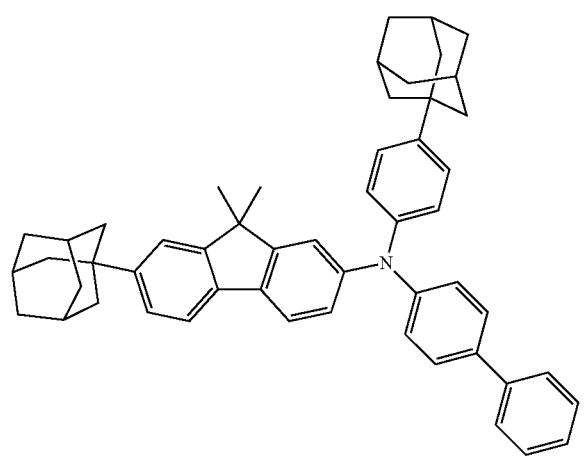
69
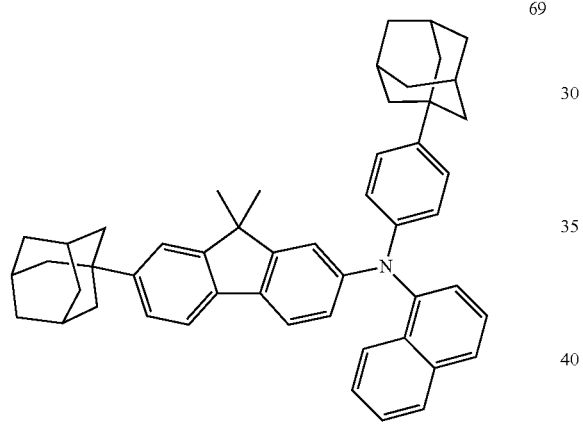
70
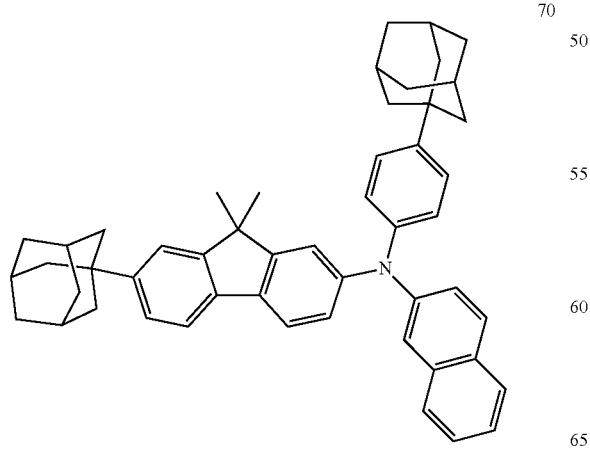
71
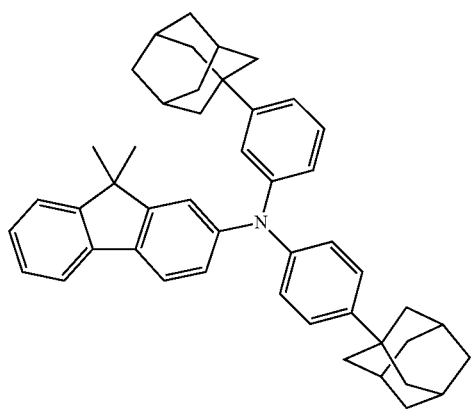
72
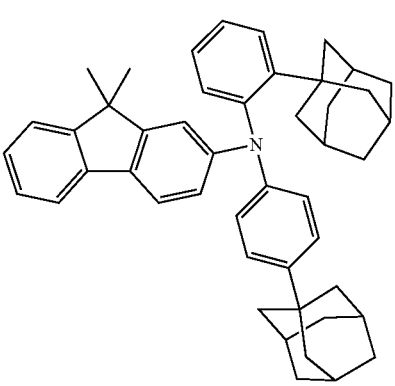
73
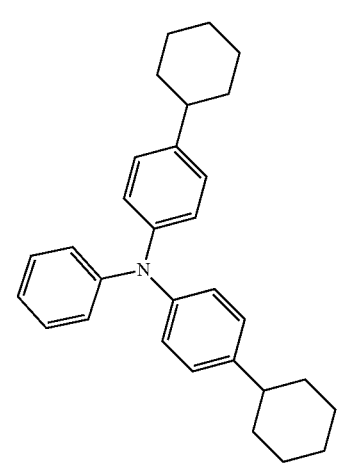

74
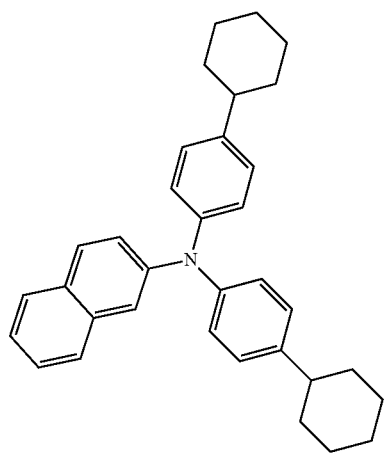
75
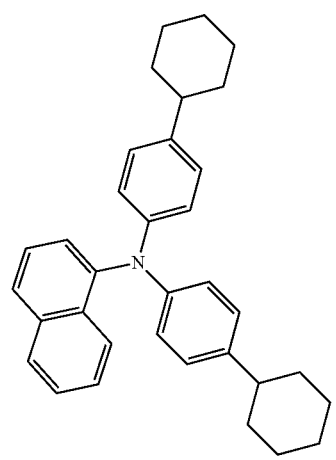
76
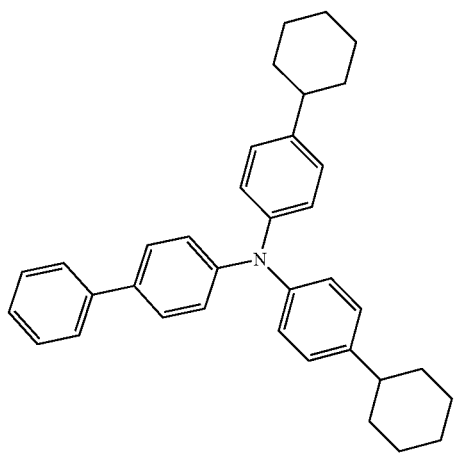
77
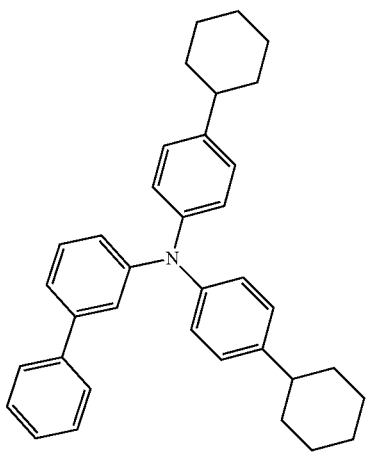
78
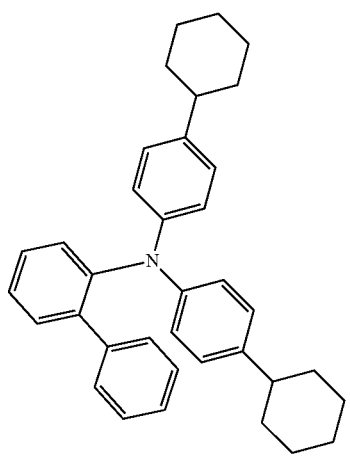
79
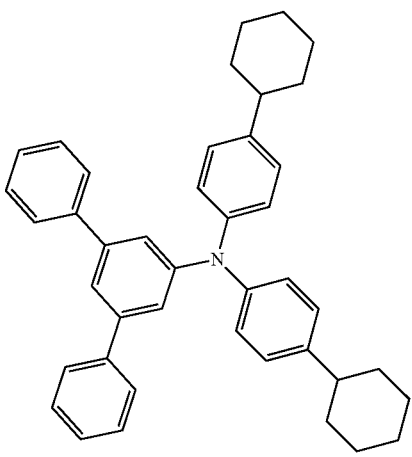

119
-continued
80
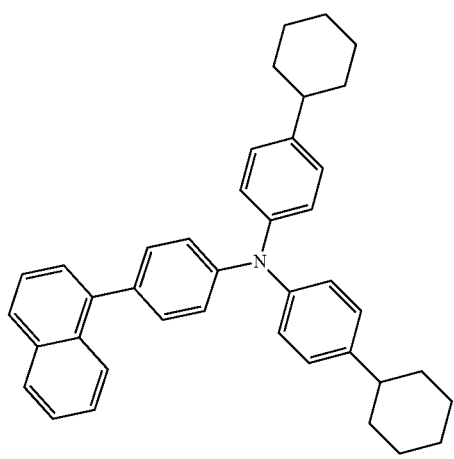
81
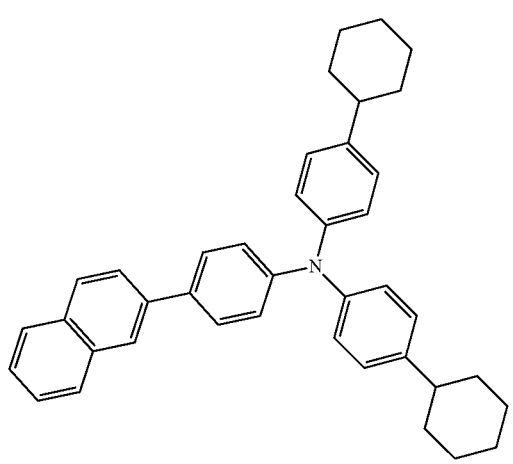
82
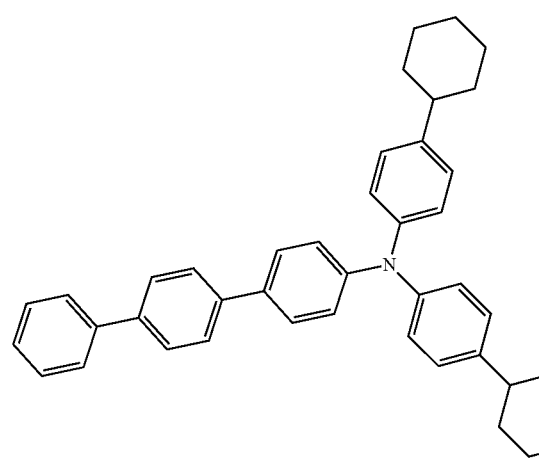
120
-continued
83
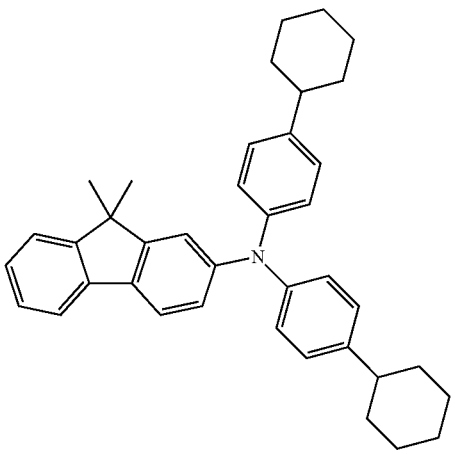
84
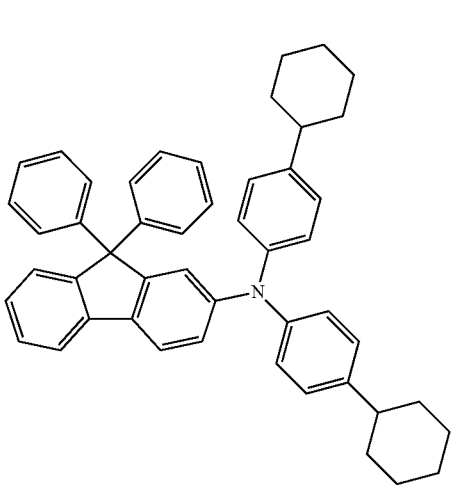
85

121
-continued
122
-continued
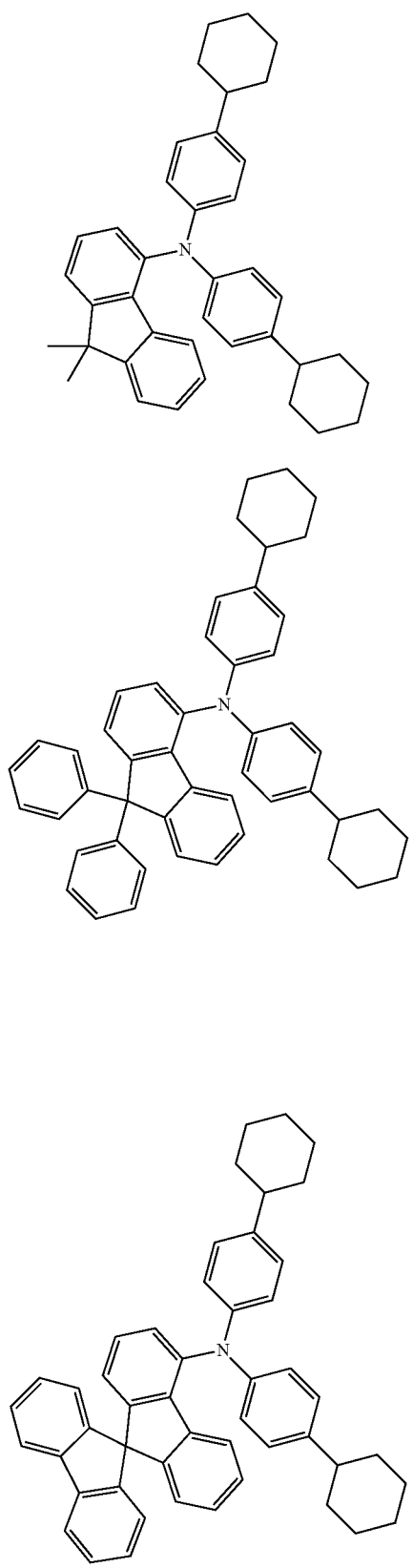
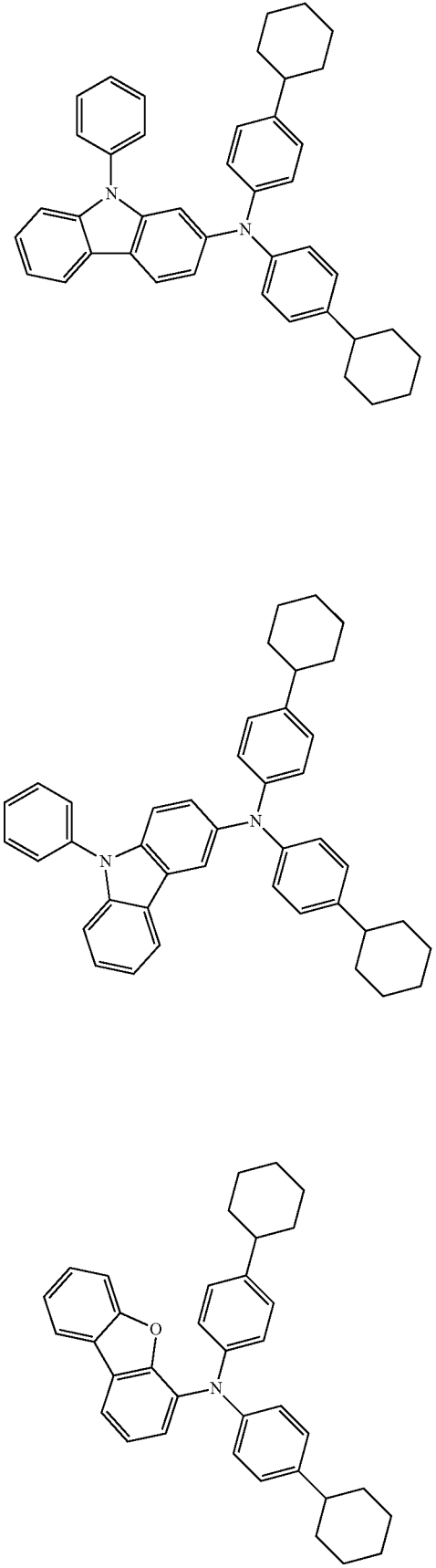

123
-continued
92
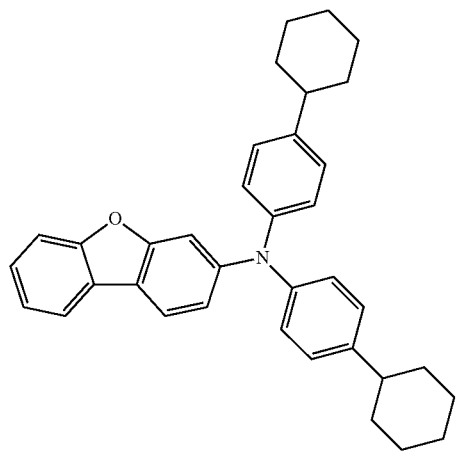
93
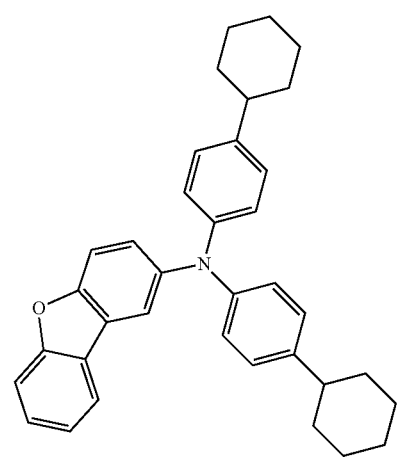
94
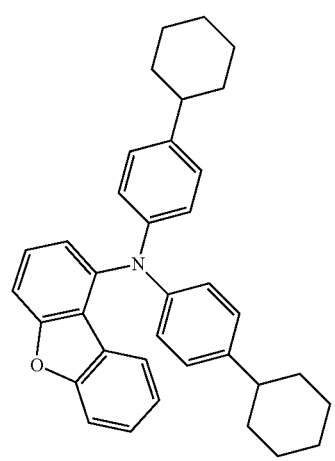
124
-continued
95
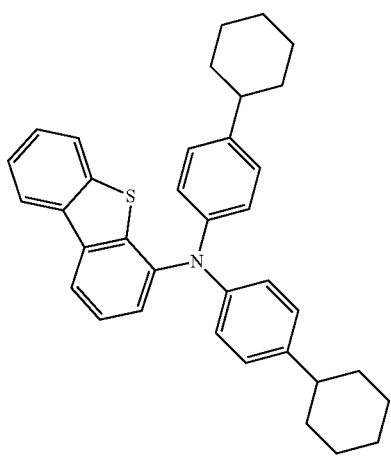
96
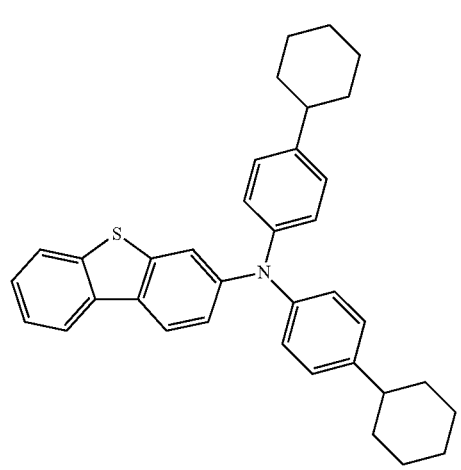
97
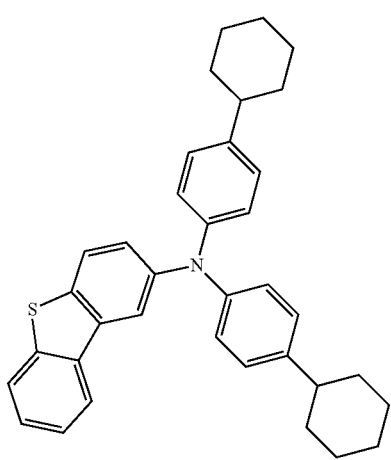

98
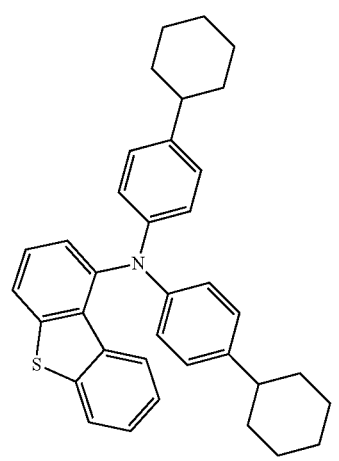
99
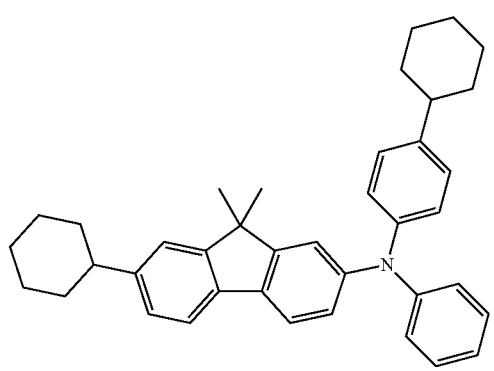
100
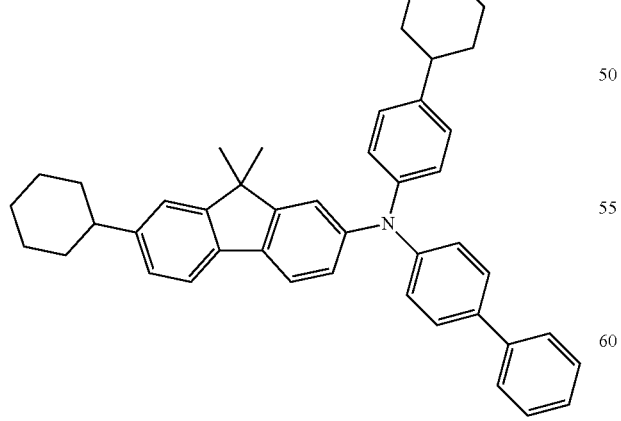
101
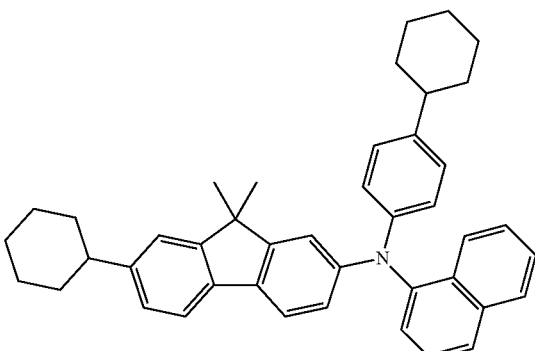
102
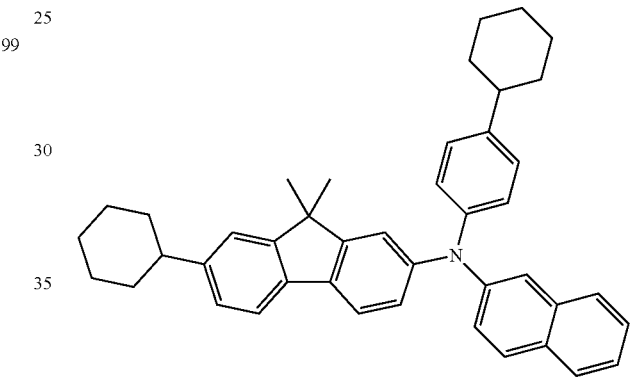
103
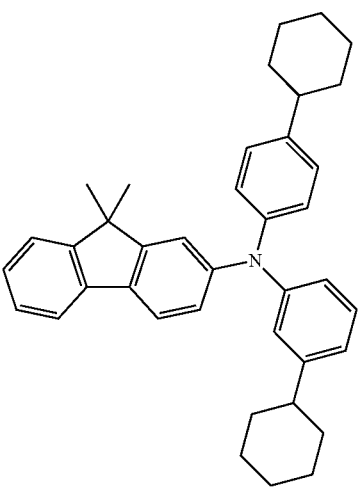

127
-continued
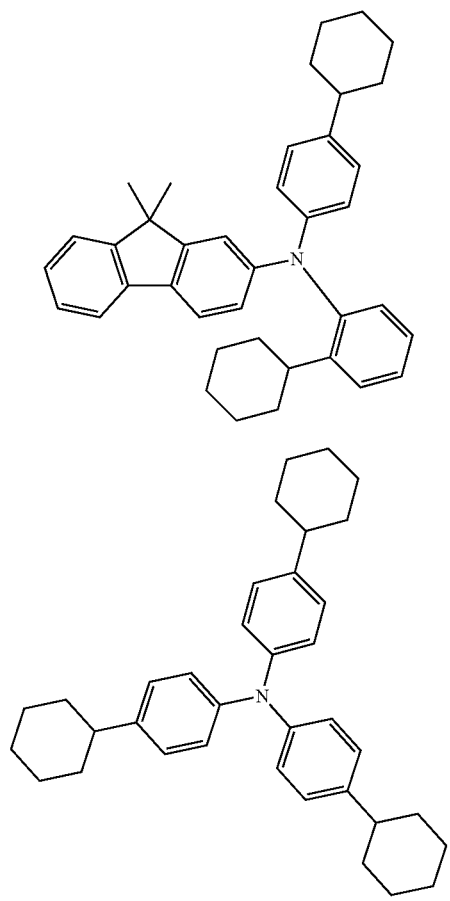
128
-continued
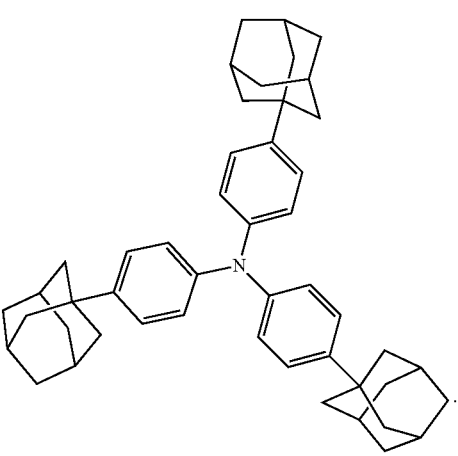
* * * * *